（12） United States Patent
Fukui et al.

(10) Patent No.: US 7,459,517 B2
(45) Date of Patent: *Dec. 2, 2008

(54) POLYHYDROXYALKANOATE, PROCESS FOR PREPARING THE SAME, AND RESIN COMPOSITION CONTAINING THE POLYHYDROXYALKANOATE

(75) Inventors: Tatsuki Fukui, Yokohama (JP); Tetsuya Yano, Atsugi (JP); Chieko Mihara, Isehara (JP); Shinya Kozaki, Tokyo (JP); Tsutomu Honma, Atsugi (JP); Takashi Kenmoku, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 146 days.

This patent is subject to a terminal disclaimer.

(21) Appl. No.: 10/531,226

(22) PCT Filed: Oct. 23, 2003

(86) PCT No.: PCT/JP03/13532

§ 371 (c)(1),
(2), (4) Date: Apr. 13, 2005

(87) PCT Pub. No.: WO2004/037889

PCT Pub. Date: May 6, 2004

(65) Prior Publication Data

US 2006/0079662 A1  Apr. 13, 2006

(30) Foreign Application Priority Data

Oct. 24, 2002  (JP)  ............................. 2002-310310
Mar. 28, 2003  (JP)  ............................. 2003-092408
Oct. 16, 2003  (JP)  ............................. 2003-356982

(51) Int. Cl.
*C08G 63/02* (2006.01)
*C08G 63/91* (2006.01)
*C12P 7/62* (2006.01)
*C08G 9/08* (2006.01)

(52) U.S. Cl. ................. 528/272; 430/108.5; 430/190.4; 528/271; 528/361; 525/64

(58) Field of Classification Search ........................ None
See application file for complete search history.

(56) References Cited

U.S. PATENT DOCUMENTS

| 4,393,167 A | 7/1983 | Holmes et al. ................. 525/64 |
| 4,442,189 A | 4/1984 | Lu et al. ....................... 430/45 |
| 4,480,021 A | 10/1984 | Lu et al. .................. 430/106.6 |
| 4,795,690 A | 1/1989 | Shindo et al. ............... 430/109 |
| 4,876,331 A | 10/1989 | Doi ............................. 528/361 |
| 4,925,765 A | 5/1990 | Madeleine .................. 430/110 |
| 5,004,664 A | 4/1991 | Fuller et al. ............. 430/106.6 |
| 5,135,859 A | 8/1992 | Witholt et al. ............... 435/135 |
| 5,200,332 A | 4/1993 | Yamane et al. ............... 435/135 |
| 5,292,860 A | 3/1994 | Shiotani et al. ............. 528/361 |
| 5,334,698 A | 8/1994 | Witholt et al. ............... 528/354 |
| 5,612,161 A | 3/1997 | Watanabe et al. ............ 430/110 |
| 5,618,855 A * | 4/1997 | Noda .......................... 521/189 |
| 5,667,927 A | 9/1997 | Kubota et al. ............... 430/109 |
| 6,492,147 B2 | 12/2002 | Imamura et al. ............. 435/135 |
| 6,521,429 B2 | 2/2003 | Honma et al. ............... 435/135 |
| 6,586,562 B2 | 7/2003 | Honma et al. ............... 528/361 |
| 6,635,782 B2 | 10/2003 | Honma et al. ................. 560/53 |
| 6,645,743 B1 * | 11/2003 | Honma et al. ............... 435/146 |
| 6,649,380 B1 | 11/2003 | Yano et al. .................. 435/135 |
| 6,649,381 B1 | 11/2003 | Honma et al. ............... 435/135 |
| 6,803,444 B2 | 10/2004 | Suzuki et al. ............... 528/361 |
| 6,872,788 B2 | 3/2005 | Imamura et al. ............. 525/440 |
| 6,908,721 B2 * | 6/2005 | Kenmoku et al. ........ 430/108.5 |
| 6,911,521 B2 | 6/2005 | Kenmoku et al. ........... 528/295 |
| 2003/0113368 A1 | 6/2003 | Nomoto et al. ............. 424/450 |
| 2003/0180899 A1 | 9/2003 | Honma et al. ............... 435/135 |
| 2003/0194789 A1 | 10/2003 | Honma et al. ............... 435/135 |
| 2003/0207412 A1 | 11/2003 | Kenmoku et al. ........... 435/135 |
| 2004/0067576 A1 | 4/2004 | Honma et al. ........... 435/252.34 |
| 2004/0081906 A1 * | 4/2004 | Kenmoku et al. ........ 430/108.4 |

(Continued)

FOREIGN PATENT DOCUMENTS

EP          1 236 752 A1     9/2002

(Continued)

OTHER PUBLICATIONS

Joanne M. Curley et al., "Production of Poly(3-hydroxyalkanoates) Containing Aromatic Substituents by *Pseudomonas oleovorans*," 29 *Macromol.* 1762-1766 (1996).

(Continued)

*Primary Examiner*—Vasu Jagannathan
*Assistant Examiner*—Gennadiy Mesh
(74) *Attorney, Agent, or Firm*—Fitzpatrick, Cella, Harper & Scinto

(57) ABSTRACT

A novel polyhydroxyalkanoate having a monomer unit represented by the formula (1), the unit having a carboxyl group substituting a ring structure at the end of side chain, obtainable by oxydizing vinyl or methyl group substituting a ring structure at the end of the side chain. The polyhydroxyalkanoate has high thermal stability, charge stablity, a high charge amount, improved dispersibility and biodegradability together, and therefore, suitable for resin moldings, and binders and charge controlling agents for toners used in the electrophotographic process.

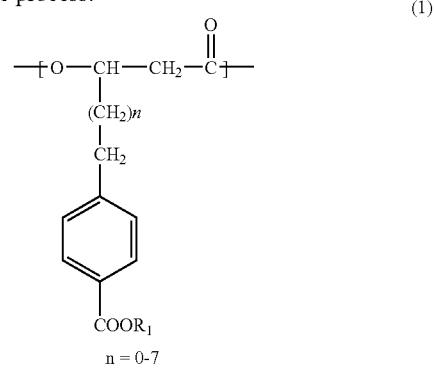

(1)

n = 0-7

34 Claims, 11 Drawing Sheets

U.S. PATENT DOCUMENTS

| | | | |
|---|---|---|---|
| 2004/0092702 A1 | 5/2004 | Honma et al. | 528/272 |
| 2005/0143574 A1 | 6/2005 | Minami et al. | 536/126 |
| 2006/0040366 A1 | 2/2006 | Kenmoku et al. | 435/135 |

FOREIGN PATENT DOCUMENTS

| | | | |
|---|---|---|---|
| EP | 1 336 635 | * | 8/2003 |
| JP | 59-190945 | | 10/1984 |
| JP | 60-108861 | | 6/1985 |
| JP | 61-3149 | | 1/1986 |
| JP | 63-38958 | | 2/1988 |
| JP | 63-88564 | | 4/1988 |
| JP | 63-184762 | | 7/1988 |
| JP | 5-7492 | | 1/1993 |
| JP | 5-93049 | | 4/1993 |
| JP | 6-15604 | B2 | 3/1994 |
| JP | 6-289644 | | 10/1994 |
| JP | 7-14352 | B2 | 2/1995 |
| JP | 7-72658 | | 3/1995 |
| JP | 7-120975 | | 5/1995 |
| JP | 7-265065 | | 10/1995 |
| JP | 8-19227 | B2 | 2/1996 |
| JP | 8-179564 | | 7/1996 |
| JP | 8-262796 | | 10/1996 |
| JP | 2623684 | B2 | 4/1997 |
| JP | 2642937 | B2 | 5/1997 |
| JP | 9-191893 | | 7/1997 |
| JP | 9-274335 | | 10/1997 |
| JP | 9-281746 | | 10/1997 |
| JP | 2807795 | B2 | 7/1998 |
| JP | 2989175 | B1 | 10/1999 |
| JP | 2001-69968 | | 3/2001 |
| JP | 2001-288256 | | 10/2001 |
| JP | 2002-80571 | | 3/2002 |
| WO | WO 2004/097417 A1 | | 11/2004 |

OTHER PUBLICATIONS

Bruce A. Ramsay et al., "Effect of Nitrogen Limitation on Long-Side-Chain Poly -β-Hydroxyalkanoate Synthesis by *Pseudomonas resinovarans*," 58(2) *Appl. Environ, Microbiol.* 744-46 (1992).

Katharina Fritzsche et al., "An Unusual Bacterial Polyester with a Phenyl Pendant Group," 191 *Macromol. Chem.* 1957-65 (1990).

Y.B. Kim et al., "Preparation and Characterization of Poly(β-Hydroxyalkanoates) Obtained from *Pseudomonas oleovorans* with Mixtures of 5-Phenylvaleric Acid and *n*-Alkanoic Acids," 24 *Macromol.* 5256-60 (1991).

Safwat Antoun et al., "Production of Chiral Polyester by *Pseudomonas oleovorans* Grown with 5-Phenyl-2,4-Pentadienoic Acid," 3(6) *Chirality* 492-94 (1991).

Suzette M. Aróstegui et al., "Bacterial Polyesters Produced by *Pseudomonas oleovorans* Containing Nitrophenyl Groups," 32 *Macromol.* 2889-95 (1999).

Helmut Ritter et al., "Bacterial Production of Polyesters Bearing Phenoxy Groups in the Side Chains, 1 Poly(3-Hydroxy-5-Phenoxypentanoate- *co*-3-Hydroxy-9-Phenoxy-Nonanoate) from *Pseudomonas oleovorans*," 195 *Macromol. Chem. Phys.* 1665-72 (1994).

Young Baek Kim et al., "Poly-3-hydroxyalkanoates Produced from *Pseudomonas oleovorans* Grown with ω-Polyhydroxyalkanoates," 29 *Macromol.* 3432-35 (1996).

Ohyoung Kim et al., "Bioengineering of Poly(β-hydroxyalkanoates) for Advanced Material Applications: Incorporation of Cyano and Nitrophenoxy Side Chain Substituents," 41 (Supp. 1) *Can. J. Microbiol.* 32-43 (1995).

Richard A. Gross et al., "Cyanophenoxy-Containing Microbal Polyesters: Structural Analysis, Thermal Properties, Second Harmonic Generation and In-Vivo Biodegradability," 39 *Polymer International* 205-13 (1996).

Marianela Andújar et al., "Polyesters Produced by *Pseudomonas oleovorans* Containing Cyclohexyl Groups," 30 *Macromol.* 1611-15 (1997).

M.Y. Lee et al., "Hydrophilic Bacterial Polyesters Modified with Pendant Hydroxyl Groups," 41 *Polymer* 1703-09 (2000).

Lindsay H. Briggs et al., "Degradation of the Lanosterol Side-chain," *J.C.S. Perkin I*, 806-09 (1973).

J.K. Stille et al., "Tetracyclic Dienes. I. The Diels-Alder Adduct of Norbornadiene and Cyclopentadiene," 81 *J. Am. Chem. Soc.* 4273-75 (Aug. 1959).

Henry J. Vogel et al., "Acetylorinithinase of *Escherichia coli* : Partial Purification and Some Properties," 218 *J. Biol. Chem.* 97-106 (1956).

Harry R. Allcock et al., "Reactions of Steroid Salts with Hexachlorocyclotriphosphazene," 46 *J. Org. Chem.* 13-22 (1981).

Hideki Abe et al., "Biosynthesis from Gluconate of a Random Copolyester Consisting of 3-hydroxybutyrate and Medium-Chain-Length 3-Hydroxyalkanoates by *Pseudomonas* sp. 61-3," 16(3) *Int. J. Biol. Macromol.* 115-19 (Jun. 1994).

*Organic Synthesis*, vol. 4, pp. 695-699 (1963).

Marie-Maud Bear et al., "Preparation of a Bacterial Polyester with Carboxy Groups in Side Chains," 4 *Chemistry* 289-93 (2001).

* cited by examiner

POLYHYDROXYALKANOATE, PROCESS FOR PREPARING THE SAME, AND RESIN COMPOSITION CONTAINING THE POLYHYDROXYALKANOATE

TECHNICAL FIELD

The present invention relates to a novel polyhydroxyalkanoate (hereinafter referred to as PHA for short) and a process for preparing the same. Further, the present invention relates to a resin composition, a molding using the same, and a method for producing the molding. Still further, the present invention relates to a charge controlling agent used in recording methods that utilizes electrophotographic method, electrostatic recording method, magnetic recording method, etc., a binder resin that can be used in toners for developing electrostatic charge images, a toner for developing electrostatic charge images, and image forming method and apparatus that use the toner.

BACKGROUND ART

Problems with Resins Traditionally Used

Plastics such as polyethylene terephthalate (PET) resin, polyester resin, vinyl chloride resin and polyolefin resin have been used as moldings for many applications, such as containers for foods, bottles for drinks, containers for cosmetics and flowerpots.

These plastics are mostly disposed of after use. Although these plastic wastes have been disposed of by incineration or landfill, disposal of such wastes by incineration has caused problems of: durability of incinerators that are exposed to high combustion temperatures due to high combustion energy generated by the plastic wastes being incinerated; disposal costs resulting from the installation of incinerators resistant to high temperatures; and air pollution caused by the generation of hazardous incineration gases such as carbon monoxide, sulfur compounds, chlorine gas and dioxin. As to disposal by landfill, it does not allow the plastic wastes to be decomposed, but to remain almost indefinitely and accumulate as wastes on waste disposal sites. This has given rise to a serious social problem with wastes. Moreover, since the plastic wastes exist in the ground in the as-disposed of form, they might produce a problem of unstable ground of landfills and affect the natural environment and various living organisms of the landfills and their vicinities.

As one solution to these problems, biodegradable resins have lately attracted considerable attention. The term "biodegradable resins" here means resins that have almost the same physical properties as those of general-purpose plastics when being used as materials, but, once disposed of, are promptly degraded by microorganisms in the natural environment, such as on the ground, in the soil, in compost, in activated sludge and in water. Biodegradable resins are degraded minutely and some of them are degraded to carbon dioxide and water.

As biodegradable resins that satisfy the above described requirements, not only specific polyester biodegradable resins, but also blended resin compositions, such as starch-ethylene-vinyl alcohol copolymer resins, ethylene-vinyl alcohol copolymer resins-aliphatic polyester resins and aliphatic polyester resins-polyolefin resins, have been known. And these resins or resin compositions have been shaped into various forms such as bottles and used for practical applications. However, excellent resin compositions have not been proposed yet that offer a good balance of moldability required in the production of containers, along with various physical properties required for the containers and biodegradability required after the containers are disposed of. For example, resin compositions have not been proposed yet such that have both biodegradability and heat resistance after molding.

<Polyhydroxyalkanoate (PHA)>

In recent years, there has been proposed, as a solution to environmental pollution caused by the wastes of plastic moldings etc., the use of biodegradable resins synthesized by microorganisms as molding materials. As biodegradable resins originated from microorganisms, have been known, for example, polyhydroxyalkanoates (hereinafter sometimes referred to as PHAs), such as copolymers of poly-3-hydroxy-n-butyric acid (hereinafter sometimes referred to as PHB) or 3-hydroxy-n-butyric acid (hereinafter sometimes referred to as 3HB) with 3-hydroxy-n-valeric acid (hereinafter sometimes referred to as 3HV) (hereinafter sometimes referred to as PHB/Vs), polysaccharides such as bacterial cellulose and pullulan, and polyamino acids such as poly-γ-glutamic acid and polylysine. Particularly PHAs are melt-fabricable and can be used for various products, like conventional plastics. In addition, they are excellent in biocompatibility; therefore, their applications to flexible members for medical use are also being expected.

Many types of microorganism have been heretofore reported to produce PHA and accumulate PHA in the cell[31]. It is known that such PHA may have various compositions and structures depending on the type of microorganism to be used for the production of the PHA, the culture medium composition and the culture conditions, and hitherto studies have been conducted mainly on control of the composition and structure of PHA to be produced in terms of improvements of physical properties of PHA.

Especially, biosynthesis of PHA obtained by polymerization of a monomer units with a relatively simple structure such as 3HB, 3HV, 3-hydroxyhexanoic acid (hereinafter referred to as 3HHx) and 4-hydroxy-n-butyric acid (hereinafter referred to as 4HB) have been studied, and production using various microorganisms has been reported[1-7].

However, such straight-chain aliphatic polyesters as copolymers of 3HB or/and 3HV etc. tend to undergo thermal degradation because of close melting point and thermal degradation temperature. As a result, their extrusion workability is poor. Further, the straight-chain aliphatic polyesters are brittle due to their high crystallinity, and their extensibility tends to be low and mechanical properties tend to deteriorate. Thus, the straight-chain aliphatic polyesters alone are not preferable as materials for moldings.

In recent years, investigations have been made on a polyhydroxyalkanoate composed of medium-chain-length 3-hydroxyalkanoic acid units of about 4 to 12 carbon atoms (hereinafter sometimes referred to as mcl-PHA for short) vigourously.

It has been confirmed production of mcl-PHA using acyclic aliphatic hydrocarbons, octanoic acid, hexanoic acid, sodium gluconate etc. as a carbon source[8,32,33]. However, these mcl-PHAs have low melting points, and when the temperature is above 50° C., they become sticky and soft seriously. Thus, these mcl-PHAs alone are low in serviceability as materials for moldings.

The above described PHAs are all PHAs that are synthesized vai β-oxidation of hydrocarbons or via synthesis of fatty acid from saccharides in microorganisms and consist of monomer units having an alkyl group alone on their side chains (hereinafter referred to as usual-PHAs) or those similar to them (for example, PHA having an alkenyl group on side chains of which double bond is in the portion other than the end). However, if considering a wide range of application as a plastic, the above described PHAs are not satisfactory in terms of physical properties, at present.

For further expanding the range of, for Example, application of PHA, it is important to conduct a wide range of studies on the improvement of properties, and for this purpose, development and search of PHA including monomer units of a variety of structures is prerequisite. On the other hand, PHA with a substituent group introduced in the side chain ("unusual PHA") can be expected to be developed as a "functional polymer" with very useful functions and properties originating from the introduced substituent group by selecting the introduced substituent group according to desired characteristics and the like. That is, it is also an important challenge to conduct of development and search of excellent PHA enabling such functionality and biodegradability to be compatible with each other. Examples of substituent groups include groups containing aromatic rings (phenyl group, phenoxy group, etc.), ester groups, unsaturated groups having a double bond on the terminal (alkenyl groups, alkadienyl groups, in particular, allyl groups), cyano groups, halogenated hydrocarbons and epoxide. For example, there are reports on production of: PHA containing a phenyl group or its partially substituted group such as PHA containing 3-hydroxy-5-phenylvaleric acid as a unit using 5-phenylvaleric acid as a substrate[34-36], PHA containing 3-hydroxy-5-(4'-tolyl)valeric acid as a unit using 5-(4'-tolyl) valeric acid as a substrate[37], and PHA containing 3-hydroxy-5-(2',4'-dinitrophenyl)valeric acid and 3-hydroxy-5-(4'-nitrophenyl)valeric acid as a unit using 5-(2',4'-dinitrophenyl)valeric acid as a substrate[38]; PHA containing a phenoxy group or its partially substituted group such as PHA containing 3-hydroxy-5-phenoxyvaleric acid and 3-hydroxy-9-phenoxynonanoic acid using 11-pheoxyundecanoic acid as a substrate[39], PHA containing a 3-hydroxy-4-phenoxybutyric acid unit and a 3-hydroxy-6-phenoxyhexanoic acid unit from 6-phenoxyhexanoic acid, PHA containing a 3-hydroxy-4-phenoxybutyric acid unit, a 3-hydroxy-6-phenoxyhexanoic acid unit, and a 3-hydroxy-8-phenoxyoctanoic acid unit from 8-phenoxyoctanoic acid, and PHA containing a 3-hydroxy-5-phenoxyvaleric acid unit and a 3-hydroxy-7-phenoxyheptanoic acid unit from 11-phenoxyundecanoic acid[40]. There is also a report[9] on a homopolymer consisting of 3-hydroxy-5-(monofluorophenoxy)pentanoate (3H5(MFP)P) units or 3-hydroxy-5-(difluorophenoxy)pentanoate (3H5(DFP)P) units, and a copolymer containing at least (3H5(MFP)P) units or (3H5(DFP)P) units, of which advantage is to provide stereoregularity and water repellency while maintaining a high melting point and good processability.

Further, studies are conducted on cyano-substituents and nitro-substituents in addition to the fluorine-substituent described above. For example, PHA containing 3-hydroxy-p-cyanophenoxyhexanoic acid or 3-hydroxy-p-nitrophenoxyhexanoic acid as a monomer unit is produced using octanoic acid and p-cyanophenoxyhexanoic acid or p-nitrophenoxyhexanoic acid as substrates[41,42].

These reports are useful in obtaining polymers each having an aromatic ring in the side chain of PHA and having properties derived therefrom unlike general PHA whose side chain contains an alkyl group. Further, as the example of unusual-PHA having a cyclohexyl group, production of PHA from cyclohexylbutyric acid or cyclohexylvaleric acid has been reported[43].

Moreover, as a new category, such studies are conducted that PHA having an appropriate functional group on a side chain is produced to try to produce a new function utilizing the functional group, not only the property change.

It is reported that a change of solubility in solvents has been found such that 3-hydroxyalkanoic acid having diol on the side chain terminal, synthesized by an oxidation reaction using potassium permanganate after producing PHA containing as a monomer unit 3-hydroxyalkenoic acid having an unsaturated bond in the terminal of the side chain using 10-undecenoic acid as a substrate, is rendered soluble in polar solvents such as methanol, acetone-water mixture (80/20, v/v) and dimethylsulfoxide, and insoluble in nonpolar solvents such as chloroform, tetrahydrofuran and acetone[44].

It is reported that an improvement in speed of decomposition has been found for PHA containing 3-hydroxy-9-carboxynonanoic acid as a monomer unit, synthesized by an oxidization cleavage reaction using potassium permanganate after producing PHA containing as a monomer unit 3-hydroxy-10-undecenoic acid using 10-undecenoic acid as a substrate[45].

However, the PHA in the above report is a copolymer of PHA (usual-PHA) composed of monomer units each having a carboxyl group at the end of its side chain and monomer units each having a straight-chain alkyl group on its side chain (usual PHA). As a result, the problems of low glass transition temperature etc. arise.

On the other hand, polymers each having an aromatic ring on its side chain are thermally stable and polymers having a carboxylphenyl unit are also expected to have high thermal stability, moreover, their carboxyl group is an active group applicable in various ways; accordingly, these polymers are very useful from the viewpoint of their application as functional materials.

[Technical Background of Toner]

So far, many methods have been known for electrophotography, and those methods are generally carried out in such a manner that an electric latent image is formed on an image-holding member (photosensitive member) by a variety of means using a photoconductive substance, the latent image is then developed with a toner to form a visible image, and the toner image is transferred onto a transfer material such as a paper as necessary, followed by fixing the toner image on the object transfer material by heat and/or pressure or the like to obtain a copy. For the method for visualizing the electric latent image, a cascade development method, a magnetic brush development method, a pressurizing development method and the like are known. Further, a method using a magnetic toner and a rotary development sleeve with a magnetic pole placed at the center thereof where the magnetic toner is caused to fly from the development sleeve onto the photoconductor by a magnetic field is also used.

Development systems for use in development of an electrostatic latent image include a two-component development system using a two-component type developer constituted by a toner and a carrier, and a one-component development system using a one-component type developer constituted only by a toner and using no carrier.

Here, the colored fine particle, so-called toner, has a binder resin and a coloring material as essential components, and in addition thereto, magnetic powders and the like as necessary.

<Binder Resin>

The bulk of a toner consists of a binder resin; therefore, the physical properties of the binder resin largely affect those of the toner. For example, the binder resin is required to have delicate hardness and heat fusion properties, while the toner, which is obtained by grinding and classifying the binder resin in which a colorant etc. is dispersed, is required to show a good flowability without producing fine powder even when subjected to mechanical impact by stirring in a developing equipment and without cohering and, at the time of its fixing, it is required to melt promptly at lower temperatures and, once it is melted, the melted toner is required to show cohesiveness. In other words, controlling the physical properties of the binder resin allows controlling the physical properties of the toner.

As a binder resin, traditionally, styrene-acrylic ester copolymer, polyester resin, epoxy resin, olefin resin, etc. have been used. And of these resins, polyester resin comes into extensive use as a resin for heat roll fixing toners, since it has advantages of good dispersion of toner additives, such as carbon black, wettability to transfer paper and superior fixing properties.

In recent years, people worldwide have become conscious of recycling of resources, reduction of wastes, improvement in safety of wastes, etc. from the viewpoint of environmental protection. These problems are not exception in the field of electrophotography. Specifically, with the spread of copiers and printers, the amount of toners fixed on paper, toner wastes and paper having been used for printing has increased year by year. Conventional toners, however, are all composed of stable artificial compounds, and hence hard to decompose; as a result, they can sometimes remain in every environment, such as in the soil and in water, for a long period of time. Further, one of the important considerations in recycling of resources is recycling and reusing plain paper; however, the conventional binder resins, typified by styrene resin, make hard the deinking by alkali hydrolysis, which is one of the problem in recycling plain paper. The safety of wastes is also an important consideration from the viewpoint of conservation of the global environment and effect on the human body.

<Application of Biodegradable Resin to Toner>

Also in the field of electrophotography, a method in which a biodegradable resin is used as a binder resin has been proposed as a method to realize a toner that can be discarded without environmental pollution.

For example, a Japanese Patent Application publication[10] discloses an electrophotographic toner particularly for heated roll fixation characterized in that at least the binder resin contains a plant based wax and a biodegradable resin (e.g. polyester produced by microorganism, and natural polymer material of plant or animal origin), and the above described plant based wax is added in the above described binder in an amount of 5 to 50% by weight.

In addition, Japanese Patent Application publication[11] discloses an electrophotographic toner containing a binder resin and a coloring agent, characterized in that the binder resin is composed of a biodegradable resin (e.g. aliphatic polyester resin), and the coloring agent is composed of non-water soluble pigments.

Further, U.S. Pat. No. 5,004,664 discloses a toner that includes, as a constituent, a biodegradable resin, in particular, polyhydroxybutyric acid, polyhydroxyvaleric acid, a copolymer or a blend thereof. With these prior arts, since the binder resins used are biodegradable, the toners can be certainly decomposed in the soil if they are disposed of by landfill; however, such resins are still problematic in essential functions as binder resins, specifically the durability as a toner is poor, and moreover, the charge characteristics of the toner are instable because of high hygroscopicity. For example, PHB is a hard and brittle material having a melting point of 180° C., a degree of crystallinity of 50 to 70%, a Young's modulus of elasticity of 3.5 GPa and an elongation percentage of 5%, inadequate for practical use as a toner binder.

There has been proposed toners including a polylactic acid-based aliphatic polyester, as a main ingredient, that are biodegradable, efficiently decomposed by alkali hydrolysis, and hence useful for recycling of paper. For example, there is proposed in Japanese Patent Application publication[13] a method of producing a toner using lactic acid homopolymer, in which polylactic acid obtained by ring-opening polymerization process is shown as a representative example.

In the ring-opening polymerization process, an approach is adopted to subject lactic acid to dehydration reaction to form an oligomer, depolymerize the oligomer to lactide as a cyclodimer, and subject lactide to ring-opening polymerization. Since the method follows such a complicated procedure, the toner resin using the resultant polylactic acid becomes very costly.

Further, the ring-opening polymerization is a cationic ring-opening polymerization; as a result, it requires the steps of making the solvent used anhydrous; and removing ion species that serve as a polymerization inhibitor, which means low production efficiency. Furthermore, since the kind of monomer usable in the production of polyester is limited to cyclic ester, it is not easy to control the physical properties which the polyester is required to have as a resin for toners and it is also hard to copolymerize the monomer with other various monomers to control the balance of the degradability and the physical properties of the polyester obtained. In this respect, there have been demands for biodegradable polyesters which are inexpensive and whose physical properties are easy to control. If a toner is produced using polylactic acid, as a main ingredient, without any modification, problems of shelf stability and off-set resistance arise with the toner; therefore, such a toner has not come in practice yet.

There is disclosed in a Japanese Patent Application publication[14] a toner for developing electrostatic charge images that is characterized by including: a polyester resin, which is obtained by subjecting a composition containing lactic acid and oxycarboxylic acid of three or more functional groups to dehydration polycondensation; and a colorant. In this toner, however, since the polyester resin is formed through the dehydration polycondensation reaction of the alcohol group of lactic acid and the carboxylic group of oxycarboxylic acid, the molecular weight of the resultant resin tends to be high, and therefore, its biodegradability probably tends to become low. Furthermore, problems of shelf stability and off-set resistance also arise with the toner composed of such a resin, like the toner disclosed in Japanese Patent Application Laid-Open No. H7-120975.

Further, there is disclosed in a Japanese Patent Application publication15 a toner for developing electrostatic charge images that is characterized by including: a urethane polyester resin, which is obtained by cross-linking polylactic acid with a polyvalent isocyanate of three or more functional groups; and a colorant. However, the polyester resin is also problematic in its of biodegradability, and problems of shelf stability and off-set resistance also arise with the toner composed of such a resin, like the toners described above.

Polycaprolactone, which is a typical homopolymer of hydroxycarboxylic acid, has a low melting point and a low glass transition point and, due to its melting point as low as 60° C., it alone is not suitably used as a binder resin, though it is excellent in compatibility with various resins. Polylactic acid has a high glass transition point (60° C.) and particularly that of crystallinity is a thermoplastic polymer having a high melting point (around 180° C.); however, it has not come in practice as a binder resin yet, as described above. Further, the conventional toner resins each composed of degradable polyester are generally poor in grindability, and they are difficult to use as a binder resin that accounts for 90% of a toner with particle diameter of about 10 μm. Thus, there has been a strong demand for improvement in the physical properties of the conventional resins from the viewpoint of their practical use as a binder resin for toners.

All of the toners for electrophotography described above use biodegradable resins as their binder resin and are recognized to produce the effect of contributing to the environmental conservation.

<Charge Controlling Agent>

For the method for imparting an electric charge to the toner, the electrifiability' chargeability) of the binder resin itself may be used without using a charge controlling agent, but in this method, charge stability with time and humidity resistance are compromised, thus making it impossible to obtain high quality images. Therefore, the charge controlling agent is usually added for the purpose of maintaining and controlling the; charge of the toner.

Charge controlling agents well known in the art today include, for example, azo dye metal complexes, aromatic dicarboxylic acid-metal complexes and salicylic acid derivative-metal complexes as negative friction charging agents. In addition, as positive friction charging agents, nigrosine-based dyes, triphenylmethane-based dyes, various types of quaternary ammonium salts and organic tin compounds such as dibutyl tin oxide are known, but toners containing these substances as the charge controlling agent do not necessarily fully satisfy quality characteristics required for the toner such as the electrifiability and stability with time depending on their compositions.

For example, a toner containing an azo dye metal complex known as a negative charge controlling agent has an acceptable charge level, but may have reduced dispersibility depending on the type of binder resin to be combined because the azo dye metal complex is a low-molecular crystal. In this case, the negative charge controlling agent is not uniformly distributed in the binder resin, the charge level distribution of the obtained toner is significantly lacking in sharpness, and the obtained image has a low gray-level, resulting in a poor image formation capability. In addition, the azo dye metal complex has a unique color tone, and is thus presently used only for toners having limited colors around black, and if the azo dye metal complex is used as a color toner, its lack in clarity as a coloring agent required for obtaining an image having a high level of requirement for the color tone is a serious problem.

In addition, examples of almost colorless negative charge controlling agents include aromatic dicarboxylic-acid metal complexes, but they may be disadvantageous due to the fact that they are not perfectly colorless, and that they have low dispersibility peculiar to low-molecular-weight crystals.

On the other hand, nigrosine based dyes and triphenylmethane based dyes are presently used only for toners having limited colors around black because they are colored themselves, and may be poor in time stability of toners in continuous copying. In addition, conventional quaternary ammonium salts may have insufficient humidity resistance when formed into toners, and in this case, the stability with time may be so poor that high quality images are not provided as they are repeatedly used.

In addition, in recent years, attention has been given worldwide to reduction of wastes and improvement of safety of wastes in terms of environmental protection. This problem applies to the field of electrophotography as well. That is, as imaging apparatuses have been widely used, the amounts of wastes of printed papers, discarded toners and copying papers have increased year by year, and the safety of such wastes is important from a viewpoint of protection of global environment.

In the light of these problems, polymer charge controlling agents have been studied. Examples are the compounds disclosed in U.S. Pat. Nos. 4,480,021, 4,442,189 and 4,925,765, Japanese Patent Application publications[20-22]. Further, as polymer charge controlling agents that allow toners to exhibit negatively charged characteristics, copolymers of styrene and/or α-methylstyrene with alkyl(meth)acrylate ester or alkyl(meth)acrylate amide having a sulfonic acid group are often used[23-27]. These materials offer the advantage of being colorless; however, to obtain an intended amount of charge, a large amount of the materials needs to be added.

As described above, these compounds do not offer adequate performance as charge controlling agents, and problems of the amount of charge, charge build-up characteristics, stability over time and environment stability arise with them. Further, taking into consideration not only the functions of charge controlling agents, but also their effect on the human body as well as the environment, charge controlling agents are strongly wanted which can be produced using safer compounds by safer and moderate synthesis process and realize the reduction in amount of organic solvent used.

However, there has been known no report about the use of a biodegradable resin for a charge controlling agent, and there is still great room for improvement of charge controlling agent in view of the environmental conservation etc.

<Other Prior Art Documents>

In the invention of this application, the microorganisms described in elsewhere[28,29] are used. The description of media in Reference 46 can also be quoted. The other techniques related to the invention of this application include, for example, techniques for obtaining carboxylic acid by cleaving carbon-carbon double bonds with an oxidizing agent[30, 47-50] and a technique for synthesis of 5-(4-methylphenyl) valeric acid[51].

In conventional plastic moldings, toner binders for toners and charge controlling agents used in electrophotography, resins have been used which will not be decomposed in the natural world and may cause various environmental problems when disposed of and the amount of such resins used tends to increase year by year. Under these conditions, there has been a strong demand that measures should be taken as soon as possible against waste disposal problems.

Thus, studies have been conducted on the use of biodegradable resins for these applications, as described above; however, the following problems have arisen with conventional biodegradable resins.

First, a polyester obtained by subjecting to a chemical reaction/treatment a polyester having the vinyl group reported so far can be given a variety of functions, but does not necessarily have satisfactory thermal characteristics because of the existence of a middle to long alkyl chain in the side chain. That is, the glass transition temperature and melting point of the polyester is low, resulting in significant limitations to the range of applications as moldings and films.

On the other hand, a polyester having an aromatic ring on the side chain generally has a high melting point and thus finds a wide range of applications as moldings and films as described previously. However, the polyhydroxyalkanoate type polyester having units each containing an aromatic ring substituted with a functional group capable of enduring a variety of applications includes only examples described above, and further more functional polyhydroxyalkanoate type polyesters have been desired.

This invention is made to solve the above described problems; accordingly, the object of this invention is to provide a polyhydroxyalkanoate-type polyester having a unit that includes an aromatic ring whose hydrogen is substituted with a carboxyl group, a functional group used for various applications, and a process for preparing the same.

Another object of this invention is to provide a resin composition that includes the above polyhydroxyalkanoate-type polyester and is capable of preventing the occurrence of various environmetal problems due to its disposal, moldings using the same, and a method of producing the moldings. Still another object of this invention is to provide moldings composed of biodegradable resins that are superior in various properties such as extrusion workability, mechanical properties and heat resistance, in particular, resin compositions having both biodegradability and heat resistance after molding.

As described above, the application of biotechnological approaches to the production of resin compositions and moldings makes it possible to produce novel resin compositions and moldings, which have been hard to realize by conventional synthetic-organic-chemistry approaches. Further, the application of biotechnological approaches often makes it possible to accomplish in one step a production process, which conventional synthetic-organic-chemistry approaches have done in more than one step. Thus, the application of biotechnological approaches is expected to produce various effects such as simplification of production processes, lowering of production costs and reduction of the time required for production processes. The application of biotechnological approaches also makes possible reduction in amount of organic solvents, acids, alkalis and surfactants used, establishment of moderate reaction conditions, and synthesis of resins from non-petroleum materials and low-purity materials. This allows the realization of an environmental load reduction and resource-recycle type of synthesis process.

The above described resin composition synthesis, which uses low-purity materials, will be described in further detail. In biotechnological synthesis process, generally substrate specificity of enzymes, as catalysts, is high; therefore, a desired reaction is allowed to proceed selectively even with low-purity materials. This means that resin wastes and recycling resin materials can also be expected as materials for resin compositions.

Another object of this invention is to provide a binder resin that includes the polyhydroxyalkanoate type of polyester, that is biodegradable and therefore capable of highly contributing to the conservation of the natural environment, that makes easy deinking in conventional deinking processes using an alkali and therefore promotes recycling of copying paper, and that satisfies various requirements for a toner, such as carrier spent, fog, charge stability, durability, storage stability, grindability and cost, a toner for developing electrostatic charge images that includes the above binder resin, and image forming method and apparatus using the toner.

In addition, the present invention provides a negatively charged charge controlling agent containing this polyhydroxyalkanoate type polyester, being more contributable to preservation of environments and the like, and having high performance (high charge level, quick start of charge, excellent stability with time, and high environmental stability) and improved dispersibility in the aspect of functionality, an electrostatic latent image developing toner containing the charge controlling agent, and an image formation method and an image forming apparatus using the electrostatic latent image developing toner.

DISCLOSURE OF THE INVENTION

After intensive research effort for solving the above described problems, the inventors of this invention have found that a polyhydroxyalkanoate type polyester having a unit that includes an aromatic ring substituted with a carboxyl group, a functional group used for various applications, specifically a PHA synthesized by microorganisms and having a 3-hydroxy-ω-(4-carboxyphenyl)alkanoic acid unit can be produced by reacting a polyhydroxyalkanoate type polyester including a unit that has a vinylphenyl or methylphenyl structure with various compounds that serve the objectives.

The inventors have also found that the above PHA has a high melting point (hereinafter sometimes referred to as Tm) and a high glass transition point (hereinafter sometimes referred to as Tg) and the use of the PHA in a resin composition provides a resin composition superior in extrusion workability, mechanical properties and heat resistance and having biodegradability.

The inventors have also found that the use of the PHA in a binder resin for toners for electrophotographic use makes easy deinking in the deinking process conventionally performed using an alkali, promotes recycling of used copying paper, and satisfies various requirements for a toner, such as carrier spent, fog, charge stability, durability, storage stability, grindability and costs.

In addition, the inventors have found that the above PHA has excellent characteristics as a charge controlling agent, and has a high level of safety for human bodies and environments, and that a significant effect can be exhibited when an electrostatic latent image developing toner (hereinafter referred to toner) containing the charge controlling agent and the toner are used in an image forming apparatus having a certain development system.

The summary of this invention is as follows.

[1] A polyhydroxyalkanoate containing in a molecule thereof one or more 3-hydroxy-ω-(4-carboxyphenyl)alkanoic acid units represented by a chemical formula (1):

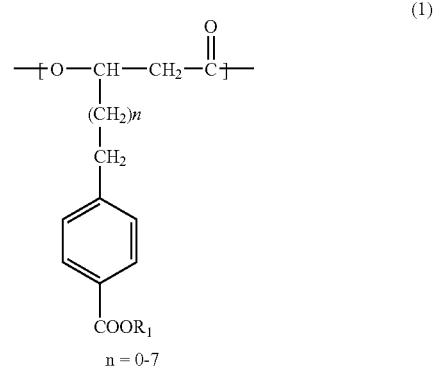

wherein n is an integer selected from 0 to 7; $R_1$ is an H, Na or K atom; and when more than one unit exists, n and $R_1$ may differ from unit to unit, respectively.

[2] A process for preparing a polyhydroxyalkanoate represented by the chemical formula (1):

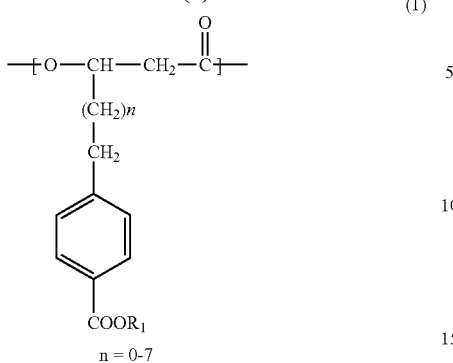

wherein n is an integer selected from the range shown in the formula; $R_1$ is an H, Na or K atom; and when more than one unit exists, n and $R_1$ may differ from unit to unit, respectively, the method is characterized in oxidization of the double bond portion of the polyhydroxyalkanoate represented by the chemical formula (16) or the methyl group portion of the polyhydroxyalkanoate represented by the chemical formula (17);

Chemical formula (16):

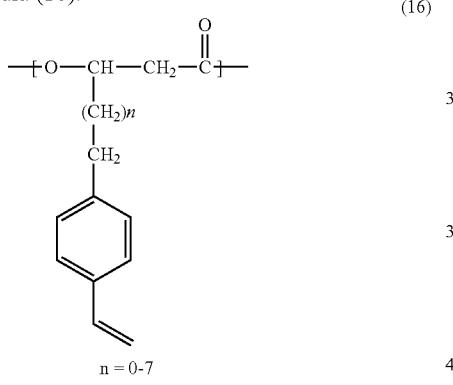

wherein n is an integer selected from 0 to 7; and when more than one unit exists, n may differ from unit to unit, Chemical formula 17:

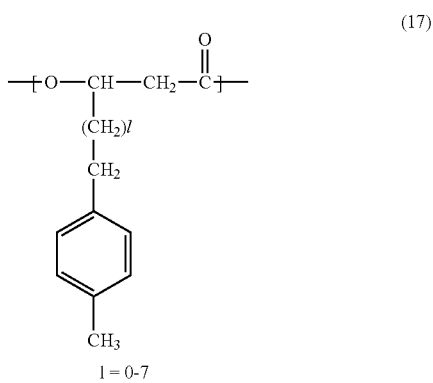

wherein l is an integer selected from 0 to 7; and when more than one unit exists, l may differ from unit to unit.

[3] A process for preparing a polyhydroxyalkanoate comprising at least both 3-hydroxy-ω-(4-carboxyphenyl)alkanoic acid unit represented by the chemical formula (1) and 3-hydroxy-ω-substituted alkanoic acid units represented by the chemical formula (3):

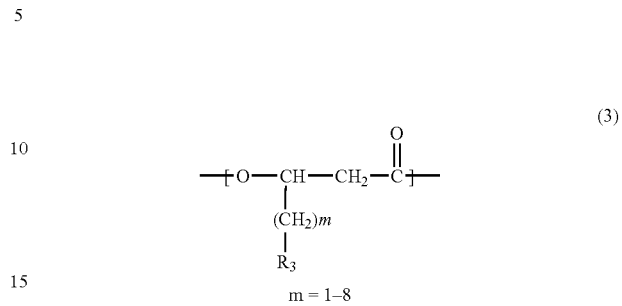

wherein m is an integer selected from the range shown in the formula; $R_3$ comprises a residue having a ring structure of either a phenyl or a thienyl-structure; and when more than one unit exists, m and $R_3$ may differ from unit to unit, respectively, or 3-hydroxy-ω-cyclohexylalkanoic acid units represented by the chemical formula (4):

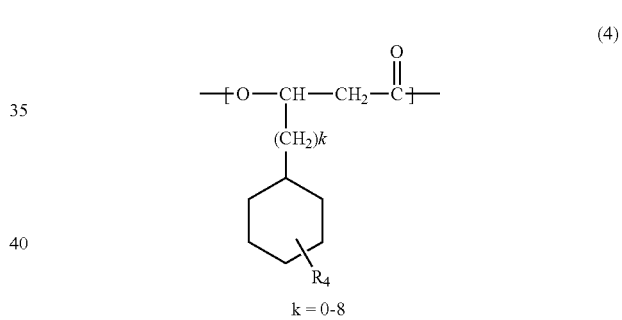

wherein $R_4$ represents a substituent on the cyclohexyl group and is an H atom, a CN group, an $NO_2$ group, a halogen atom, a $CH_3$ group, a $C_2H_5$ group, a $C_3H_7$ group, a $CF_3$ group, a $C_2F_5$ group or $C_3F_7$ group; k is an integer selected from the range shown in the formula; and when more than one unit exists, $R_4$ and k may differ from unit to unit, respectively, the process comprising the steps of:

preparing, as a raw material, a polyhydroxyalkanoate comprising at least both 3-hydroxy-ω-(4-vinylphenyl)alkanoic acid unit represented by the chemical formula (16) or 3-hydroxy-ω-(4-methylphenyl)alkanoic acid unit represented by the chemical formula (17) and 3-hydroxy-ω-substituted alkanoic acid unit represented by the chemical formula (3) or 3-hydroxy-ω-cyclohexylalkanoic acid units represented by the chemical formula (4); and oxidizing the double bond portion of the polyhydroxyalkanoate represented by the chemical formula (16) or the methyl group portion of the polyhydroxyalkanoate represented by the chemical formula (17).

[4] A resin composition comprising a resin (A) and a thermoplastic resin (B), the resin (A) being a polyhydroxyalkanoate that contains, in a polymer molecule thereof, at least one kind of unit of the 3-hydroxy-ω-(4-carboxyphenyl)alkanoic acid units represented by the chemical formula (1)

[5] A method of producing a molding, wherein the above resin composition is heat molded.

[6] A charge controlling agent for controlling a charged state of powder and granular materials, the agent comprising a polyhydroxyalkanoate that has at least one kind of unit selected from the group consisting of the 3-hydroxy-ω-(4-carboxyphenyl)alkanoic acid units represented by the chemical formula (1).

[7] A toner for developing electrostatic charge images comprising at least a binder resin, a colorant and the above charge controlling agent.

[8] A binder resin for forming a resin-based powder and granular material comprising a polyhydroxyalkanoate whose polymer molecule comprises at least one kind of unit selected from the group consisting of the 3-hydroxy-ω-(4-carboxyphenyl)alkanoic acid units represented by the chemical formula (1)

[9] A toner for developing electrostatic charge images, characterized in that it contains the above binder resin.

[10] An image forming method, comprising at least a charging step of charging an electrostatic latent image-holding member by applying voltage to a charging member from outside; an electrostatic charge image forming step of forming an electrostatic charge image on the charged electrostatic latent image-holding member; a developing step of developing the electrostatic charge image with a toner for developing electrostatic charge images to form a toner image on the electrostatic latent image-holding member; a transferring step of transferring the toner image on the electrostatic latent image-holding member to a recording medium; and a fixing step of fixing the toner image on the recording medium by heat, characterized in that the method-uses the toner for developing electrostatic charge images according to the above.

[11] An image forming apparatus, comprising at least charging means of charging an electrostatic latent image-holding member by applying voltage to a charging member from outside; electrostatic charge image forming means of forming an electrostatic charge image on the charged electrostatic latent image-holding member; developing means of developing the electrostatic charge image with a toner for developing electrostatic charge images to form a toner image on the electrostatic latent image-holding member; transferring means of transferring the toner image on the electrostatic latent image-holding member to a recording medium; and fixing means of fixing the toner image on the recording medium by heat, characterized in that the apparatus uses the toner for developing electrostatic charge images according to the above.

BEST MODE FOR CARRYING OUT THE INVENTION

[PHA]

Figure 1:
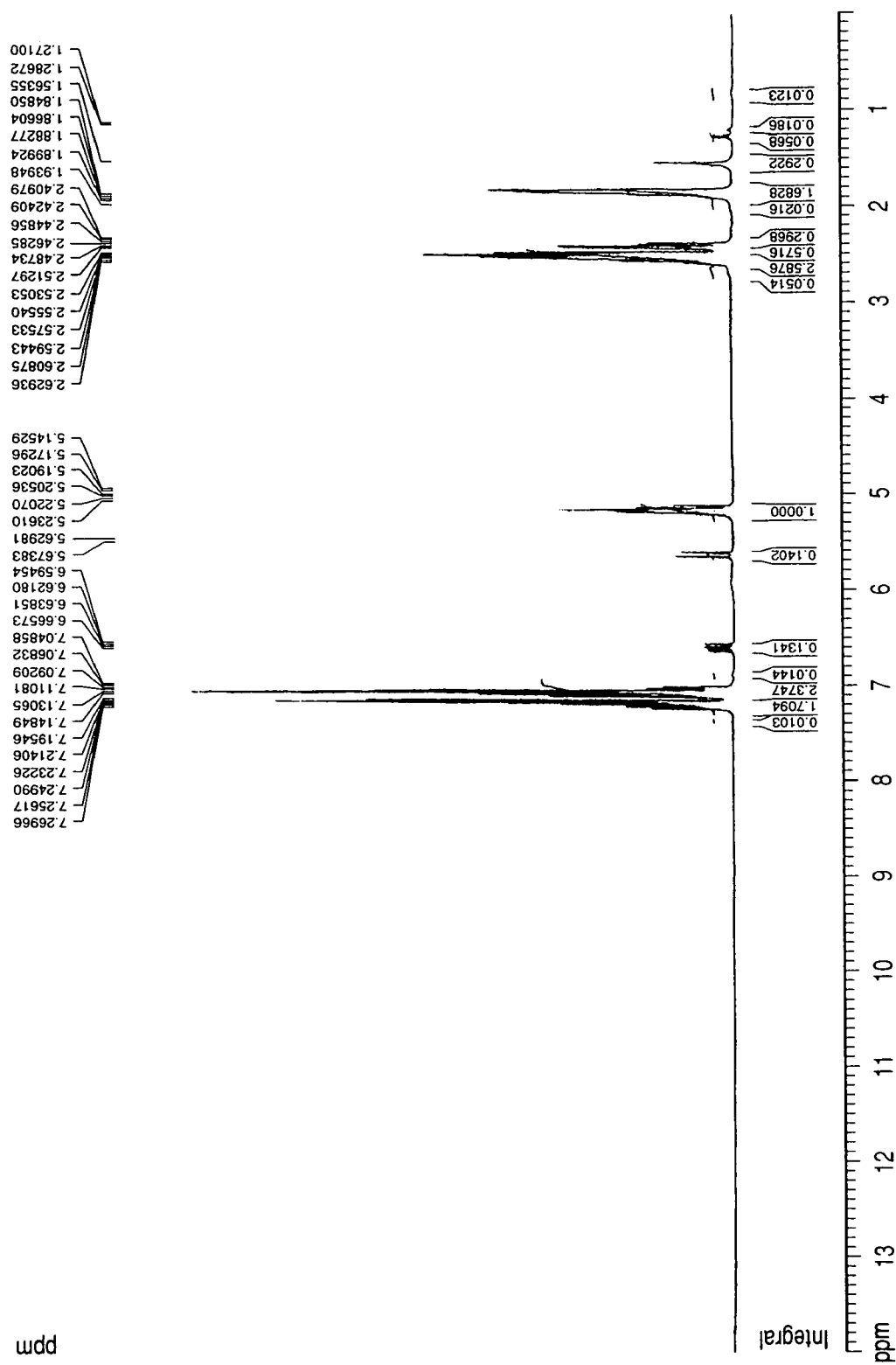
FIG. 1 is a $^1$H-NMR spectrum of the polyhydroxyalkanoate obtained by the pre-preparation 1 in Example A-1.

Polyhydroxyalkanoates used in this invention each have a fundamental skeleton as a biodegradable resin; therefore, they have outstanding characteristics in that they are melt-fablicable and can be utilized in the production of various articles, like conventional plastics, and at the same time, they are degraded by organisms and taken in the natural cycle of matter, unlike synthesized polymers derived from petroleum. As a result, they can be disposed without burning treatment, which means they are useful materials even from a viewpoint of prevention of air pollution and global warming and can be utilized as plastics that serve for the conservation of the environment.

In general, Tm and Tg are important physical properties which are related to heat resistance and mechanical strength (e.g. modulus of elasticity) of resin materials. It is said that, for example, resin materials having high Tm and Tg are superior in heat resistance and mechanical strength; conversely, resin materials having low Tm and Tg are inferior in heat resistance and mechanical strength, though they have an advantage of being easy to mold etc. Conventional PHAs mostly have relatively low Tm and Tg, therefore, there has been a limit to their extrusion workability, mechanical properties and heat resistance, and hence to their expansion in application.

When polyhydroxyalkanoates of this invention are mixed with other resins into resin compositions, the resultant resin compositions have improved physical properties, such as thermal and mechanical properties, compared with resin compositions formed using conventional mcl-PHAs or unusual-PHAs alone. As a result, they find their way into use that requires these physical properties; for example, they can be used in the relatively high-temperature (140° C. or lower) environment.

The resin compositions can also be used as raw materials for toner binders and charge controlling agents of toners for use in electrophotography, and the use of such resin compositions in the electrophotographic process can reduce the load onto the environment.

The PHAs having these desired physical properties are obtained by properly selecting culturing conditions under which microorganisms capable of synthesizing the PHAs of this invention are cultured. For example, controlling the time of incubation allows the control of the number average molecular weight of PHAs. Further, removing low molecular weight components by means of solvent extraction, reprecipitation, etc. also allows the control of the number average molecular weight of PHAs. The glass transition point and the softening point are correlated with the molecular weight of PHAs. Further, controlling the kind/composition ratio of monomer units included in PHAs also allows the control of the glass transition point and the softening point of PHAs.

Desirably, the molecular weight of PHAs is about 1000 to 10000000 in terms of number average molecular weight.

When these compounds are produced using microorganisms, the produced polyester resins are isotactic polymers consisting of R-configuration molecules alone; however, the polyester resins are not necessarily isotactic polymers, but atactic polymers can also be used as long as they can accomplish the object of this invention in respect to both physical properties and functions. Further, PHAs can also be obtained by chemical synthesis process in which lactone compounds are subjected to ring-opening polymerization using organometallic catalysts (e.g. organic catalysts containing aluminum, zinc, tin, etc.)

The polyhydroxyalkanoates including a 3-hydroxy-ω-(4-carboxyphenyl)alkanoic acid unit represented by the chemical formula (1), which this invention aims at, are produced by biosynthesizing, as a starting material, a 3-hydroxy-ω-(4-vinylphenyl)alkanoic acid unit of the chemical formula (16), which includes a carbon-carbon double bond at the end of its side chain, or a 3-hydroxy-ω-(4-methylphenyl)alkanoic acid unit of the chemical formula (17), which includes a methyl group at the end of its side chain; and oxidizing the double bond portion of the polyhydroxyalkanoate represented by the chemical formula (16) or the methyl group portion of the polyhydroxyalkanoate of the chemical formula (17).

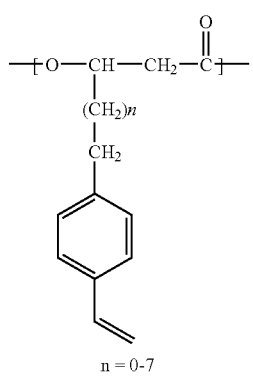

(16)

n = 0-7 wherein n is an integer selected from 0 to 7, and when more than one unit exists, n may differ from unit to unit.

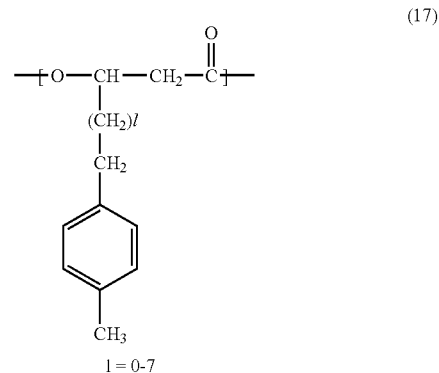

(17)

l = 0-7 wherein l is an integer selected from 0 to 7, and when more than one unit exists, l may differ from unit to unit.

The polyhydroxyalkanoates including a unit represented by the chemical formula (16) or (17), which are used as a starting material for this invention, can be prepared by, not limited to, the methods such as a microbial production process that uses microorganisms having PHA productivity described later; a plant system in which genes relating to PHA productivity are introduced; and chemical polymerization. Preferably, the microbial production process is used.

A method of preparing a polyhydroxyalkanoate including a unit represented by the chemical formula (16) or (17), as a starting material, will be described.

The above polyhydroxyalkanoate as a starting material is prepared by the method characterized by culturing the above described microorganism in a medium that contains at least one kind of alkanoic acid selected from the group consisting of ω-(4vinylphenyl)alkanoic acid represented by the chemical formula (18) and ω-(4-methylphenyl)alkanoic acid represented by the chemical formula (19).

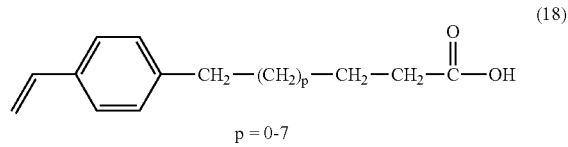

(18)

p = 0-7 wherein p is an integer selected from the range shown in the chemical formula.

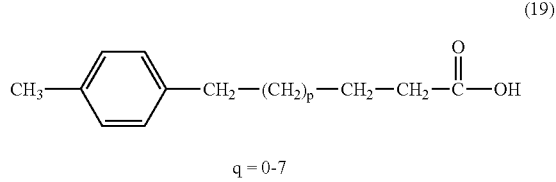

(19)

q = 0-7

<PHA Producing Strains>

The microorganism for use in the method of producing polyhydroxyalkanoate containing units each expressed by chemical formula (16) or (17) as a starting material according to the present invention may be any microorganism as long as it is a microorganism capable of producing a PHA type polyester containing 3-hydroxy-ω-(4-vinylphenyl)alkanoic acid units expressed by general chemical formula (16) or 3-hydroxy-ω-(4-meghylphenyl)alkanoic acid units expressed by general chemical formula (17) by culturing the microorganism in a culture medium containing ω-(4-vinylphenyl)alkanoic acid expressed by general chemical formula (18) or ω-(4-meghylphenyl)alkanoic acid of the general chemical formula (19). A suitable example of usable microorganisms capable of producing PHA may be a microorganism belonging to genus *Pseudomonas*. Above all, more preferable are strains which are capable of producing PHA, in particular, while having no enzyme reactivity to oxidize or epoxidized the vinyl group existing as a substituent on the phenyl group.

More specifically, among microorganisms belonging to *Pseudomonas*, more preferable species as the microorganism for use in the production method of the present invention may include *Pseudomonas cichorii, Pseudomonas putida, Pseudomonas fluorecense, Pseudomonas oleovolans, Pseudomonas aeruginosa, Pseudomonas stutzeri* and *Pseudomonas jessenii*.

Further, a more suitable strain includes, for example, *Pseudomonas cichorii* YN2 (FERM BP-7375), *Pseudomonas cichorii* H45 (FERM BP-7374), *Pseudomonas jessenii* P161 (FERM BP-7376) and *Pseudomonas putida* P91 (FERM BP-7373). These four types of strains are deposited on Nov. 20, 2000 at International Patent Organism Depositary, National Institute of Advanced Industrial Science and Technology (independent administrative corporation), AIST Tsukuba Central 6, 1-1, Higashi 1-chome, Tsukuba-shi, Ibaraki-ken 305-8566 Japan, and described in Japanese Patent Application Laid-Open No. 2001-288256 and Japanese Patent Application Laid-Open No. 2002-80751.

Further, besides the microorganisms classified as *Pseudomonas* sp., many of the strains that are classified as *Burkholderia* sp., *Aeromonas* sp. or *Comamonas* sp. and are known to produce mcl-PHA or unusual-PHA can also be applied to the PHA biosynthesis of this invention.

These microorganisms are capable of producing polyhydroxyalkanoat containing a corresponding ω-substituted-3-hydroxy-alkanoic acid as a monomer unit using as a raw material a ω-substituted-straight chain alkanoic acid substituted at the chain terminal with a six-membered ring atom group such as a substituted or unsubstituted phenyl group, a substituted or unsubstituted phenoxy group and a substituted or unsubstituted cyclohexyl group, or a ω-substituted-straight chain alkanoic acid substituted at the chain terminal with a five-membered ring atom group such as a thienyl group.

<Culture>

Intended PHAs can be produced by culturing the above described microorganisms on a medium that contains: at least a carbon source as a substrate for introducing 3-hydroxy-ω-(4-vinylphenyl)alkanoic acid unit or a 3-hydroxy-ω-(4-methylphenyl)alkanoic acid unit; a carbon source as a substrate for introducing a desired monomer unit other than 3-hydroxy-ω-(4-vinylphenyl)alkanoic acid unit or 3-hydroxy-ω-(4-methylphenyl)alkanoic acid unit; and a carbon source for propagation of microorganisms. Generally, the PHAs thus produced are isotactic polymers that consist of R-configuration molecules alone.

In the production method of the present invention, any culture medium may be used in the process of culturing a microorganism as long as it is an inorganic salt culture medium containing a phosphate and a nitrogen source such as an ammonium salt or nitrate. In the process of producing PHA in the microorganism, the productivity of PHA may be improved by adjusting the concentration of the nitrogen source.

In addition, nutrients such as an yeast extract, polypeptone and meat extract can be added to the culture medium as a substrate for promoting the propagation of the microorganism. That is, peptides may be added as an energy source and a carbon source in the form of nutrients such as an yeast extract, polypeptone and a meat extract.

Alternatively, the culture medium may contain saccharides, for example, aldoses such as glyceroaldehyde, erythrose, arabinose, xylose, glucose, galactose, mannose and fructose, alditols such as glycerol, erythritol and xylitol, aldonic acids such as gluconic acid, uronic acids such as glucuronic acid and galacturonic acid, and disaccharides such as maltose, sucrose and lactose as an energy source and carbon source consumed for propagation of the microorganism.

Instead of the above described saccharides, organic acids or salts thereof, more specifically organic acids involved in the TCA cycle and organic acids derived from the TCA cycle by a biochemical reaction of a few steps, or water soluble salts thereof may be used. As the organic acid or salt thereof, hydroxycarboxylic acids and oxocarboxylic acids such as pyruvic acid, oxalacetic acid, citric acid, isocitric acid, ketoglutaric acid, succinic acid, fumaric acid, malic acid and lactic acid or water soluble salts thereof can be used. Alternatively, amino acids or salts thereof, for example amino acids such as asparatic acid and glutamic acid or salts thereof can be used. When the organic acid or salt thereof is added, it is more preferable that one or more types are selected from a group consisting of pyruvic acid, oxalacetic acid, citric acid, isocitric acid, ketoglutaric acid, succinic acid, fumaric acid, malic acid, lactic acid and salts thereof, and added to the culture medium and dissolved therein. Alternatively, when the amino acid or salt thereof is added, it is more preferable that one or more types are selected from a group consisting of asparaginic acid, glutamic acid and salts thereof, and added to the culture medium and dissolved therein. At this time, as required, all or part thereof can be added in the form of a water soluble salt to be dissolved uniformly without affecting the pH of the culture medium.

It is desirable that the concentration of the above coexisting substrate added to the culture medium as a carbon source for growth of the microorganism and energy source for production of polyhydroxyalkanoate is usually selected so that it is in the range of from 0.05 to 5% (w/v), more preferably 0.2 to 2% (w/v) per culture medium. That is, for peptides, yeast extracts, organic acids or salts thereof, amino acids or salts thereof, and saccharides, which are used as the above coexisting substrates, one or more types thereof may be added, and, it is desirable that the total concentration of these added substrates is with in the above described range of total concentrations.

As substrates for producing an intended polyhydroxyalkanoate, any carbon sources may be used as long as they can be converted into the above units by the microorganisms used; however, ω-(vinylphenyl)alkanoic acid having the general formula (18) is preferably used, more specifically, 4-(4-vinylphenyl)butyric acid, 5-(4-vinylphenyl)valeric acid, 6-(4-vinylphenyl)hexanoic acid and 7-(4-vinylphenyl)heptanoic acid can be preferably used. Of the above carbon sources, 4-(4-vinylphenyl)butyric acid, 5-(4-vinylphenyl)valeric acid and 6-(4-vinylphenyl)hexanoic acid are preferable in terms of their thermal properties. Or ω-(methylphenyl)alkanoic acid having the general formula (19) is preferably used, more specifically, 4-(4-methylphenyl)butyric acid, 5-(4-methylphenyl)valeric acid, 6-(4-methylphenyl)hexanoic acid and 7-(4-methylphenyl)heptanoic acid can be preferably used. Of the above carbon sources, 4-(4-methylphenyl)butyric acid, 5-(4-mthylphenyl)valeric acid and 6-(4-methylphenyl)hexanoic acid are preferably used in terms of their thermal properties. Preferably the content of these substrates is selected to fall in the range of 0.01% to 1% (w/v) per medium and more preferably in the range of 0.02% to 0.2% (w/v).

As inorganic salt media applicable to the production method of this invention, any inorganic salt media, can be used as long as they contain components such as a phosphorus source (e.g. phosphates) and a nitrogen source (e.g. ammonium salts and nitrates) that support growth of the microorganism. They include, for example, MSB medium, E medium and M9 medium.

As an example, the composition of an inorganic salt medium (M9 medium), which is used in the examples described later, is shown below.

<Composition of M9 Culture Medium>
$Na_2HPO_4$: 6.3
$KH_2PO_4$: 3.0
$NH_4Cl$: 1.0
NaCl: 0.5
(by g/L, pH=7.0).

Further, for ensuring satisfactory propagation of cells and associated improvement of productivity of PHA, essential trace elements such as essential trace metal elements should be added in an appropriate amount to an inorganic salt culture medium such as the above described M9 culture medium, and it is very effective to add a solution of trace components to about 0.3% (v/v), of which composition is shown below. The addition of such a trace component solution supplies trace metal elements for use in propagation of the microorganism. (Composition of trace component solution) nitrilotriacetic acid: 1.5; $MgSO_4$: 3.0; $MnSO_4$: 0.5; NaCl: 1.0; $FeSO_4$: 0.1; $CaCl_2$: 0.1; $CoCl_2$: 0.1; $ZnSO_4$: 0.1; $CuSO_4$: 0.1; $AlK(SO_4)_2$: 0.1; $H_3BO_3$: 0.1; $Na_2MoO_4$: 0.1; $NiCl_2$: 0.1 (g/L).

Any temperature at which microorganism strains to be used can suitably be propagated may be selected as a culture temperature, and an appropriate. temperature is usually in the range of from about 15 to 37° C., more preferably from about 20 to 30° C.

Any culture method such as liquid culture and solid culture may be used for the culture as long as it allows propagation of microorganism and production of PHA. In addition, any type of culture method such as batch culture, fed-batch culture, semi-continuous culture and continuous culture may be used. Forms of liquid batch culture include a method of supplying oxygen by shaking the microorganism in a shaking flask, and a method of supplying oxygen by aeration-agitation using a jar fermenter.

For the method of making the microorganism produce and accumulate PHA, a two-step culture method in which the microorganism is cultured by two steps may be adopted other than the one-step culture method in which the microorganism is cultured in an inorganic salt culture medium containing a phosphate and a nitrogen source such as an ammonium salt or a nitrate with the substrate added therein in a predetermined concentration as described above. In this two-step culture method, the microorganism is once propagated sufficiently in the inorganic salt culture medium containing a phosphate and a nitrogen source such as an ammonium salt or a nitrate with a substrate added therein in a predetermined concentration as a primary culture, and thereafter cells obtained by the primary culture are transferred to a culture medium containing the substrate in a predetermined concentration where the amount of nitrogen source such as ammonium chloride is limited, and are further cultured as a secondary culture, thereby making the microorganism produce and accumulate PHA. Use of this two-step culture method may improve the productivity of desired PHA.

Generally, a produced PHA type polyester has reduced water solubility because of the presence of hydrophobic atomic groups such as a 4-vinylphenyl group of a 3-hydroxy-ω-(4-vinylphenyl)alkanoic acid unit or a 4-meghylphenyl group of a 3-hydroxy-ω-(4-methylphenyl)alkanoic acid unit in the side chain, and is accumulated in cells producing PHA, and can easily be separated from the culture medium by culturing cells and collecting the cells producing and accumulating the desired PHA type polyester. After the collected cells are washed and dried, the desired PHA type polyester can be collected.

In addition, polyhydroxyalkanoate is usually accumulated in cells of such a microorganism capable of producing PHA. For the method of collecting desired PHA from these microorganism cells, a method that is usually used may be adopted. For example, extraction with an organic solvent such as chloroform, dichloromethane and acetone is most convenient. Other than the above described solvents, dioxane, tetrahydrofuran and acetonitrile may be used. In addition, in a working environment in which use of any organic solvent is not preferred, a method in which in stead of solvent extraction, any one of a treatment by surfactants such as SDS, a treatment by enzymes such as lysozyme, a treatment by chemicals such as hypochlorites, ammonium and EDTA, an ultrasonic disruption method, a homogenizer method, a pressure disruption method, a bead impulse method, a grinding method, a pounding method and a freeze-thaw method is used to physically disrupt microorganism cells, followed by removing cell components other than PHA to collect PHA may be adopted.

When producing the PHAs of this invention using microorganisms, the PHAs can include monomer units other than the above described 3-hydroxy-ω-(4-carboxyphenyl)alkanoic acid units; however, the PHAs should be designed taking into consideration the functionality, physical properties, etc. of polymers required. In general, the object of this invention is expected to be sufficiently accomplished by allowing the PHAs to include the above described 3-hydroxy-ω-(4-carboxyphenyl)alkanoic acid units; however, if a delicate control of the functionality and the physical properties of PHAs is desired, PHAs can be composed of more kinds of monomer units. Specifically, if at least one kind of monomer unit of ω-substituted alkanoic acid compound represented by the chemical formula (20) or at least one kind of monomer unit of ω-cyclohexyl alkanoic acid compound represented by the chemical formula (21) is allowed to coexist with a substrate for producing an intended polyhydroxyalkanoate, that is, at least one kind of monomer unit selected from the group consisting of ω-(4-vinylphenyl)alkanoic acid represented by the chemical formula (18) and ω-(4-methylphenyl)alkanoic acid represented by the chemical formula (19) during the culture, a polyhydroxyalkanoate can be produced which includes a 3-hydroxy-ω-substituted alkanoic acid unit represented by the chemical formula (3) or a 3-hydroxy-ω-cyclohexyl alkanoic acid unit represented by the chemical formula (4), besides a 3-hydroxy-ω-(4-vinylphenyl)alkanoic acid unit represented by the chemical formula (16) or a 3-hydroxy-ω-(4-methylphenyl)alkanoic acid unit represented by the chemical formula (17). In this case, the contents of at least one monomer unit selected from the group consisting of ω-(4-vinylphenyl)alkanoic acid represented by the chemical formula (18) and ω-(4-methylphenyl)alkanoic acid represented by the chemical formula (19), at least one kind of monomer unit of ω-substituted alkanoic acid compound represented by the chemical formula (20), and at least one kind of monomer unit of ω-cyclohexyl alkanoic acid compound represented by the chemical formula (21) are preferably selected to each fall in the range of 0.01% to 1% (w/v) per medium and more preferably in the range of 0.02% to 0.2% (w/v) per medium:

[Chemical Formula 20]

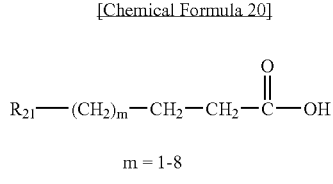

(20)

$m = 1-8$ wherein m is an integer selected from the range shown in the formula; $R_{21}$ includes a ring structure of a phenyl or thienyl structure and has any one chemical formula selected from the group consisting of the following chemical formula (5) to (15):

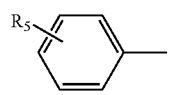

(5)

wherein $R_5$ represents a substituent on the aromatic ring and is an H atom, a halogen atom, a CN group, an $NO_2$ group, a $CH_3$ group, a $C_2H_5$ group, a $C_3H_7$ group, a $CH=CH_2$ group, $COOR_6$ ($R_6$ represents any one of H, Na and K atoms), a $CF_3$ group, a $C_2F_5$ group or a $C_3F_7$ group; and when more than one unit exists, $R_5$ may differ from unit to unit,

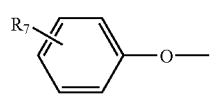

(6)

wherein $R_7$ represents a substituent on the aromatic ring and is an H atom, a halogen atom, a CN group, an $NO_2$ group, a $CH_3$ group, a $C_2H_5$ group, a $C_3H_7$ group, an $SCH_3$ group, a $CF_3$ group, a $C_2F_5$ group or a $C_3F_7$ group; and when more than one unit exists, $R_7$ may differ from unit to unit,

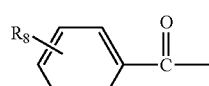

(7)

wherein $R_8$ represents a substituent on the aromatic ring and is an H atom, a halogen atom, a CN group, an $NO_2$ group, a $CH_3$ group, a $C_2H_5$ group, a $C_3H_7$ group, a $CF_3$ group, a $C_2F_5$ group or a $C_3F_7$ group; and when more than one unit exists, $R_8$ may differ from unit to unit,

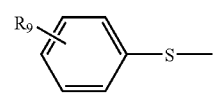

(8)

wherein $R_9$ represents a substituent on the aromatic ring and is an H atom, a halogen atom, a CN group, an $NO_2$ group, a $COOR_{10}$, an $SO_2R_{11}$ ($R_{10}$ represents any one of an H atom, an Na atom, a K atom, a $CH_3$ group and a $C_2H_5$ group and $R_{11}$ represents any one of an OH group, an ONa group, an OK group, a halogen atom, an $OCH_3$ group and $OC_2H_5$ group), a $CH_3$ group, a $C_2H_5$ group, a $C_3H_7$ group, a $(CH_3)_2$—CH group or a $(CH_3)_3$—C group; and when more than one unit exists, $R_9$ may differ from unit to unit,

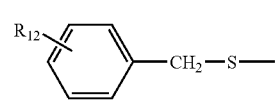

(9)

wherein $R_{12}$ represents a substituent on the aromatic ring and is an H atom, a halogen atom, a CN group, an $NO_2$ group, a $COOR_{13}$, an $SO_2R_{14}$ ($R_{13}$ represents any one of an H atom, an Na atom, a K atom, a $CH_3$ group and a $C_2H_5$ group and $R_{14}$ represents any one of an OH group, an ONa group, an OK group, a halogen atom, an $OCH_3$ group and $OC_2H_5$ group), a $CH_3$ group, a $C_2H_5$ group, a $C_3H_7$ group, a $(CH_3)_2$—CH group or a $(CH_3)_3$—C group; and when more than one unit exists, $R_{12}$ may differ from unit to unit,

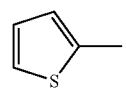

(10)

the chemical formula (11) is 2-thienylsulfanil group represented by

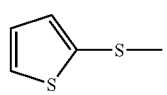

(11)

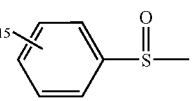

(12)

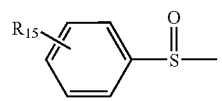

(13)

wherein $R_{15}$ represents a substituent on the aromatic ring and is an H atom, a halogen atom, a CN group, an $NO_2$ group, a $COOR_{16}$, an $SO_2R_{17}$ ($R_{16}$ represents any one of an H atom, an Na atom, a K atom, a $CH_3$ group and a $C_2H_5$ group and $R_{17}$ represents any one of an OH group, an ONa group, an OK group, a halogen atom, an $OCH_3$ group and $OC_2H_5$ group), a $CH_3$ group, a $C_2H_5$ group, a $C_3H_7$ group, a $(CH_3)_2$—CH group or a $(CH_3)_3$—C group; and when more than one unit exists, $R_{15}$ may differ from unit to unit, (14)

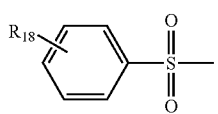

wherein $R_{18}$ represents a substituent on the aromatic ring and is an H atom, a halogen atom, a CN group, an $NO_2$ group, a $COOR_{19}$, an $SO_2R_{20}$ ($R_{19}$ represents any one of an H atom, an Na atom, a K atom, a $CH_3$ group and a $C_2H_5$ group and $R_{20}$ represents any one of an OH group, an ONa group, an OK group, a halogen atom, an $OCH_3$ group and $OC_2H_5$ group), a $CH_3$ group, a $C_2H_5$ group, a $C_3H_7$ group, a $(CH_3)_2$—CH group or a $(CH_3)_3$—C group; and when more than one unit exists, $R_{18}$ may differ from unit to unit, and (15)

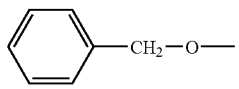

and when more than one unit exists, $R_{21}$ may differ from unit to unit;

[Chemical Formula 21]

(21)

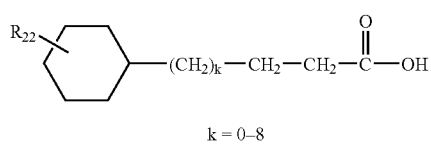

k = 0–8 wherein $R_{22}$ represents a substituent on the cyclohexyl group and is an H atom, a CN group, an $NO_2$ group, a halogen atom, a $CH_3$ group, a $C_2H_5$ group, $C_3H_7$ group, $CF_3$ group, $C_2F_5$ group or a $C_3F_7$ group; k is an integer selected from the range shown in the formula.

Further, copolymers including other 3-hydroxy alkanoic acid units can also be synthesized. Such monomer units include, for example, 3-hydroxy alkanoic acid units that constitute mcl-PHA, such as 3-hydroxy hexanoic acid unit, 3-hydroxy heptanoic acid unit, 3-hydroxy otanoic acid unit, 3-hydroxy nonanoic acid unit, 3-hydroxy decanoic acid unit, 3-hydroxy dodecanoic acid unit and 3-hydroxy tetranoic acid unit. A PHA can include more than one of these monomer units, which makes it possible to control the physical properties of PHAs and impart a plurality of functions to the same utilizing the properties of each monomer unit and each functional group included in the PHAs, and in addition, to develop novel functions utilizing the interaction among the functional groups.

<Synthesis of PHA of the Invention by Oxidation Reaction>

Polyhydroxyalkanoates represented by the chemical formula (1), which this invention aims at, are produced by using, as starting materials, polyhydroxyalkanoates that include 3-hydroxy-ω-(4-vinylphenyl)alkanoic acid unit represented by the chemical formula (16) or a 3-hydroxy-ω-(4-methylphenyl)alkanoic acid unit represented by the chemical formula (17) and oxidizing the double bond portion or the methyl group portion of the same. In the above oxidation reaction of this invention, when $R_3$ of the units represented by the chemical formula (3) is a residue represented by the chemical formula (8), the sulfide bond of the residue may sometimes be oxidized into a sulfoxide or a sulfon.

Examples of known methods of oxidizing a carbon-carbon double bond or a methyl group into carboxylic acid using an oxidizing agent are: a method using permanganate[47]; a method using bichromate[48]; a method using periodate[49]; a method using a nitrate[30]; and a method using ozone[50]. And as to polyhydroxyalkanoates, a method is reported[45] in which the carbon-carbon double bond at the end of polyhydroxyalkaniate side chain is oxidized under acid conditions using potassium permanganate as an oxidizing agent, to obtain carboxylic acid. In this invention, the same method can be used.

Preferred oxidizing agents used in this invention are, not limited to, permanganates. Of permanganates, potassium permanganate is generally used as an oxidizing agent. The amount of permanganate used should be usually 1 mol equivalent or more per mol of unit represented by the chemical formula (16) or (17) and preferably 2 to 10 mol equivalent, since oxidation reaction proceeds stoichiometrically.

To allow a reaction system to be under acid conditions, various inorganic acids and organic acids, such as sulfuric acid, hydrochloric acid, acetic acid and nitric acid, are usually used. However, when using an acid such as sulfuric acid, nitric acid or hydrochloric acid, the ester bond of the polyhydroxyalkaniate backbone chain might be broken, causing decrease in molecular weight. Accordingly, acetic acid is preferably used. The amount of acid used is usually in the range of 0.2 to 2000 mol equivalent per mol of unit represented by the chemical formula (16) or (17) and preferably in the range of 0.4 to 1000 mol equivalent. The amount less than 0.2 mol equivalent gives the carboxyl acid in a low yield, whereas the amount more than 1000 mol equivalent gives the degradation products, as by-product, by the acid; therefore neither case are preferable. In order to accelerate the reaction, crown ether can also be used. In this case, crown ether and permanganate form a complex, which increases the reactivity. As the crown ether, dibenzo-18-crown-6-ether, dicyclo-18-crown-6-ether or 18-crown-6-ether is generally used. The amount of crown ether used is usually in the range of 0.005 to 2.0 mol equivalent per mol of permanganate and preferably in the range of 0.01 to 1.5 mol equivalent.

As a solvent used in the oxidation reaction of this invention, any solvents can be used as long as they are inactive in the oxidation reaction. For example, water; acetone; ethers such as tetrahydrofuran and dioxane; aromatic hydrocarbons such as benzene, toluene and xylene; aliphatic hydrocarbons such as hexane and heptane; and hydrocarbon halides such as methyl cloride, dicloromethane and chloroform can be used. Of these solvents, hydrocarbon halides, such as methyl chloride, dichloromethane and chloroform, and acetone are preferable, taking into consideration the solubility of polyhydroxyalkanoates.

In the above described oxidation reaction, a polyhydroxyalkanoate including a unit represented by the chemical formula (16) or (17), a permanganate and an acid may be introduced into a solvent at a time from the beginning and reacted together, or they may be added to the reaction system one by one continuously or intermittently to be reacted. Or first a permanganate alone is dissolved or suspended in a solvent, followed by continuous or intermittent addition of a polyhydroxyalkanoate and an acid to the reaction system, or first a polyhydroxyalkanoate alone is dissolved or suspended in a solvent, followed by continuous or intermittent addition of a permanganate and an acid to the reaction system. Further, first a polyhydroxyalkanoate and an acid are introduced into a solvent and then a permanganate is added to the reaction system continuously or intermittently to be reacted, or first permanganate and an acid are introduced into a solvent and then polyhydroxyalkanoate is added to the reaction system continuously or intermittently, or first a polyhydroxyalkanoate and a permanganate are introduced into a solvent and then an acid is added to the reaction system continuously and intermittently to be reacted.

The reaction temperature should be usually −40 to 40° C. and preferably −10 to 30° C. The reaction time should be usually 2 to 48 hours, though it depends on the stoichiometric ratio of the unit represented by the chemical formula (16) or (17) to the permanganate and the reaction temperature.

When using a polyhydroxyalkanoate that includes a 3-hydroxy-ω-substituted alkanoic acid unit represented by the chemical formula (3) or a 3-hydroxy-ω-cyclohexyl alkanoic acid unit represented by the chemical formula (4), besides a 3-hydroxy-ω-(4-vinylphenyl)alkanoic acid unit represented by the chemical formula (16) or a 3-hydroxy-ω-(4-methylphenyl)alkanoic acid unit represented by the chemical formula (17), the reaction can be conducted under the same conditions.

The polyhydroxyalkanoate polymer produced by the process of this invention using, as an intermediate material, a polyhydroxyalkanoate synthesized by microorganisms includes in the molecule a unit having a carboxyl group. This structure strongly stimulates the localization of electrons in the molecule at the end of such a unit, and the electrical characteristics may differ from conventional polyhydroxyalkanoates significantly. Further, due to such localization of electrons, the behavior of the polyhydroxyalkanoate polymer to a solvent differs from that of conventional polyhydroxyalkanoates. For example, the polyhydroxyalkanoate polymer of this invention is soluble even in a polar solvent such as dimethylformamide (DMF). Further, due to its thermal characteristics, in particular, the remarkably increased glass transition temperature resulting from the hydrogen bond, it finds its way into a wide. variety of applications.

[Resin Composition and Molding]

The PHA obtained by the above described process is properly molded and processed, depending on the situation, to moldings having desired shapes.

Although the PHA alone can be used as a biodegradable resin composition, it can also be used in the form of a blend with other resin ingredients, as long as the blend ensures desired properties. As for the mixing ratio of PHA to thermoplastic resins, it is preferable that the content by weight of the PHA is larger than that of the thermoplastic resins. The practical examples of the resin ingredients are polyester-based resins, polystyrene-based resins, polypropylene-based resins, polyethylene terephthalate-based resins, polyurethane-based resins, polyvinyl-based resins and polyamide-based resins. Of the above resin ingredients, polyester-based resins such as poly-ε-caprolactone and polylactic acid provide resin compositions superior in biodegradability; however, the use of other resin ingredients such as polystyrene also enables the improvement in biodegradability of the resin composition when the process of this invention is used. This is possibly because, in the moldings formed of the blends of the PHA of this invention and the above resin ingredients, since the PHA is rapidly decomposed in the natural environment, the collapse of the moldings is accelerated, which makes the blended resin ingredients easy to subject to photodegradation and biodegradation.

Additives for resin can be added to the resin compositions as the need arises. Examples of additives for resin are plasticizers, thermal stabilizers, lubricants, anti-blocking agents, nucleators, photodegrading agents, biodegradation accelerators, anti-oxidants, ultraviolet stabilizers, antistatic agents, flame retarders, anti-stick agents, anti-fungus agent, deodorants, fillers, colorants and the mixtures thereof.

The plasticizers include, for example, aliphatic dibasic ester, phthalate ester, hydroxy polyvalent carboxylate ester, polyester-based plasticizer, fatty ester, epoxy-based plasticizer and the mixtures thereof. The amount of the plasticizer added differs depending on its applications, but it is preferably in the range of 3 to 30 parts by mass per 100 parts of resin composition.

The thermal stabilizers include, for example, aliphatic carboxylate, specifically sodium salt, calcium salt, aluminum salt, barium salt, magnesium salt, manganese salt, iron salt, zinc salt, lead salt, silver salt and copper salt of lactic acid, hydroxy butyric acid and the like. The amount of the stabilizer added is preferably in the range of 0.5 to 10 parts by mass per 100 parts of resin composition.

The lubricants applicable include, for example, fatty ester, hydrocarbon resin, paraffin, higher fatty acid, oxyfatty acid, fatty acid amide, alkylenebisfatty acid amide, aliphatic ketone, fatty acid lower alcohol ester, fatty acid polyhydric alcohol ester, fatty acid polyglycol ester, aliphatic alcohol, polyhydric alcohol, polyglycol, polyglycerol, metallic soap, modified silicone and the mixtures thereof.

The amount of the lubricant added is preferably in the range of 0.05 to 5 parts by mass per 100 parts of resin composition.

The photodegrading agents include, for example, photoexciting agents such as benzoins, benzoinalkyl ethers, benzophenones such as benzophenone and 4,4-bis(dimethylamino)benzophenone and the derivatives thereof, acetophenones such as acetophenone and α,α-diethoxyacetophenone and the derivatives thereof, quinones, thioxanthones, and phthalocyanine; anatase type of titanium oxide; ethylene-carbon monooxide copolymer; and sensitizers such as aromatic ketone and metallic salt. Two or more of these photodegrading agents can be used in the mixed form.

The biodegradation accelerators include: for example, organic acids such as glycolic acid, lactic acid, citric acid, tartaric acid, malic acid, oxalic acid, malonic acid, succinic acid, succinic anhydride and glutaric acid; and coconut shell activated carbon. Two or more of these biodegradation accelerators can be used in the mixed form.

In the resultant resin composition containing the PHA as a main ingredient, desirably its Mn is about 1,000 to 1,000,000.

The resin composition of this invention can be used for applications, such as mechanical parts, electric/electronic components, various kinds of heat appliances, packaging containers and parts for vehicles, where the resin compositions containing conventional mcl-PHA or unusual-PHA, as a main ingredient, have had limitations due to their thermal characteristics.

For example, packaging containers are produced by any one method of expansion extrusion, non-axially oriented sheet extrusion, biaxially oriented sheet extrusion, injection blow molding and injection molding, and if necessary, through post-forming process. In the expansion extrusion, for example, gas as a foaming agent is impregnated into a molten resin and the resin is extruded into a formed sheet, before the resin is formed into trays for perishable foods, bowl-shaped or square containers for instant noodles, etc. Packaging containers for foods, which this invention aims at, can be obtained by post-forming the resultant foamed sheet into desired shapes. Lunch boxes and the lids thereof and food packages are also produced by first extruding a molten resin into a sheet, through or not through an drawing step, and then post-forming the extruded sheet into intended shapes. The containers for foods and cups obtained by injection blow molding and injection molding are also classified into the above described packaging containers for foods.

[Application to Toner]

The polyhydroxyalkanoate of this invention has, for example, an application in toners for developing electrostatic charge images and the image forming process using the same. Specifically, the polyhydroxyalkanoate can be used as a material for a binder resin which constitutes the bulk of the substantial part of a toner other than the colorants, and in addition, as a charge controlling agent which is added to a toner internally or externally.

In other words, this invention provides a binder resin and/or a charge controlling agent, and in addition, a toner for developing electrostatic charge images that contains the binder resin and/or the charge controlling agent. Furthermore, this invention is an image forming method including a charging step of charging an electrostatic latent image-holding member uniformly by applying voltage to a charging member from the outside; a developing step of forming a toner image on the electrostatic latent image-holding member; a transferring step of transferring the toner image on the electrostatic latent image-holding member to a transfer medium through or not through an intermediate transfer medium; and a heat fixing step of fixing the toner image on the transfer medium by heat. Further, this invention is an image forming apparatus including means corresponding to the steps of the above image forming method, that is, charging means, developing means, transferring means and heat fixing means.

<Binder Resin>

Although the above described polyhydroxyalkanoate may be used as it is as binder resin of this invention, the binder resin of this invention may further include other thermoplastic resins, in particular, biodegradable resins such as polycaprolactone and polylactic acid. PHAs with number average molecular weight of about 300000 or less are preferable, because they are highly compatible with each of polycaprolactone and polylactic acid and provide colorless and clear molten polymer blends. On the other hand, PHAs with number average molecular weight of 500000 or more are not so highly compatible with each of polycaprolactone and polylactic acid and the hue of the resultant molten polymer blends is not good. However, even in this case, if the molecular weight of PHAs is decreased to 300000 or less by mixing the PHAs with such biodegradable resins under high shear force, the compatibility is improved and colorless and clear molten polymer blends can be obtained.

The number average molecular weight of the binder resin of this invention is preferably 2,000 or more and 300,000 or less and the glass transition point and the softening point of the same are preferably 30 to 80° C. and 60 to 170° C., respectively, from the viewpoint of expression of functions as a binder resin.

The polyhydroxyalkanoates used in this invention each have a fundamental skeleton as a biodegradable resin; therefore, they have outstanding characteristics in that they can be utilized in the production of various articles by melt processing etc., like conventional plastics, and at the same time, they are degraded by organisms and taken in the natural cycle of matter, unlike synthesized polymers derived from petroleum. As a result, they need not undergo burning treatment when disposed, which means they are useful materials even from a viewpoint of prevention of air pollution and global warming and can be utilized as plastics that enable the conservation of the environment.

PHAs are easy to hydrolyze in the presence of alkaline water. Therefore, they have an advantage of allowing toners containing colorants such as carbon black to be efficiently removed from used copying paper.

When the PHA of this invention is used in a binder resin, its glass transition point is preferably 30 to 80° C., particularly preferably 40 to 80° C. and much more preferably 50 to 70° C. If the glass transition point is lower than 30° C., the blocking resistance deteriorates, whereas if the point is 80° C. or higher, the fixing properties tend to deteriorate. The softening point of the PHA is preferably 60 to 170° C. and particularly preferably 80 to 140° C. If the softening point is lower than 60° C. or lower, the offset resistance deteriorates, whereas if the point is 170° C. or higher, the fixing temperatures tend to be high.

When the PHA of this invention is used in a binder resin, its number average molecular weight is preferably 2,000 to 300,000, more preferably 2,000 to 150,000 and particularly preferably 5,000 to 100,000. If the Mn is less than 2,000, the glass transition point is significantly lowered and the blocking resistance may sometimes deteriorate, whereas if the Mn is higher than 300,000, the viscosity at the time of melting becomes high and the low-temperature fixing properties may sometimes deteriorate.

The thermoplastic resins, which can be added to the binder resin of this invention along with the PHA, for example, polylactic acid is not only commercially available ones such as LACTY (trade name, Shimadzu Corporation), but also thermoplastic resins obtained by various kinds of polymerization processes can be suitably used. Besides, any resins in "Binder Resin" described later can also be used in the form of a blend with the PHA.

<Use as Charge Controlling Agent>

What is important in the structure of polyhydroxyalkanoates used in this invention is that it includes a carboxyphenyl structure on its side chain, i.e., it has an aromatic ring substituted with on the side chain, just like the monomer units represented by the chemical formula (1). The units having an anionic or electron attractive group are preferable to further improve the negative chargeability of charge controlling agents; in actuality, the charge controlling agent of this invention has superior negative chargeability.

Polyhydroxyalkanoate used in the present invention has good compatibility with the binder resin and excellent compatibility particularly with polyester type binder resin. The toner containing polyhydroxyalkanoate according to the present invention has a high specific charge level and is excellent in stability with time to provide clear images stably in electrostatic recording even after being stored for a long time period. PHA of the invention can be used for both black and color toners of negative chargeability because of its colorlessness and negative-electrifiability.

In addition, by properly selecting the type and composition ratio of monomer units constituting polyhydroxyalkanoate according to the present invention, wide range compatibility control is possible.

If a resin composition is selected such that the charge controlling agent is in micro-phase separation state in a toner binder, no electric continuity is formed in the toner so that electric charge can stably be maintained. In addition, polyhydroxyalkanoate according to the present invention contains no heavy metals, and therefore when the toner is produced by suspension polymerization or emulsion polymerization, polymerization inhibition due to the presence of heavy metals, as found with a metal-containing charge controlling agent, does not occur, thus making it possible to produce a toner with stability.

<Addition of PHA to Toner>

In the present invention, PHA can be added to a toner by a method of internal addition to the toner or a method of external addition to the toner. The addition amount of the internal addition is generally 0.1 to 50% by weight, preferably 0.3 to 30% by weight, and further preferably 0.5 to 20% by weight as the weight ratio of the toner binder and the charge controlling agent. If it is lower than 0.1% by weight, the improvement degree of the charging property of the toner is insignificant and thus not preferable. Whereas, if it is higher than 50% by weight, it is not preferably from an economical point of view. Further, in the case of the external addition, the weight ratio of the toner binder and the charge controlling agent is preferably 0.01 to 5% by weight, and it is particularly preferable that the compound is mechanochmically fixed on the surface of the toner. In addition, polyhydroxyalkanoate according to the present invention may be used in combination with a known charge controlling agent.

The number average molecular weight of polyhydroxyalkanoate according to the present invention in the case of using as a charge controlling agent is usually 1000 to 1000000, preferably 1000 to 300000. If it is less than 1000, the compound is completely compatible with the toner binder to make it difficult to form a discontinuous domain, resulting in an insufficient charge level, and the fluidity of the toner is adversely affected. Further, if it is higher than 1000000, dispersion in the toner becomes difficult.

The molecular weight of polyhydroxyalkanoate according to the present invention was measured by GPC (gel permeation chromatography). For the specific method of measurement by GPC, a sample was prepared by dissolving the above polyhydroxyalkanoate in chloroform or dimethylformamide (DMF) containing 0.1% by weight of LiBr. Using a similar mobile phase, the molecular-weight distribution was determined from a calibration curve of standard polystyrene resin.

In addition, in the case of using as a charge controlling agent, in the present invention, the above polyhydroxyalkanoate with the ratio (Mw/Mn) of the weight average molecular weight (Mw) to the number average molecular weight (Mn) measured as described above being in the range of from 1 to 10 are preferably used.

Polyhydroxyalkanoate to be used in the present invention as a charge controlling agent has a melting point preferably in the range of from 20 to 150° C., especially preferably from 40 to 150° C., or has no melting point but a glass transition temperature in the range of from 20 to 150° C., especially preferably from 40 to 150° C. If the foregoing melting point is lower than 20° C. or the glass transition temperature with no melting point is lower than 20° C., the fluidity and the storage property of the toner are often adversely affected. Whereas if the foregoing melting point is higher than 150° C. or the glass transition temperature with no melting point is higher than 150° C., the charge controlling agent becomes difficult to be kneaded with the toner and the charge level distribution becomes broad in many cases.

To measure the melting point Tm and the glass transition temperature Tg in this case, a high precision and internally heating input compensation type differential scanning calorimeter, for example, DSC-7 manufactured by Perkin Elmer Co., may be employed.

Regarding the toner binder and the toner of the present invention, the weight ratio of the toner binder and the charge controlling agent is generally 0.1 to 50% by weight, preferably 0.3 to 30% by weight, and more preferably 0.5 to 20% by weight. Regarding the composition ratio of the toner of the present invention, generally the foregoing charge controlling agent is in the range of from 0.1 to 50% by weight, the toner binder is in the range of from 20 to 95% by weight, and a coloring material is in the range of from 0 to 15% by weight with respect to the weight of the toner and based on the necessity, a magnetic powder (a powder of a ferromagnetic metal such as iron, cobalt, nickel and the like and a compound such as magnetite, hematite, ferrite and the like) functioning as a coloring material may be added in an amount not more than 60% by weight. Further, various additives such as a lubricant (polytetrafluoroethylene, a lower molecular weight polyolefin, an aliphatic acid or its metal salt or amide, and the like) and other charge controlling agents (metal-containing azo dye, metal salcylate, etc.) may be contained. In addition, in order to improve the fluidity of the toner, a hydrophobic colloidal silica fine powder may also be employed. The amounts of these additives are generally not more than 10% by weight on the bases of the toner weight.

In the toner of the present invention, it is preferable for at least some of the toner binder to form a continuous phase and at least some of the charge controlling agent to form discontinuous domains. As compared with the case where the charge controlling agent has complete compatibility with the toner binder without forming the discontinuous domains, the added charge controlling agent is easily exposed to the surface and effective even in a small amount. The dispersion particle diameter of the domain is preferably 0.01 to 4 µm and more preferably 0.05 to 2 µm. If it is bigger than 4 µm, the dispersibility becomes insufficient and the charge level distribution becomes broad and the transparency of the toner is deteriorated. Whereas, if the dispersion particle diameter is smaller than 0.01 µm, it becomes similar to the case where the charge controlling agent has complete compatibility with the binder without forming discontinuous domain, a large amount of the charge controlling agent is required to be added. That at least some of the foregoing charge controlling agent forms discontinuous domains and the dispersion particle size can be confirmed by observing a thin section specimen of the toner using a transmission electron microscope. In order clearly observe the interface, it is also effective to dye the toner specimen with ruthenium tetraoxide, osmium tetraoxide and the like.

Further, for the purpose of reducing the particle diameter of the discontinuous domains formed by polyhydroxyalkanoate according to the present invention, a polymer compatible with the polyhydroxyalkanoate and also with the toner binder may be added as a compatible agent. The compatibility enhancing agent may be a polymer comprising mutually graft- or block-polymerized polymer chains containing at least 50% by mol of monomers having practically similar structure to that of the constituent monomers of polyhydroxyalkanoate according to the present invention and polymer chains containing at least 50% by mol of monomers having practically similar structure to that of the toner binder. The amount of the compatible agent to be used is generally not more than 30% by weight and preferably 1 to 10% by weight, with respect to the polyhydroxyalkanoate according to the present invention.

<Other Constituent Materials>

Other constituent materials constituting the toner of the present invention will be described below. The toner for developing electrostatic charge images of this invention is composed of not only the above described binder resin and the charge controlling agent, but also colorants and other additives that are added depending on the situation.

<Binder Resin: Ingredients Other than PHA>

The toner may also include, besides the binder resin of this invention, other thermoplastic resins as binder resins. The binder resin of this invention can be used in the form of a mixture with, for example, polystyrene, polyacrylic ester, styrene-acrylic ester copolymer, polyvinyl chloride, polyvinyl acetate, polyvinylidene chloride, phenol resin, epoxy resin and polyester resin. The thermoplastic resins applicable are not limited, as long as they are the thermostatic resins usually used in the production of toners. When using, as the binder resins other than the PHA, thermoplastic resins that are not biodegradable, the mixing percentage of the binder resins other than the PHA to the total of the binder resins is preferably less than 50%. If the percentage of the binder resins other than the PHA is 50% or more, the binding of the binder resins to the paper surface becomes too strong, causing deinking more difficult. When using the toner as a biodegradable toner, it is preferable that the PHA is not used in the form of a mixture with other non-biodegradable thermoplastic resins.

When using the binder resins in combination with the charge controlling agent of this invention, binder resins not including the PHA as well as the above described mixed binder resins can also be used. In this case, any resin may be used without any particular restrictions if it is generally used for production of a toner. Also, the charge controlling agent of the present invention may previously be mixed with the binder resin to be used as a toner binder composition of the present invention having charge controlling capability before production of the toner. For example, as the binder resin, styrene-based polymers, polyester-based polymers, epoxy-based polymers, polyolefin-based polymers, and polyurethane-based polymers, and the like can be exemplified and they are used alone or while being mixed with one another.

<Other Biodegradable Plastics>

In addition, in the present invention, commercially available biodegradable plastics may be preferably used. Examples of the biodegradable plastics are "Ecostar", "Ecostar plus" (produced by Hagiwara Industries, Inc.), "Biopole" (produced by Monsanto Company), "Ajicoat" (Ajinomoto Co., Ltd.), "Placcel", "Polycaprolactone" (produced by Daicel Chem., Ind., Ltd.), "SHOWLEX", "Bionolle" (produced by Showa Denko K.K.), "Lacty" (produced by Shimadzu Corporation), "Lacea" (produced by Mitsui Chemicals, Inc.) and the like. When these resins are used as a mixture, biodegradability, the characteristics of the toner according to the present invention, will not be damaged.

Of the above biodegradable plastics, polycaprolactone (that is, polymer of $\epsilon$-caprolactone) or the above described polylactic acid are particularly preferable, because they are easily and completely decomposed by lipase and esterase and their physical properties are easy to modify by the blending or copolymerization with other resins.

<Examples of Other Resins>

The styrene-based polymers may be styrene-(meth)acrylic acid ester copolymers and copolymers of these copolymers with other monomers copolymerizable with them; copolymers of styrene with diene type monomers (butadiene, isoprene and the like) and copolymers of these copolymers with other monomers copolymerizable with them; and the like. The polyester-based polymers may be condensation polymerization products of aromatic dicarboxylic acid and aromatic diol alkylene oxide addition products and the like. The epoxy-based polymers may be reaction products of aromatic diols and epichlorohydrin and their modified products. The polyolefin-based polymers may be polyethylene, polypropylene, and copolymer chains of these polymers with monomers polymerizable with them. The polyurethane-based polymers may be addition polymerization products of aromatic diisocyanates and aromatic diol alkylene oxide addition products and the like.

Practical examples of the binder resin to be employed in combination with a charge controlling agent according to the present invention or as a mixture with the binder resin according to the present invention are polymers of the following polymerizable monomers or their mixtures or copolymerization products produced from two or more kinds of the following polymerizable monomers. Such polymers are more particularly, for example, styrene-based polymers such as styrene-acrylic acid copolymer, styrene-methacrylic acid copolymer, and the like; polyester-based polymers; epoxy-based polymers; polyolefin-based polymers; and polyurethane-based. polymers and they are preferably used.

Practical examples of the polymerizable monomers are styrene and its derivatives such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, and the like; ethylenic unsaturated monoolefins such as ethylene, propylene, butylene, isobutylene and the like; unsaturated polyenes such as butadiene and the like; vinyl halides such as vinyl chloride, vinylidene chloride, vinyl bromide, vinyl fluoride and the like; vinyl esters such as vinyl acetate, vinyl propionate, vinyl benzbate and the like; α-methylene aliphatic monocarboxylic acid esters such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, diethylaminoethyl methacrylate, and the like; acrylic acid esters such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, phenyl acrylate, and the like; vinyl ethers such as vinyl methyl ether, vinyl ethyl ether, vinyl isobutyl ether, and the like; vinyl ketones such as vinyl methyl ketone, vinyl hexyl ketone, methyl isopropenyl ketone, and the like; N-vinyl compounds such as N-vinylpyrrole, N-vinylcarbazole, N-vinylindole, N-vinylpyrrolidone and the like; vinyl naphthalenes; acrylic acid or methacrylic acid derivatives such as acrylonitrile, methacrylonitrile, acrylamide and the like; the above-described α,β-unsaturated acid esters; bibasic acid diesters; dicarboxylic acids such as maleic acid, methyl maleate, butyl maleate, dimethyl maleate, phthalic acid, succinic acid, terephthalic acid, and the like; polyols compounds such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A, polyoxyethylene-modified bisphenol A and the like; isocyanates such as p-phenylene diisocyanate, p-xylylene diisocyanate, 1,4-tetramethylene diisocyanate, and the like; amines such as ethylamine, butylamine, ethylenediamine, 1,4-diaminobenzene, 1,4-diaminobutane, monoethanolamine, and the like;

epoxy compounds such as diglycidyl ether, ethylene glycol diglycidyl ether, bisphenol A glycidyl ether, hydroquinone glycidyl ether, and the like.

<Cross-linking Agent>

In the case of producing the binder resin to be employed in combination with a charge controlling agent according to the present invention or as a mixture with the binder resin according to the present invention, based on the necessity, the following cross-linking agent may be used. Examples of a bifunctional cross-linking agent are divinylbenzene, bis(4-acryloxypolyethoxyphenyl)propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, respective diacrylates of polyethylene glycol #200, #400, #600, dipropylene glycol diacrylate, polypropylene glycol diacrylate, polyester type diacrylate (MANDA Nippon Kayaku), and those obtained by replacing these exemplified acrylates with methacrylates.

Examples of bi- or higher polyfunctional cross-linking agent are pentaerythritol triacrylate, trimethylolethane triacrylate, trimethylolpropane triacrylate, tetramethylolmethane tetraacrylate, oligoester acrylates or methacrylates, 2,2-bis(4-methacryloxy, polyethoxyphenyl)propane, diallyl phthalate, triallyl cyanurate, triallyl azocyanurate, triallyl isocyanurate, diaryl chlorendate, and the like.

<Polymerization Initiator>

In the case of producing the binder resin to be employed in combination with a charge controlling agent according to the present invention or as a mixture with the binder resin according to the present invention, the following polymerization initiators may be used based on the necessity: for example, tert-butyl peroxy-2-ethylhexanoate, cumine perpivalate, tert-butyl peroxylaurate, benzoyl peroxide, lauroyl peroxide, octanoyl peroxide, di-tert-butyl peroxide, tert-butylcumyl peroxide, dicumyl peroxide, 2,2'-azobis isobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1-bis(tert-butylperoxy)-3,3,5-trimethylcyclohexane, 1,1-bis(tert-butylperoxy)cyclohexane, 1,4-bis(tert-butylperoxycarbonyl)cyclohexane, 2,2-bis(tert-butylperoxy)octane, n-butyl 4,4-bis(tert-butylperoxy)valirate, 2,2-bis(tert-butylperoxy)butane, 1,3-bis(tert-butylperoxyisopropyl)benzene, 2,5-dimethyl-2,5-di(tert-butylperoxy)hexane, 2,5-dimethyl-2,5-di(tert-butylperoxy)hexane, 2,5-dimethyl-2,5-di(tert-butylperoxy)hexane, 2,5-dimethyl-2,5-di(benzoylperoxy)hexane, di-tert-butyldiperoxy isophthalate, 2,2-bis(4,4-di-tert-butylperoxycyclohexyl)propane, di-tert-butylperoxy-α-methylsuccinate, di-tert-butyl peroxydimethylglutarate, di-tert-butyl peroxyhexahydroterephthalate, di-tert-butyl peroxyazelate, 2,5-dimethyl-2,5-di(tert-butylperoxy)hexane, diethylene glycol bis(tert-butylperoxycarbonate), di-tert-butyl peroxytrimethyladipate, tris(tert-butylperoxy)triazine, vinyltris(tert-butylperoxy)silane and the like. Each of these compounds may be used alone or in combination. The use amount of them is generally in 0.05 parts by weight or more (preferably 0.1 to 15 parts by weight) to 100 parts by weight of monomers.

It is preferable for the combinations of the binder resin and the charge controlling agent of the present invention that the structure of the polymers of the binder resin and the polymer structure of the polymer chain of the charge controlling agent are similar to each other as much as possible. If the structure of the polymers of the binder resin and the polymer structure of the polymer chain of the charge controlling agent are considerably dissimilar to each other, the charge controlling agent tends to be dispersed insufficiently in the binder resin.

The weight ratio of the charge controlling agent of the present invention to be internally added to the binder resin is generally 0.1 to 50% by weight, preferably 0.3 to 30% by weight, and more preferably 0.5 to 20% by weight. If the weight ratio of the charge controlling agent to be internally added is lower than 0.1% by weight, the charge level becomes low and if the weight ratio is higher than 50% by weight, the charge stability of the toner is deteriorated.

<Charge Controlling Agent: Other than PHA>

As the charge controlling agent used in combination with the binder resin which uses the PHA of this invention, not only that of this invention but charge controlling agents currently in use can also be employed. Concrete examples are nigrosine-based dyes, quaternary ammonium salts and monoazo metal complex salt dyes. The amount of the charge controlling agent added can be determined taking into consideration various requirements: the charge characteristics of the binder resin; the method of producing the toner, including the amount of the colorants used and the method of dispersing the same; and the charge characteristics of other additives, and it is usually between 0.1 to 20 parts by mass per 100 parts of the binder resin and preferably 0.5 to 10 parts by mass. Inorganic particles such as metallic oxides and inorganic materials having been surface treated with the above described organic materials may also be used. These charge controlling agents may be used in the form of a mixture with the binder resin or in state they are attached onto the surface of toner particles.

<Coloring Agent>

Any coloring agent generally used for production of a toner may be used as the coloring agent composing the toner of the present invention without particular restrictions. For example, carbon black, titanium white, monoazo red pigment, disazo yellow pigment, quinacridone magenta pigment, anthraquinone dye, or the like, and any other pigment and/or dye may be used.

More specifically, in the case the toner of the present invention is used for a magnetic color toner, examples of the coloring agent to be employed are C.I. Direct Red 1, C.I. Direct Red 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4, C.I. Basic Green 6 and the like. Examples of the pigment are Chrome Yellow, Cadmium Yellow, Mineral Fast Yellow, Naple's Yellow, Naphthol Yellow S, Hansa Yellow G, Permanent Yellow NCG, Tartrazine Yellow Lake, Chrome Orange, Molybenum Orange, Permanent Orange GTR, Pyrazolone Orange, Benzidine Orange G, Cadmium Red, Permanent Red 4R, Watching Red calcium salt, Eosine Lake, Brilliant Carmine 3B, Manganese Violet, Fast Violet B, Methyl Violet Lake, Prussian Blue, Cobalt Blue, Alkali Blue Lake, Victoria Blue Lake, Phthalocyanine Blue, Fast Sky-Blue, Indanthrene Blue BC, Chrome Green, chromium oxide, Pigment Green B, Malachite Green Lake, Final Yellow Green G and the like.

In the case the toner of the present invention is used for a two-component type full color toner, the following coloring agents can be used. For example, coloring pigments for magenta toners are C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209, C.I. Pigment Violet 19, C.I. Vat Red 1, 2, 10, 13, 15, 23, 29, 35 and the like.

In the present invention, the above-exemplified pigments may be used alone, but it is more preferable that they are used in combination with dyes for improving the clearness from the aspect of the full color image quality. In such a case, the examples of usable magenta dyes are oil-soluble dyes such as C.I. Solvent Red 1, 3, 8, 23, 24, 25, 27, 30, 49, 81, 82, 83, 84, 100, 109, 121, C.I. Disperse Red 9, C.I. Solvent Violet 8, 13, 14, 21, 27, C.I. Solvent Violet 8, 13, 14, 21, 27, and C.I. Disperse Violet 1 and the like; and basic dyes such as C.I. Basic Red 1, 2, 9, 12, 13, 14, 15, 17, 18, 22, 23, 24, 27, 29, 32, 34, 35, 36, 37, 38, 39, 40, C.I. Basic Violet 1, 3, 7, 10, 14, 15, 21, 25, 26, 27, 28 and the like.

As other coloring pigments, examples of cyan coloring pigments are C.I. Pigment Blue 2, 3, 15, 16, 17, C.I. Vat Blue 6, C.I. Acid Blue 45, copper-phthalocyanine pigments having a phthalocyanine skeleton containing substituents of phthalimidomethyl groups in number of 1 to 5, and the like.

Examples of yellow coloring pigments are C.I. Pigment Yellow 1, 2, 3, 4, 5, 6, 7, 10, 11, 12, 13, 14, 15, 16, 17, 23, 65, 73, 83, C.I. Vat Yellow 1, 3, 20 and the like.

The above-described dyes and pigments may be used solely or may be used while being optionally mixed with one another to obtain desired hue of the toner.

When considering the environmental conservation and the safety to the human body, food colors such as various kinds of food lakes can be suitably used. Examples of such food colors are food red No. 40 aluminum lake, food red No. 2 aluminum lake, food red No. 3 aluminum lake, food red No. 106 aluminum lake, food yellow No. 5 aluminum lake, food yellow No. 4 aluminum lake, food blue No. 1 aluminum lake and food blue No. 2 aluminum lake.

The above described water-insoluble food colors can function as charge controlling agents. When using the food colors as charge controlling agents, the above described aluminum lakes can be suitably used as negatively charging agents. When water-insoluble food colors function as charge controlling agents, not only the safety of toners to the environment is improved, but also the costs of the same are lowered.

The content of the coloring agents in the toner may widely altered depending on the desired coloration effects. Generally, in order to obtain the best toner properties, that is, in consideration of the printing coloration capability, the toner shape stability, and the toner scattering, these coloring agents are used at a ratio in the range of from 0.1 to 60 parts by weight, preferably 0.5 to 20 parts by weight with respect to 100 parts by weight of the binder resin.

<Other Components of Toner>

In the toner of the present invention may contain the following compounds other than the foregoing binder resin and the coloring agent components, to an extent (within a ratio less than the content of the binder resin) in which no undesired effect is caused in the present invention. Examples of such compounds include silicone resin; polyester; polyurethane; polyamide; epoxy resin; poly(vinyl butyral); rosin; modified rosin; terpene resin; phenolic resin; aliphatic or alicyclic hydrocarbon resin such as lower molecular weight polyethylene and lower molecular weight polypropylene; aromatic type petroleum resin; and chlorinated paraffin and paraffin waxes. Among them, preferable waxes to be used are practically lower molecular weight polypropylene and its byproducts, lower molecular weight polyester, and ester type wax and aliphatic derivatives. Among these waxes, waxes fractionated based on the molecular weight of the waxes by various methods are also preferably used in the present invention. Further, after fractionation, the waxes may be modified to control the acid values, block-copolymerized, or graft-modified.

Specially, in the toner of the present invention, in the case such wax components as described above are added and these wax components are found practically dispersed in the binder resin in spherical and/or spindly island state when the section of the toner was observed by a transmission electron microscope, the toner has excellent properties.

<Method of Producing Toners>

Any conventionally known method may be employed for a practical method for producing an toner of the present invention having the constitution as described above. The toner of the present invention can be produced, for example, by a so-called pulverization method for obtaining a toner through the following steps. Specifically, resin materials such as binder resin, and a charge controlling agent to be added as necessary, a wax, are sufficiently mixed by a mixer such as a Henshel mixer, a ball mill and the like and then melted and kneaded using a thermally kneading apparatus such as heating rolls, a kneader, an extruder and the like to make the resin material compatible with one another, and as coloring agents, pigments, dyes, or magnetic materials and also additives such as metal compounds to be added as necessary are dispersed or dissolved in the resulting mixture, and after solidification of the mixture by cooling, the obtained solidified product is pulverized by a pulverizing apparatus such as a jet mill, a ball mill and the like and then classified to obtain an toner of the present invention with a desired particle size. In the above-described classification step, from an aspect of productivity, a multi-step classification apparatus is preferably used.

In addition, the toner of the present invention with a desired particle size can be obtained by mixing and stirring the binder resin and the charge controlling agent in a solvent (e.g., aromatic hydrocarbons such as toluene, xylene and the like; halogen compounds such as chloroform, ethylene dichloride, and the like; ketones such as acetone, methyl ethyl ketone, and the like; amides such as dimethylformamide and the like), and then adding the resulting mixture to water to re-precipitate the solid, then filtering and drying the solid, and further pulverizing it by a pulverizing apparatus such as a jet mill, a ball mill, and the like, and finally classifying the pulverized matter. In the above-described classification step, from an aspect of productivity, a multi-step classification apparatus is preferably used.

In addition, the toner of the present invention can be produced by a so-called polymerization method as follows. That is, in this case, a polymerizable monomer of a binder resin, a charge controlling agent and as coloring agents, pigments, dyes, or magnetic materials and also based on the necessity, additives such as a cross-linking agent, a polymerization initiator, waxes, other binder resins, and others are mixed and dispersed and in the presence of a surfactant or the like, the mixture is subjected to suspension polymerization to obtain a polymerized and colored resin particles, and after the obtained particles are separated by solid-liquid separation, the particles are dried and classified if necessary to obtain a toner of the present invention with a desired particle size. Furthermore, colored fine particles containing no charge controlling agent is produced by the above-described manner and then either solely or together with an externally added agent such as colloidal silica, the above polyhydroxyalkanoate may be attached and fixed to the surface of the particle by a mechanochemical method or the like.

<Externally Added Silica Agent>

In the present invention, a silica fine powder is preferably added externally to the toner produced in a manner as described above for improving the charge stability, development characteristic, fluidity and durability. The silica fine powder to be employed in this case can provide desirable effects if it has a specific surface area of 20 m$^2$/g or higher (especially 30 to 400 m$^2$/g) measured based on the nitrogen adsorption by the BET method. The content of the silica fine powder to be added is preferably 0.01 to 8 parts by weight, more preferably 0.1 to 5 parts by weight, with respect to 100 parts by weight of the toner particles. In this case, based on the necessity, the silica fine powder to be used in the case is preferably treated, for the purpose of controlling the hydrophobicity and charge properties, with silicone varnish, variously modified silicone varnish, silicone oil, variously modified silicone oil, a silane coupling agent, a silane coupling agent having a functional group, and other organosilicon compounds. These treatment agent may be used by mixing.

<Inorganic Powder>

Further, in order to improve the development capability and the durability, the following inorganic powder is preferably added. Examples of the powder are oxides of metals such as magnesium, zinc, aluminum, cerium, cobalt, iron, zirconium, chromium, manganese, strontium, tin, antimony and the like; compounded metal oxides such as calcium titanate, magnesium titanate, and strontium titanate; metal salts such as calcium carbonate, magnesium carbonate, and aluminum carbonates; clay minerals such as kaolin; phosphate compounds such as apatite; silicon compounds such as silicon carbide, and silicon nitride; and carbon powder such as carbon black and graphite. Among them, fine powders of zinc oxide, aluminum oxide, cobalt oxide, manganese dioxide, strontium titanate, and magnesium titanate are preferably used.

<Lubricant>

Further, the following lubricant powder may be added to the toner. For example, fluoro resin such as Teflon, poly(vinylidene fluoride) and the like; fluoride compounds such as carbon fluoride; aliphatic acid metal salts such as zinc stearate; aliphatic acid derivatives such as aliphatic acid, aliphatic acid esters and the like; and molybdenum sulfide.

The contents, in a toner, of the binder resins, colorants, charge controlling agents used in the form of a mixture with the binder resin of this invention and those of other additives added as the need arises are very small; however, it is preferable to use the binder resins, colorants, charge controlling agents and other additives each having biodegradability, if possible, taking into consideration their effects on the environment after use.

<Carrier>

The toner of the present invention having the above-described constitution is usable for a variety of conventionally known toners; solely as a non-magnetic one-component developer, as a non-magnetic toner together with a magnetic carrier for composing a magnetic two-component developer, as a magnetic toner to be used solely for a magnetic mono-component toner. In this case, as the carrier to be used for the two-component development, any conventionally known carrier may be used. More particularly, particles of surface-oxidized or non-oxidized metals such as iron, nickel, cobalt, manganese, chromium and rare earth metals, their alloys and oxides and having an average particle size of 20 to 300 μm may be used as the carrier particles. Further, the carrier to be used in the present invention are preferably the above-described carrier particle whose surface bears or is coated with a substance such as styrene-based resin, acrylic resin, silicone resin, fluoro resin, polyester resin and the like.

<Magnetic Toner>

The toner of the present invention may be a magnetic toner by adding a magnetic material to the toner particles. In this case, the magnetic material may take a role also as a coloring agent. The magnetic material to be used in this case may be iron oxides such as magnetite, hematite, and ferrite; metals such as iron, cobalt, and nickel; alloys of these metals with metals such as aluminum, cobalt, copper, lead, magnesium, tin, zinc, antimony, beryllium, bismuth, cadmium, calcium, manganese, selenium, titanium, tungsten, and vanadium; and their mixtures. The magnetic material to be used in the present invention has an average particle size preferably 2 μm or smaller, more preferably 0.1 to 0.5 μm. The amount to be added to the toner is preferably 20 to 200 parts by weight to 100 parts by weight of the binder resin and especially preferably 40 to 150 parts by weight to 100 parts by weight of the binder resin.

In addition, in order to give high image quality, it is required to precisely develop very small latent image dots and for this purpose, for example, it is preferable that the weight average particle size of the toner of the present invention is controlled so that it is in the range of from 4 to 9 μm. That is, if the toner particle has a weight average particle size smaller than 4 μm, the transfer efficiency is decreased and a large amount of the transfer residual toner tends to remain on a photoconductor to result in an undesirable cause of uneven and irregular image formation due to fogging and transfer failures. Whereas, if the toner particle has a weight average particle size larger than 9 μm, scattering around letters and line images tends to occur.

In the present invention, the average particle size and the particle size distribution of the toner are measured by using Coulter Counter TA-II model or Coulter Multisizer (manufactured by Coulter Co.) or the like to which an interface (manufactured by Nikka Machine Co.) for outputting the distribution by number, the distribution by volume and a PC9801 personal computer (manufactured by NEC) are connected. As an electrolytic solution to be used at that time, an aqueous 1% NaCl solution is prepared using first-grade sodium chloride. As the electrolytic solution, for example, a commercialized ISOTON R-II (produced by Coulter Scientific Japan Co.) may also be usable. A practical measurement method involves steps of adding 0.1 to 5 mL of a surfactant (preferably an alkylbenzenesulfonic acid salt is used) as a dispersant to 100 to 150 mL of the above-described aqueous solution, further adding 2 to 20 mg of a sample to the resulting solution to obtain a specimen to be measured. At the time of measurement, the electrolytic solution in which the specimen to be measured is suspended is treated for dispersion for 1 to 3 minutes by an ultrasonic dispersing apparatus and then the volume and the number of the toner particles of 2 μm or larger are measured by the foregoing Coulter Counter TA-II model using 100 μm aperture and the distribution by volume and the distribution by number are calculated. Then, the weight average particle size (D4) on the basis of the volume calculated from the distribution by volume according to the present invention and the length average particle size (D1) on the basis of the number calculated from the distribution by number are calculated.

<Charge Level>

In addition, the charge level of the toner of the present invention is preferably in the range of from −10 to −80 μC/g, more preferably from −15 to −70 μC/g per unit weight (two-component method) in improving the transfer efficiency in a transfer method using a transfer member with a voltage applied thereto.

Figure 11:
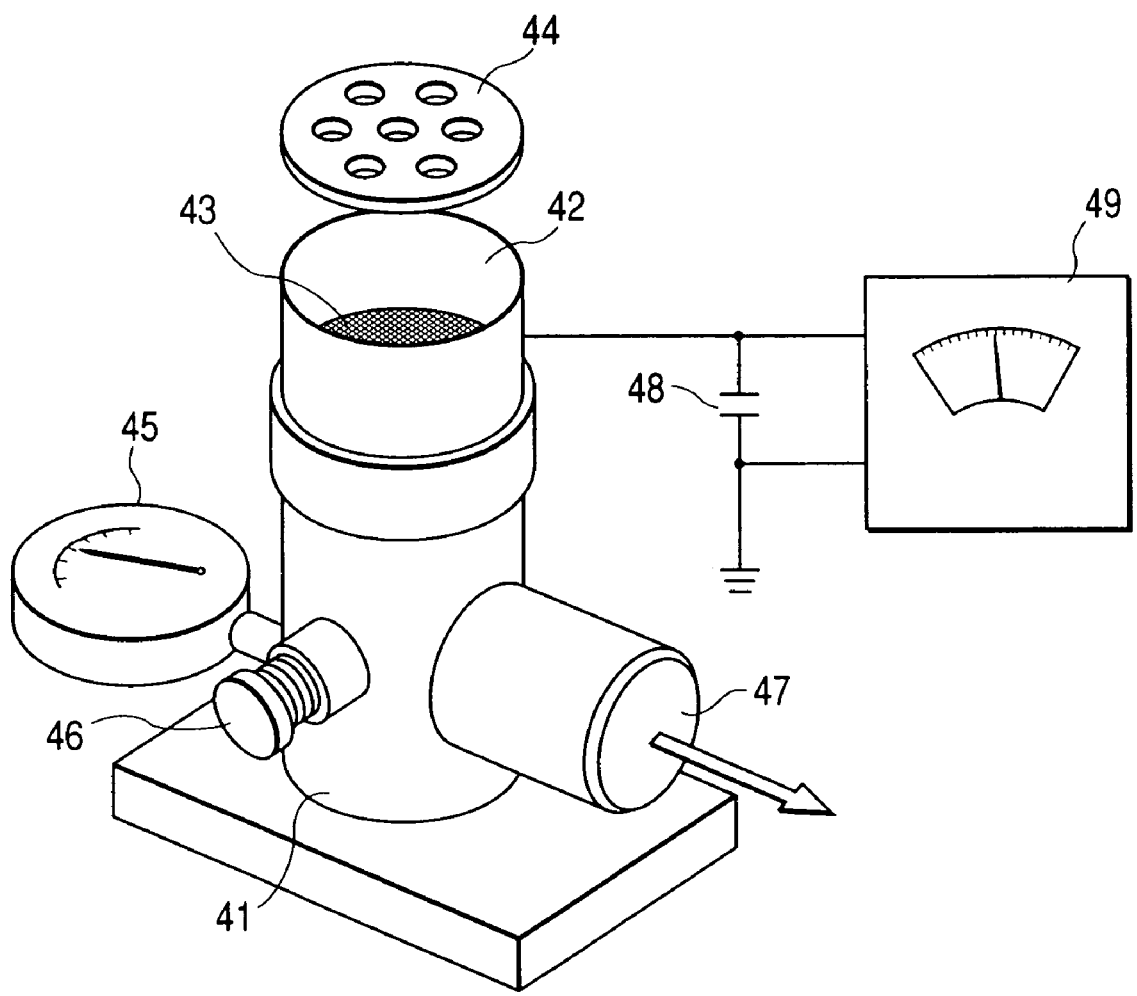
FIG. 11 is a schematic illustration of a blowoff chargemetry which measures the amount of charge on toners.

The method of measuring an charge level (a two-component tribo) by the two-component method employed in the present invention will be described as follows. A charge level measuring apparatus illustrated in FIG. 11 is used for the measurement. At first, under a specified environment, EFV 200/300 (produced by Powder Tec Co.) is used as a carrier and a bottle made of a polyethylene with a capacity of 50 to 100 mL is charged with a mixture of 9.5 g of the carrier and 0.5 g of a toner to be measured, set in a shaking apparatus so controlled as to keep the amplitude constant, and shaken for a prescribed period in the shaking conditions of an amplitude of 100 mm and a shaking speed of 100 rpm. Then, 1.0 to 1.2 g of the above mixture is placed in a measurement container 42 made of metal having a 500-mesh screen 43, and the measurement container 42 is covered with a metal lid 44 in the bottom of the charge level measuring apparatus shown in FIG. 11. The total weight of the measurement container 42 at that time is measured and determined as W1 (g). Next, the gas in the container is aspirated through a suction port 47 by an unillustrated aspirator (at least the portion contacting the measurement container 42 is made of an insulator) and an air ventilation adjustment valve 46 is controlled to control the pressure of the vacuum meter 45 to be 2,450 Pa (250 mmAq). Under such a state, aspiration is carried out for 1 minute to suck and remove the toner. The potential of a potentiometer 49 at that time is denoted as V (volt). The reference numeral 48 denotes a capacitor and the capacity is denoted as C (μF). The weight of the entire measurement container after the aspiration is weighed and denoted as W2 (g). The friction charge level (μC/g) of the toner can be calculated according to the following equation from these measurement values.

Friction charge level $(\mu C/g) = C \times V/(W1 - W2)$

<Method for Measuring Molecular Weight of Binder Resin and Molecular Weight Distribution>

The binder resin for use in the constituent material of the toner of the present invention preferably has a peak within the range of from 3,000 to 15,000 in a low molecular weight region of the molecular weight distribution measured by GPC, especially, in the case of production by the pulverization method. That is, if the GPC peak exceeds 15,000 in the low molecular weight region, it sometimes becomes difficult to obtain a toner with a sufficiently improved transfer efficiency. Whereas if binder resin having a GPC peak of less than 3,000 is used, melting takes place easily at the time of surface treatment and therefore it is undesirable.

In the present invention, the molecular weight of the binder resin is measured by GPC (gel permeation chromatography). A practical GPC measurement method is carried out as follows: a toner previously extracted with THF (tetrahydrofuran) solvent for 20 hours using a Soxhlet extractor is used as a sample for measurement. Using columns A-801, 802, 803, 804, 805, 806, and 807 manufactured by Showa Denko K.K. and the calibration curve of standardized polystyrene resins, the molecular weight distribution is measured. Further, in the present invention, it is preferable that the binder resin with the ratio (Mw/Mn) of the weight average molecular weight (Mw) to the number average molecular weight (Mn) measured as described above being in the range of from 2 to 100 is used.

<Glass Transition Temperature of Toner>

Further, the toner of the present invention is preferably adjusted by using a proper material so as to have a glass transition temperature Tg in the range of from 40 to 75° C., more preferably 52 to 70° C., from a viewpoint of fixation and storage stability. In this case, the measurement of the glass transition temperature Tg may be carried out using a high precision and internally heating input compensation type differential scanning calorimeter, for example, DSC-7 manufactured by Perkin Elmer Co., may be employed. The measurement method is carried out according to ASTM D3418-82. In the present invention, when the glass transition temperature Tg is measured, it is preferable that a measurement sample is once heated to cancel the entire hysteresis and then cooled rapidly and again heated at a heating rate of 10° C./min to employ the DSC curve measured during the heating from 0 to 200° C.

<Image Formation Method>

The toner of the present invention having the configuration described above is particularly preferably applied to an image formation method and an apparatus therefor, the method comprising at least an charging step of applying a voltage to a charging member from the outside to charge an electrostatic latent image-holding member, a step of forming an electrostatic latent image on the charged electrostatic latent image-holding member, a development step of developing the electrostatic latent image with the toner to form a toner image on the electrostatic latent image-holding member, a transfer step of transferring the toner image on the electrostatic latent image-holding member to a recording material, and a heat-fixation step of heat-fixing the toner image on the recording material. Alternatively, an image formation method and an apparatus therefor can be used where the transfer step consists of a first transfer step of transferring the toner image on the electrostatic latent image-holding member to an intermediate transfer member and a second transfer step of transferring the toner image on the intermediate transfer member to the recording material.

The culture of microorganisms, the recovery of the PHA from the microorganisms, the resin compositions and the moldings, and in addition, the toner binder resins, the charge controlling agents, etc. of this invention are all not limited to the above described methods.

EXAMPLES

Next, the present invention is described further specifically with reference to Examples and Comparative Examples. It should be noted that these Examples are illustrative of the best mode of the embodiment of the present invention and do not limit the present invention. Further, all parts in the following formulations are by mass and "%" is by mass, unless otherwise specified.

[PHA]

First, a method for preparing polyhydroxyalkanoate of the present invention comprising a microbiological production step and a chemical processing step is shown below (Examples A-1 to A-5).

Example A-1

<Preparative Process 1: Biosynthesis of Aromatic Vinyl PHA (1)>

A culture medium containing 5-(4-vinylphenyl)valeric acid as an ω-(4-vinylphenyl)alkanoic acid represented by general formula (17) and 5-phenylvaleric acid as an ω-substituted alkanoic acid represented by general formula (18), and polypeptone as a peptide source was prepared as follows: 5.0 g of polypeptone (Wako Pure Chemicals Industries, Ltd.)

and 0.8912 g of 5-phenylvaleric acid were dissolved in 1000 mL of the above M9 culture medium, put in a 2000 mL shaking flask, and sterilized by an autoclave. After the above heat sterilization treatment, the mixture was cooled to room temperature, and 0.2043 g of 5-(4-vinylphenyl)valeric acid was added. Then, the resultant mixture was sufficiently stirred to prepare a culture medium.

*Pseudomonas cichorii* YN2 strain was inoculated in an M9 culture medium containing 0.5% of polypeptone and shake-cultured at 30° C. for 8 hours to prepare a preculture. 5 mL of this preculture solution was added to the above culture medium containing 5-(4-vinylphenyl)valeric acid and 5-phenylvaleric acid as substrates to culture the cells at 30° C. for 39 hours. After being cultured, the cells were collected by centrifugation, washed with methanol, and then lyophilized.

After dried cells were weighed, chloroform was added. The mixture was stirred at 25° C. for 72 hours, thereby extracting the polymer accumulated in the cell. The chloroform solution with the extracted polymer dissolved therein was filtered. The chloroform filtrate was concentrated by an evaporator, followed by redissolving the polymer in acetone and filtering off insoluble components. Then, the filtrate was concentrated by an evaporator, and precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature) to find that the polymer was a polyhydroxyalkanoate copolymer containing units represented by the following formula (22)

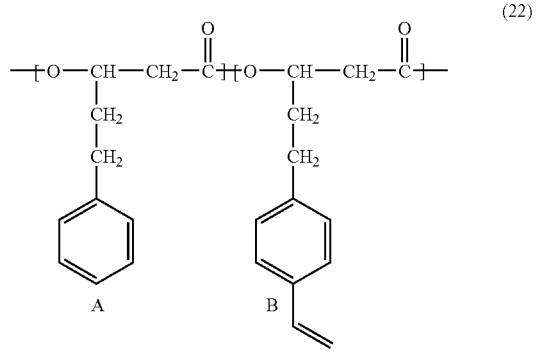

(22)

in a content ratio (mol %) of A:B=83:17. The $^1$H-NMR spectrum of the resultant polymer is shown in FIG. 1.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

Dry weight of the cells obtained in the above step (CDW), dry weight of the collected polymer (PDW), weight ratio of the collected polymer to dried cells (P/C), and the number average molecular weight (Mn), the weight average molecular weight (Mw), and the molecular weight distribution (Mw/Mn) of the resultant polymer are shown together in Table 1.

TABLE 1

| | | Productivity of polymer | | | |
|---|---|---|---|---|---|
| CDW (mg/L) | PDW (mg/L) | P/C % | Mn (×10$^4$) | Mw (×10$^4$) | Mw/Mn |
| 1205 | 600 | 49.8 | 5.9 | 12.1 | 2.1 |

CDW: dry weight of cells;
PDW: dry weight of polymer;
P/C: dry weight of cells/dry weight of polymer;
Mn: number average molecular weight;
Mw: weight average molecular weight;
Mw/Mn: molecular weight distribution <Synthesis of Aromatic Carboxy PHA by Oxidation Reaction (1)>

Under a nitrogen atmosphere, 0.3061 g of polyester containing a 3-hydroxy-ω-(4-vinylphenyl)valeric acid unit obtained in the above Preparative Process 1, 0.1923 g of 18-crown-6-ether, and 10.0 mL of dichloromethane were added to a 100 mL flask followed by stirring. The flask was dipped in an ice bath to cool the reaction system to 0° C. After 30 minutes, 0.1517 g of potassium permanganate was added. The reaction vessel was wrapped with aluminum foil followed by stirring for 21 hours. After the reaction was completed, water having sodium bisulfite dissolved therein was added, and the reaction solution was reprecipitated in methanol to collect the polymer. The polymer obtained here was dialyzed by using chloroform for purification.

Figure 2:
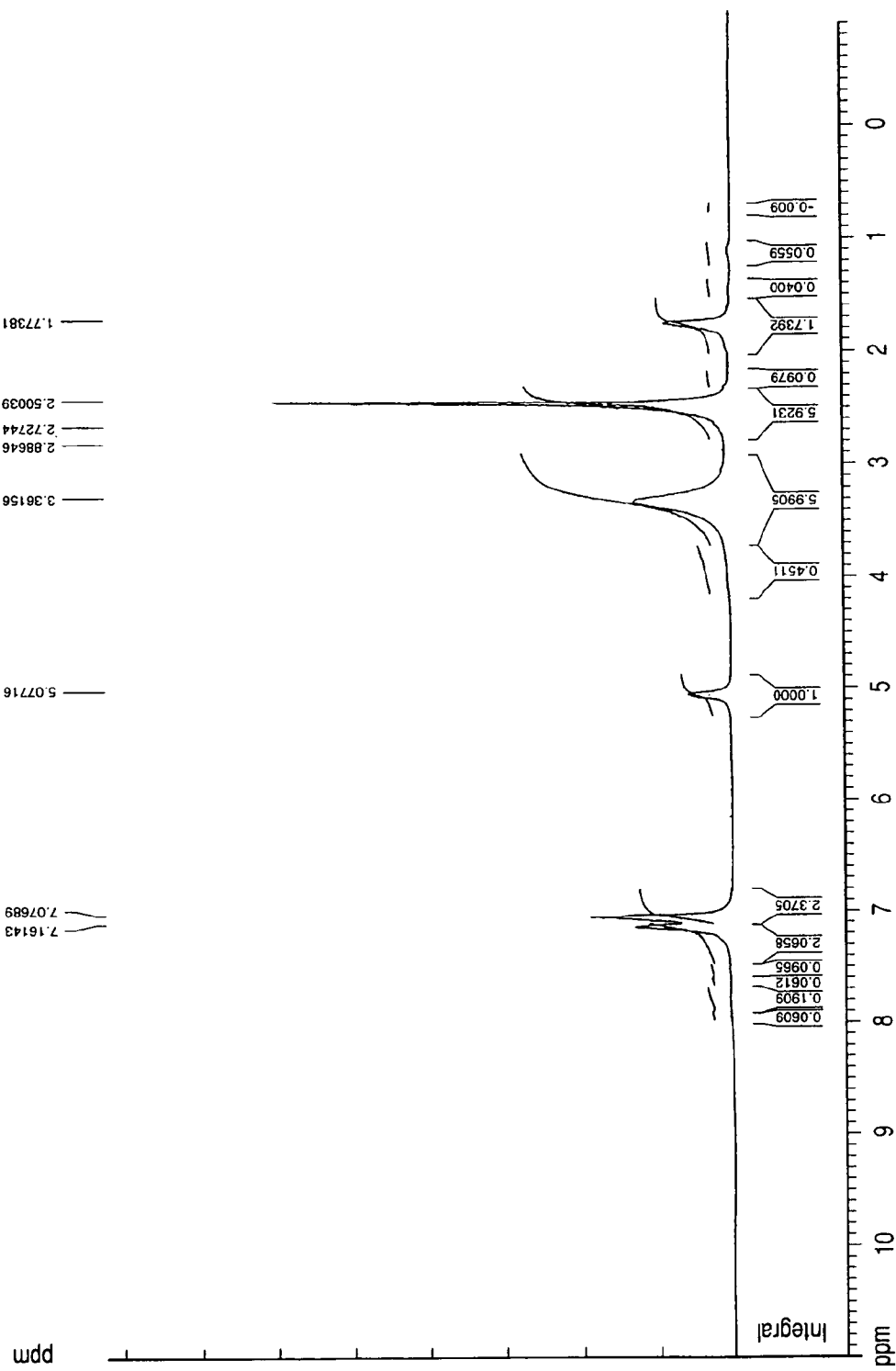
FIG. 2 is a $^1$H-NMR spectrum of the polyhydroxyalkanoate finally obtained in Example A-1.

The structure of the resultant polymer was determined by $^1$H-NMR (FT-NMR: Bruker DPX400; resonance frequency: 400 MHz; measurement nuclear species: $^1$H; solvent used: deuterated chloroform; measurement temperature: room temperature) and analyzed by Fourier transform infrared absorption (FT-IR) spectrum (Nicolet AV ATAR360 FT-IR). As the result, an additional absorption derived from carboxylic acid was found at 1693 cm$^{-1}$, and hence it was found that the resultant PHA had a 3-hydroxy-ω-(4-carboxyphenyl)valeric acid unit. The $^1$H-NMR spectrum of the resultant polymer is shown in FIG. 2.

Further, in order to calculate the units of the resultant PHA, the calculation was performed by methyl-esterifying a carboxyl group on the end of the side chain of PHA by using trimethylsilyldiazomethane.

30 mg of the desired product of PHA was added to a 100 mL round bottomed flask, and then 2.1 mL of chloroform and 0.7 mL of methanol were added and dissolved. To the mixture, 0.5 mL of 2 mol/L trimethylsilyldiazomethane-hexane solution (Aldrich) was added followed by stirring at room temperature for 30 minutes. After the reaction was completed, the solvent was distilled off by an evaporator to collect the polymer. After washing with 50 mL of methanol, the polymer was collected. 32 mg of PHA was obtained by drying under a reduced pressure.

From the result of NMR analysis in the similar manner of the above method, the resultant PHA was found to be a polyhydroxyalkanoate copolymer containing units represented by the following formula (23)

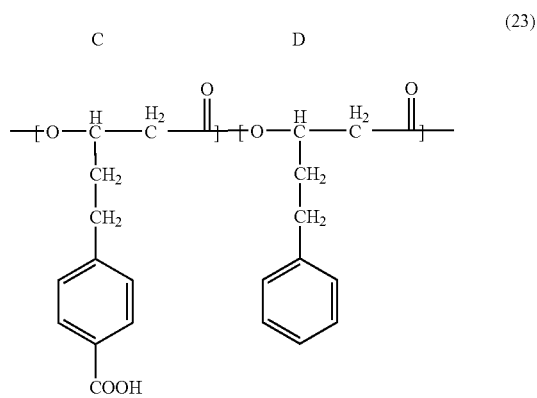

in a content ratio (mol %) of C:D=17:83.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 29600, and the weight average molecular weight Mw was 62800.

By scaling up the above preparation method, 50 g of PHA was obtained and it was referred to as PHA(A-1).

Example A-2

<Preparative Process 2: Biosynthesis of Aromatic Vinyl PHA (2)>

Three 2000 mL shaking flasks were prepared. 0.5 wt % of polypeptone (Wako Pure Chemicals Industries, Ltd.), 6.0 mmol/L of 5-(phenylsulfanyl)valeric acid, and 1 mmol/L of 5-(4-vinylphenyl)valeric acid were dissolved in 1000 mL of the above M9 culture medium, charged in each of the 2000 mL shaking flask, and sterilized by an autoclave followed by cooling to the room temperature. To each of the prepared culture medium, 10 mL of a culture solution of *Pseudomonas cichorii* YN2 precultured in an M9 medium containing 0.5% of polypeptone with shaking for 8 hours was added, and the mixture was cultured at 30° C. for 38 hours. After being cultured, the culture was pooled, and cells were collected by centrifugation, washed with methanol, and then dried. After the weight of the dried cells was weighed, chloroform was added. The mixture was stirred at 35° C. for 25 hours, thereby extracting the polymer. The chloroform from which the polymer was extracted was filtered by a 0.45 μm membrane filter, concentrated by an evaporator, and then reprecipitated in cold methanol to collect the polymer. Thereafter, the polymer was dried under a reduced pressure to obtain the desired polymer.

As the result of weighing the resultant polymer, 1111 mg (dry weight) of PHA was obtained in this example.

The average molecular weight of the resultant PHA was evaluated by gel permeation chromatography (GPC; Tosoh HLC-8220; column: Tosoh TSK-GEL SuperHM-H; solvent; chloroform; polystyrene equivalent). The result showed that the number average molecular weight Mn was 105000.

Figure 3:
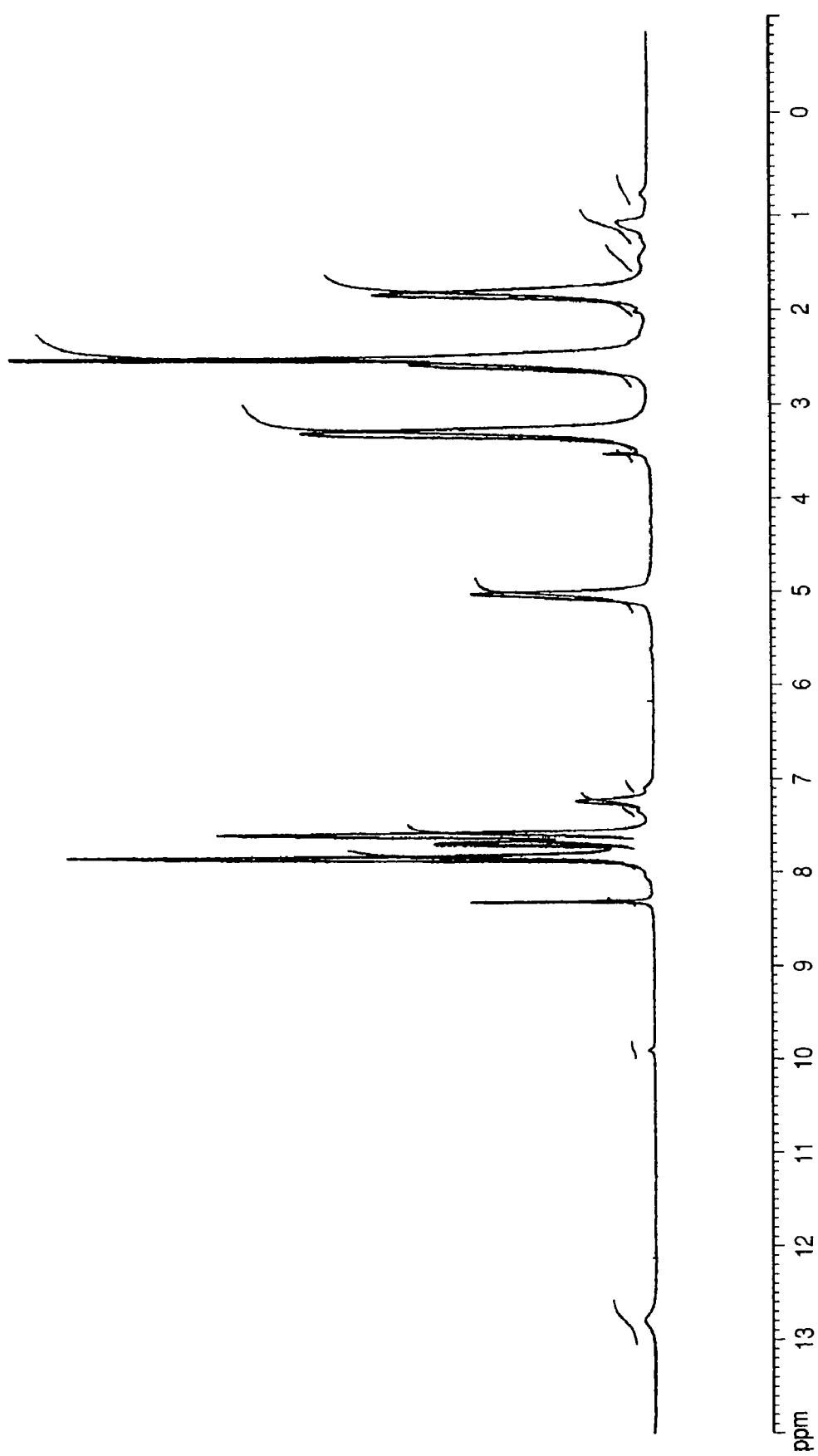
FIG. 3 is a $^1$H-NMR spectrum of the polyhydroxyalkanoate obtained by the pre-preparation 2 in Example A-2.

Further, in order to determine the structure of the resultant PHA, NMR analysis was performed under the similar condition as in Preparative Process 1. The $^1$H-NMR spectrum of the resultant polymer is shown in FIG. 3. As the result, the PHA was found to be a polyhydroxyalkanoate copolymer containing a 3hydroxy-5-(phenylsulfanyl)valeric acid unit and a 3-hydroxy-ω-(4-vinylphenyl)valeric acid unit as monomer units as represented by the following chemical formula (24).

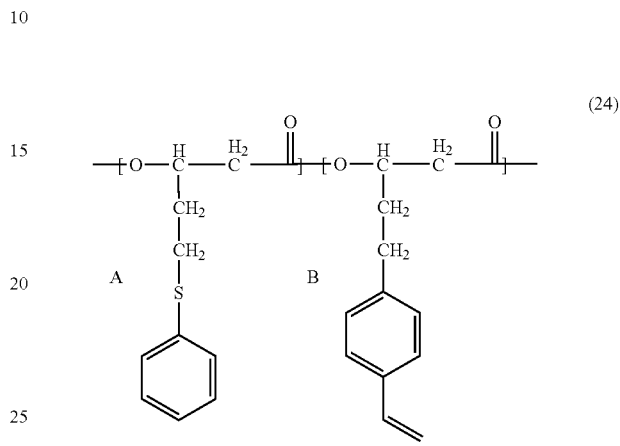

Moreover, the proportion of the units was confirmed by $^1$H-NMR spectrum to be 70 mol % of 3-hydroxy-5-(phenylsulfanyl)valeric acid, 20 mol % of 3-hydroxy-ω-(4-vinylphenyl)valeric acid, and 10 mol % of the others (straight-chained 3-hydroxyalkanoic acid having 4 to 12 carbon atoms).

<Synthesis of Aromatic Carboxy PHA by Oxidation Reaction (2)>

302 mg of polyhydroxyalkanoate obtained in the above Preparative Process 2 was added to a 200 mL round bottomed flask, and then 20 mL of dichloromethane was added and dissolved. The mixture was placed in an ice bath, and 3 mL of acetic acid and 1103 mg of 18-crown-6-ether were added followed by stirring. Next, 877 mg of potassium permanganate was gradually added to the flask in an ice bath followed by stirring at room temperature for 21 hours. After the reaction was completed, 50 mL of water and 3050 mg of sodium bisulfite were added. Then, the solution was made to be pH 1 by adding 1.0 mol/L (1.0 N) hydrochloric acid. After dichloromethane in the mixed solution was distilled off by an evaporator, the polymer in the solution was collected. The polymer was washed with 150 mL of pure water, 150 mL of methanol, 150 mL of pure water 2 times, and 50 mL of methanol in this order followed by collecting the polymer. The polymer was dried under a reduced pressure to obtain 342 mg of the desired PHA.

Figure 4:
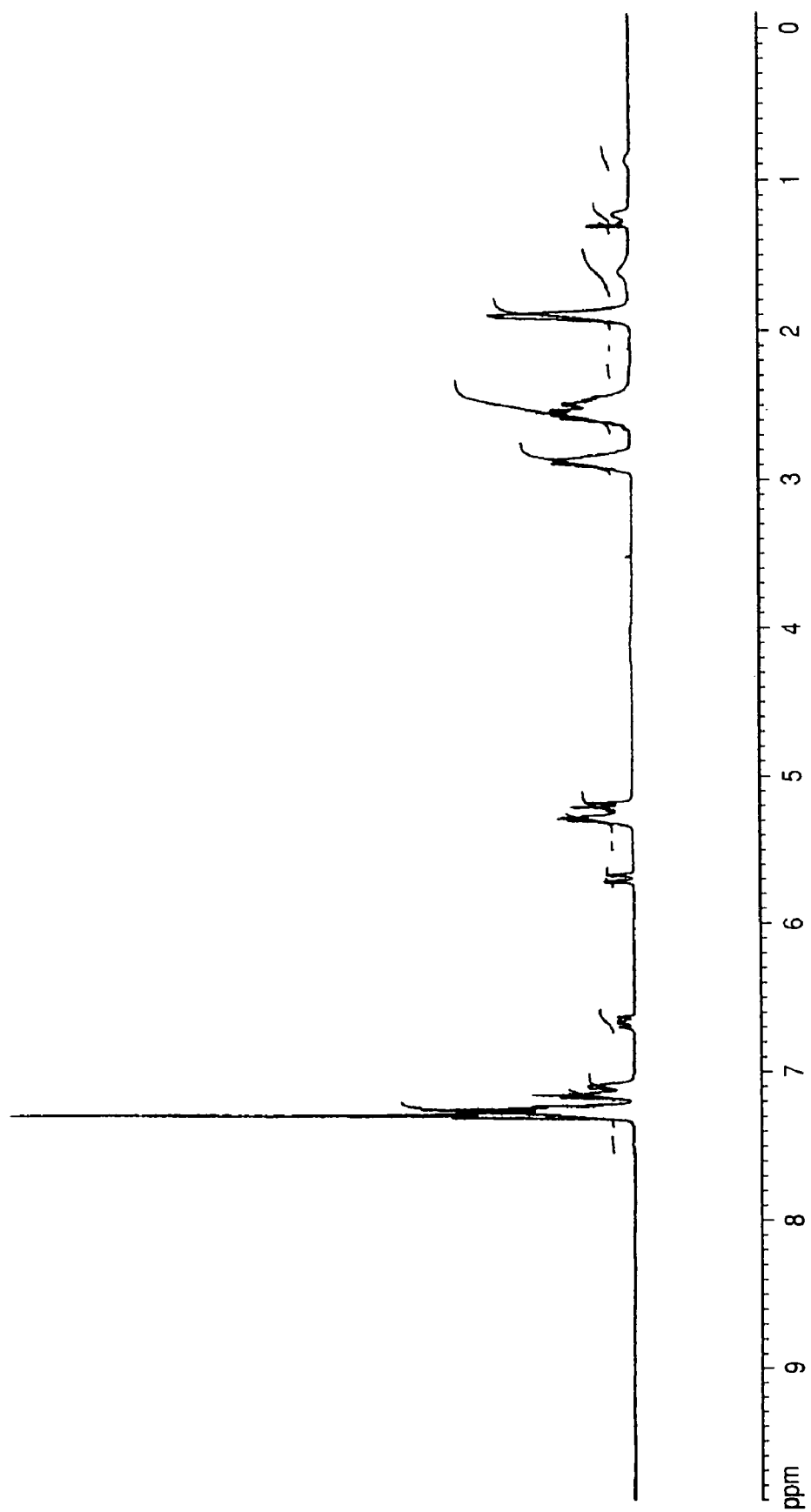
FIG. 4 is a $^1$H-NMR spectrum of the polyhydroxyalkanoate finally obtained in Example A-2.

Further, in order to determine the construction of the resultant PHA, analysis was performed by $^1$H-NMR (FT-NMR: Bruker DPX400; resonance frequency: 400 MHz; measurement nuclear species: $^1$H; solvent used: dDMSO; measurement temperature: room temperature). The $^1$H-NMR spectrum of the resultant polymer is shown in FIG. 4. As the result, the polymer was found to be a polyhydroxyalkanoate copolymer containing a 3-hydroxy-5-(phenylsulfonyl)valeric acid unit and a 3-hydroxy-ω-(4-carboxyphenyl)valeric acid unit as monomer units as represented by the following chemical formula (25).

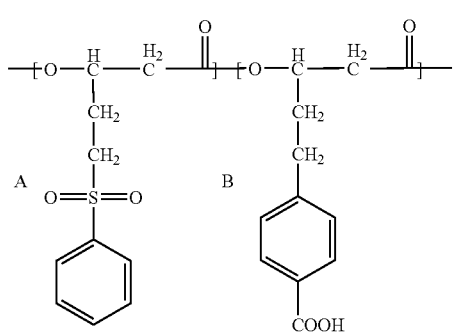

(25)

Further, in order to calculate the units of the resultant PHA, the calculation was performed by methyl-esterifying a carboxyl group on the end of the side chain of PHA by using trimethylsilyldiazomethane.

30 mg of the desired product of PHA was added to a 100 mL round bottomed flask, and then 2.1 mL of chloroform and 0.7 mL of methanol were added and dissolved. To the mixture, 0.5 mL of 2 mol/L trimethylsilyldiazomethane-hexane solution (Aldrich) was added followed by stirring at room temperature for 30 minutes. After the reaction was completed, the solvent was distilled off by an evaporator to collect the polymer. After washing with 50 mL of methanol, the polymer was collected. 31 mg of PHA was obtained by drying the polymer under a reduced pressure.

NMR analysis was performed in the same manner as described above. As a result, $^1$H-NMR spectrum confirmed that the proportion of the units is 74 mol % of 3-hydroxy-5-(phenylsulfonyl)valeric acid, 17 mol % of a 3-hydroxy-ω-(4-carboxyphenyl)valeric acid unit, and 9 mol % of the others (straight-chained 3-hydroxyalkanoic acid having 4 to 12 carbon atoms).

The PHA obtained in the method of Example A-2 was referred to as PHA(A-2).

Example A-3

<Preparative Process 3: Biosynthesis of Aromatic Vinyl PHA (3)>

5.0 g of polypeptone (Wako Pure Chemicals Industries, Ltd.), 0.612 g of 5-(4-vinylphenyl)valeric acid, and 1.068 g of 5-phenylvaleric acid were added to 1000 mL of an M9 culture medium, charged in a 2000 mL shaking flask, sterilized by an autoclave, and cooled to room temperature to prepare a culture medium. Six flasks of this culture medium were prepared.

*Pseudomonas cichorii* YN2 was inoculated in an M9 culture medium containing 0.5% of polypeptone and shake-cultured at 30° C. for 8 hours to prepare a preculture solution. 10 mL of this culture solution was added to each of the above culture medium containing 5-(4-vinylphenyl)valeric acid and 5-phenylvaleric acid as substrates to culture the cells at 30° C. for 63 hours. After being cultured, the cells were collected by centrifugation, washed with methanol, and then lyophilized.

After dried cells were weighed, chloroform was added. The mixture was stirred at 35° C. for 16 hours, thereby extracting the polymer accumulated in the cell. The chloroform solution with the extracted polymer dissolved therein was filtered. The chloroform filtrate was concentrated by an evaporator, followed by redissolving the polymer in acetone and filtering off insoluble components. Then, the filtrate was concentrated by an evaporator, and precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature) to find that the polymer was a polyhydroxyalkanoate copolymer containing units represented by the following formula (26)

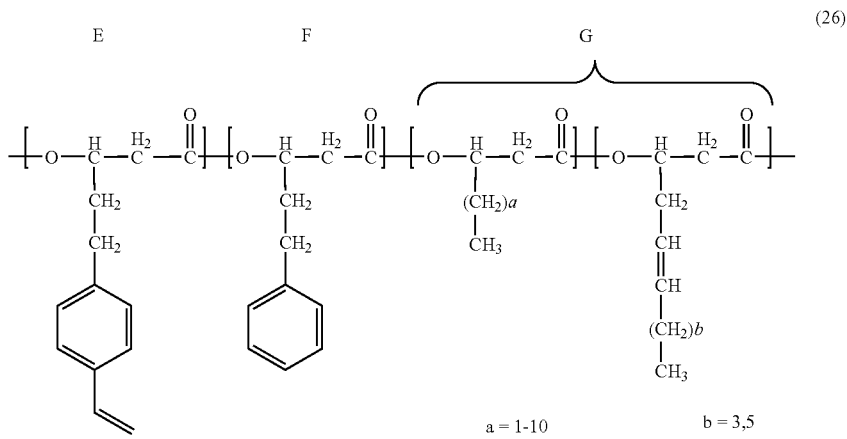

(26)

(a and b may take any one or more integer values within the range shown in the chemical formula. When there are a plurality of monomer units, each monomer unit independently represents the above meaning.) in a content ratio (mol %) of E:F:G=40:58:2.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

The dry weight of cells obtained in the above step (CDW), the dry weight of the collected polymer (PDW), the weight ratio of the collected polymer to dried cells (P/C), and the number average molecular weight (Mn), the weight average molecular weight (Mw), and the molecular weight distribution (Mw/Mn) of the resultant polymer are shown together in Table 2.

1604 mg of the polymer was obtained by drying under a reduced pressure.

The construction of the resultant polymer was determined by analysis by Fourier transform infrared absorption (FT-IR) spectrum (Nicolet AV ATAR360 FT-IR). As a result, an additional absorption derived from carboxylic acid was found at 1693 cm$^{-1}$, and hence it was found that the resultant polyhydroxyalkanoate had a 3-hydroxy-ω-(4-carboxyphenyl)valeric acid unit. Moreover, the product obtained by reacting the resultant polymer and trimethylsilyldiazomethane was evaluated by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature) to find that the polymer was a polyhydroxyalkanoate copolymer containing units represented by the following formula (27)

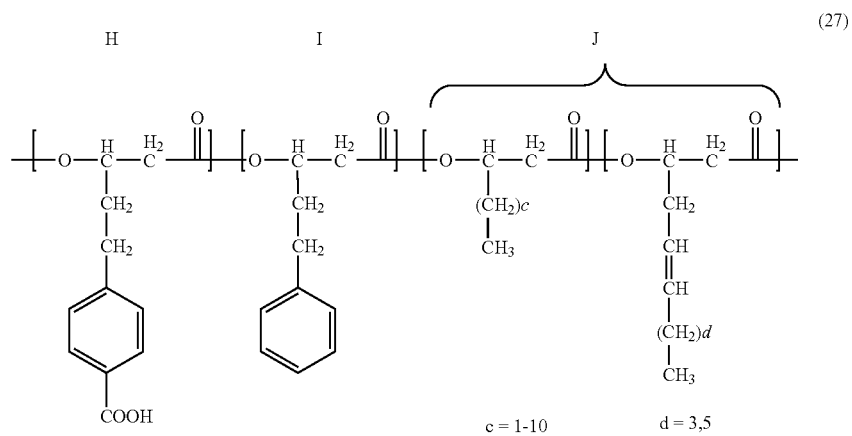

(27)

TABLE 2

| | | Productivity of polymer | | | |
|---|---|---|---|---|---|
| CDW (mg/L) | PDW (mg/L) | P/C (%) | Mn (×10$^4$) | Mw (×10$^4$) | Mw/Mn |
| 930 | 330 | 35.5 | 4.4 | 12.4 | 2.8 |

<Synthesis of Aromatic Carboxy PHA by Oxidation Reaction (3)>

Polyhydroxyalkanoate obtained in the above Preparative Process 3 was utilized in the next reaction.

1604 mg of polyhydroxyalkanoate was added to a 500 mL round bottomed flask, and then 96 mL of dichloromethane was added and dissolved. The mixture was placed in an ice bath, 16 mL of acetic acid and 2726 mg of 18-crown-6-ether were added followed by stirring. After 40 minutes, 2174 mg of potassium permanganate was gradually added followed by stirring in an ice bath for 1 hour and then at room temperature for 11 hours. After the reaction was completed, 100 mL of water and 5000 mg of sodium bisulfite were added. Then, the solution was made to be pH 1 by adding 1.0 N hydrochloric acid. After dichloromethane in the mixed solution was distilled off by an evaporator, the polymer in the solution was collected. The polymer was washed with 200 mL of methanol and then with 200 mL of pure water 3 times followed by collecting the polymer. Then, the resultant polymer was dialyzed by using chloroform for purification. After purification, (c and d may take any one or more integer values within the range shown in the chemical formula. When there are a plurality of monomer units, each monomer unit independently represents the above meaning.) in a content ratio (mol %) of H:I:J=38:58:4.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 30100, and the weight average molecular weight Mw was 65400.

By scaling up the above preparation method, 50 g of PHA was obtained and it was referred to as PHA(A-3).

Example A-4

<Preparative Process 4: Biosynthesis of Aromatic Vinyl PHA (4)>

5.0 g of polypeptone (Wako Pure Chemicals Industries, Ltd.), 0.204 g of 5-(4-vinylphenyl)valeric acid, and 1.068 g of 5-phenylvaleric acid were added to 1000 mL of an M9 culture medium, charged in a 2000 mL shaking flask, sterilized by an autoclave, and cooled to room temperature to prepare a culture medium.

*Pseudomonas cichorii* YN2 was inoculated in an M9 culture medium containing 0.5% of polypeptone and shake-cultured at 30° C. for 8 hours to prepare a preculture solution.

10 mL of this culture solution was added to the above culture medium containing 5-(4-vinylphenyl)valeric acid and 5-phenylvaleric acid as substrates to culture the cells at 30° C. for 64 hours. After being cultured, the cells were collected by centrifugation, washed with methanol, and then lyophilized. After dried cells were weighed, chloroform was added. The mixture was stirred at 35° C. for 20 hours, thereby extracting the polymer accumulated in the cell. The chloroform solution with the extracted polymer dissolved therein was filtered. The chloroform filtrate was concentrated by an evaporator, followed by redissolving the polymer in acetone and filtering off insoluble components. After the filtrate was concentrated by an evaporator, precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/$CDCl_3$; measurement temperature: room temperature) to find that the polymer was a polyhydroxyalkanoate copolymer containing units represented by the following formula (26)

TABLE 3

| | | Productivity of polymer | | | |
|---|---|---|---|---|---|
| CDW (mg/L) | PDW (mg/L) | P/C (%) | Mn (×10$^4$) | Mw (×10$^4$) | Mw/Mn |
| 1000 | 510 | 51.0 | 4.9 | 12.5 | 2.6 |

<Synthesis of Aromatic Carboxy PHA by Oxidation Reaction (4)>

Polyhydroxyalkanoate obtained in the above Preparative Process 4 was utilized in the next reaction.

1400 mg of polyhydroxyalkanoate was added to a 500 mL round bottomed flask, and then 60 mL of dichloromethane was added and dissolved. The mixture was placed in an ice bath, 9 mL of acetic acid and 804 mg of 18-crown-6-ether were added followed by stirring. After 60 minutes, 640 mg of potassium permanganate was gradually added followed by stirring in an ice bath for 1 hour and then at room temperature for 19 hours. After the reaction was completed, 100 mL of water and 2000 mg of sodium bisulfite were added. Then, the solution was made to be pH 1 by adding 1.0 N hydrochloric acid. After dichloromethane in the mixed solution was dis-

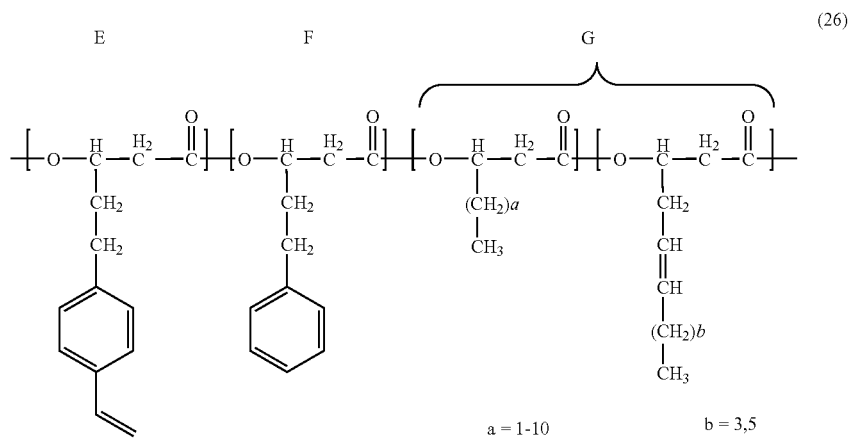

(26)

(a and b may take any one or more integer values within the range shown in the chemical formula. When there are a plurality of monomer units, each monomer unit independently represents the above meaning.) in a content ratio (mol %) of E:F:G=14:83:3.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

The dry weight of cells obtained in the above step (CDW), the dry weight of the collected polymer (PDW), the weight ratio of the collected polymer to dried cells (P/C), and the number average molecular weight (Mn), the weight average molecular weight (Mw), and the molecular weight distribution (Mw/Mn) of the resultant polymer are shown together in Table 3.

tilled off by an evaporator, the polymer in the solution was collected. The polymer was washed with 200 mL of methanol and then with 200 mL of pure water 3 times followed by collecting the polymer. Then, the resultant polymer was dialyzed by using chloroform for purification. After purification, 1410 mg of the polymer was obtained by drying under a reduced pressure.

The construction of the resultant polymer was determined by analysis by Fourier transform infrared absorption (FT-IR) spectrum (Nicolet AV ATAR360 FT-IR). As the result, an additional absorption derived from carboxylic acid was found at 1693 cm$^{-1}$, and hence it was found that the resultant polyhydroxyalkanoate had a 3-hydroxy-ω-(4-carboxyphenyl)valeric acid unit. Moreover, the product obtained by reacting the resultant polymer and trimethylsilyldiazomethane was evaluated by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/

CDCl$_3$; measurement temperature: room temperature) to find that the polymer was a polyhydroxyalkanoate copolymer containing units represented by the following formula (27)

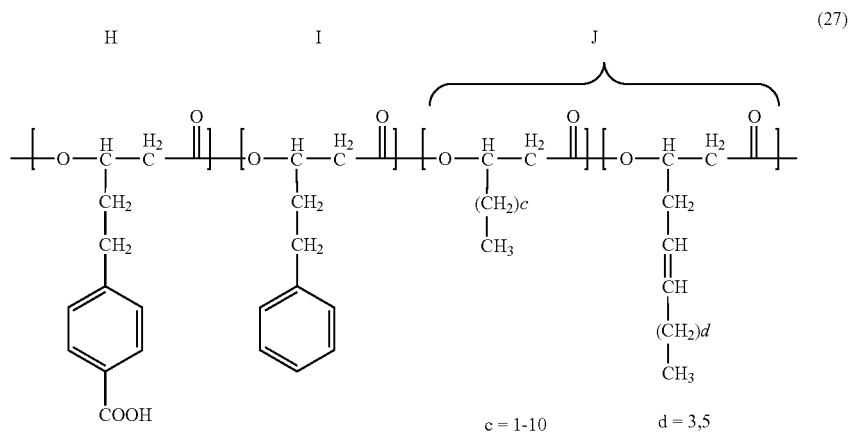

(27)

c = 1-10   d = 3,5

(c and d may take any one or more integer values within the range shown in the chemical formula. When there are a plurality of monomer units, each monomer unit independently represents the above meaning.) in a content ratio (mol %) of H:I:J=12:88:0.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 29400, and the weight average molecular weight Mw was 63200.

By scaling up the above preparation method, 50 g of PHA was obtained and it was referred to as PHA(A-4).

Example A-5

<Preparative Process 5: Biosynthesis of Aromatic Vinyl PHA (5)>

5.0 g of polypeptone (Wako Pure Chemicals Industries, Ltd.), 0.205 g of 5-(4-vinylphenyl)valeric acid, and 1.284 g of 5-(phenylsulfanyl)valeric acid were added to 1000 mL of an M9 culture medium, charged in a 2000 mL shaking flask, sterilized by an autoclave, and cooled to room temperature to prepare a culture medium. (Six flasks of this culture medium were prepared.) *Pseudomonas cichorii* YN2 was inoculated in an M9 culture medium containing 0.5% of polypeptone and shake-cultured at 30° C. for 8 hours to prepare a preculture solution. 10 mL of this culture solution was added to each of the above culture medium containing 5-(4-vinylphenyl) valeric acid and 5-(phenylsulfanyl)valeric acid as substrates to culture the cells at 30° C. for 38 hours. After being cultured, the cells were collected by centrifugation, washed with methanol, and then lyophilized.

After dried cells were weighed, chloroform was added. The mixture was stirred at 35° C. for 16 hours, thereby extracting the polymer accumulated in the cell. The chloroform solution with the extracted polymer dissolved therein was filtered. The chloroform filtrate was concentrated by an evaporator, followed by redissolving the polymer in acetone and filtering off insoluble components. Then, the filtrate was concentrated by an evaporator, and precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/ CDCl$_3$; measurement temperature: room temperature) to find that the polymer was a polyhydroxyalkanoate copolymer containing units represented by the following formula (28)

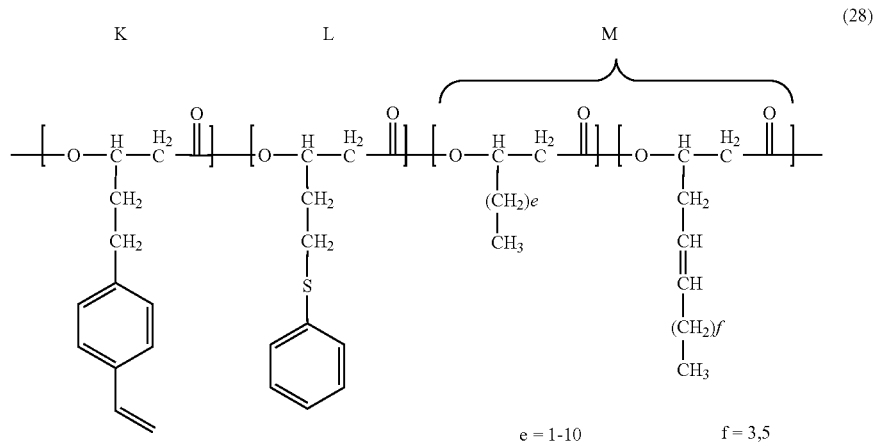

(28)

e = 1-10   f = 3,5

(e and f may take any one or more integer values within the range shown in the chemical formula. When there are a plurality of monomer units, each monomer unit independently represents the above meaning.) in a content ratio (mol %) of K:L:M=18:78:4.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

The dry weight of cells obtained in the above step (CDW), the dry weight of the collected polymer (PDW), the weight ratio of the collected polymer to dried cells (P/C), and the number average molecular weight (Mn), the weight average molecular weight (Mw), and the molecular weight distribution (Mw/Mn) of the resultant polymer are shown together in Table 4.

TABLE 4

| | Productivity of polymer | | | | |
|---|---|---|---|---|---|
| CDW (mg/L) | PDW (mg/L) | P/C (%) | Mn (×10⁴) | Mw (×10⁴) | Mw/Mn |
| 920 | 370 | 40.2 | 4.9 | 12.3 | 2.5 |

<Synthesis of Aromatic Carboxy PHA by Oxidation Reaction (5)>

Polyhydroxyalkanoate obtained in the above Preparative Process 5 was utilized in the next reaction.

854 mg of polyhydroxyalkanoate was added to a 500 mL round bottomed flask, and then 60 mL of dichloromethane was added and dissolved. The mixture was placed in an ice bath, 9 mL of acetic acid and 3198 mg of 18-crown-6-ether were added followed by stirring. After 40 minutes, 2547 mg of potassium permanganate was gradually added followed by stirring in an ice bath for 1 hour and then at room temperature for 19 hours. After the reaction was completed, 100 mL of water and 6000 mg of sodium bisulfite were added. Then, the solution was made to be pH 1 by adding 1.0 N hydrochloric acid. After dichloromethane in the mixed solution was distilled off by an evaporator, the polymer in the solution was collected. The polymer was washed with 200 mL of methanol and then with 200 mL of pure water 3 times followed by collecting the polymer. Then, the resultant polymer was dialyzed by using chloroform for purification. After purification, 1037 mg of the polymer was obtained by drying under a reduced pressure.

The construction of the resultant polymer was determined by measuring the product obtained by reacting the resultant polymer and trimethylsilyldiazomethane by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature) to find that the polymer was a polyhydroxyalkanoate copolymer containing units represented by the following formula (29)

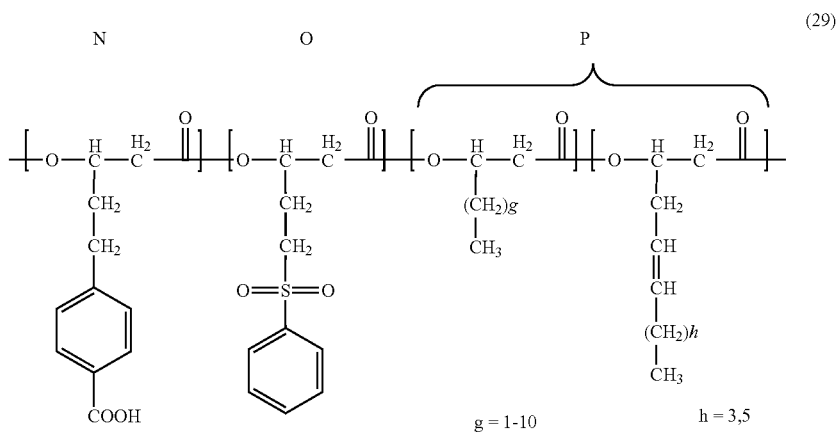

(29)

(g and h may take any one or more integer values within the range shown in the chemical formula. When there are a plurality of monomer units, each monomer unit independently represents the above meaning.) in a content ratio (mol %) of N:O:P=16:78:6.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 24300, and the weight average molecular weight Mw was 52600.

By scaling up the above preparation method, 50 g of PHA was obtained and it was referred to as PHA(A-5).

Example A-6

<Preparative Process 6: Biosynthesis of Aromatic Vinyl PHA (6)>

Polyhydroxyalkanoate containing 8.5 mol % of a 3-hydroxy-ω-(4-vinylphenyl)valeric acid unit, 89.4 mol % of a 3-hydroxy-5-phenylvaleric acid unit, and 1.1 mol % of the others (straight-chained 3-hydroxyalkanoic acid and 3-hydroxyalkenoic acid having 4 to 12 carbon atoms) was obtained in the same manner as in Example A-1.

<Synthesis of Aromatic Carboxy PHA by Oxidation Reaction (6)>

2999 mg of polyhydroxyalkanoate containing 8.5 mol % of a 3-hydroxy-ω-(4-vinylphenyl)valeric acid unit, 89.4 mol % of a 3-hydroxy-5-phenylvaleric acid unit, and 1.1 mol % of the others (straight-chained 3-hydroxyalkanoic acid and 3-hydroxyalkenoic acid having 4 to 12 carbon atoms) synthesized in Preparative Process 6 was added to a 500 mL round bottomed flask, and then 180 mL of acetone was added and dissolved. The mixture was placed in an ice bath, 30 mL of acetic acid and 1198 mg of 18-crown-6-ether were added followed by stirring. Next, 957 mg of potassium permanganate was gradually added to the flask in an ice bath followed by stirring in the ice bath for 2 hours and then at room temperature for 18 hours. After the reaction was completed, 100 mL of chloroform, 50 mL of water, and 2000 mg of sodium bisulfite were added. Then, the solution was made to be pH 1 by adding 1.0 mol/L (1.0 N) hydrochloric acid. After stirring for 1 hour, acetone and chloroform in the mixed solvent were distilled off by an evaporator, and the polymer in the solution was collected. The polymer was washed with 200 mL of pure water, 200 mL of methanol, 200 mL of pure water 3 times, and 200 mL of methanol in this order followed by collecting the polymer. The resultant polymer was dissolved in 20 mL of chloroform and 3 mL of methanol, and dialyzed in a 2 L beaker containing 900 mL of chloroform and 100 mL of methanol for a whole day by using a dialysis membrane (from Spectrum, Spectra/Por Standard Regenerated Cellulose Dialysis Membrane 3). The solution in the dialysis membrane was collected and dried under a reduced pressure to obtain 2998 mg of the desired product of PHA.

The construction of the resultant PHA was determined by analyzing $^1$H-NMR (FT-NMR: Bruker DPX400; resonance frequency: 400 MHz; measurement nuclear species: $^1$H; solvent used: dDMSO; measurement temperature: room temperature) to find that the polymer was PHA containing a 3-hydroxy-ω-(4-carboxyphenyl)valeric acid unit and a 3-hydroxy-5-phenylvaleric acid unit as monomer units.

Further, in order to calculate the units of the resultant PHA, the calculation was performed by methyl-esterifying a carboxyl group on the end of the side chain of PHA by using trimethylsilyldiazomethane as follows.

62 mg of the desired product of PHA was added to a 100 mL round bottomed flask, and 4.2 mL of chloroform and 1.4 mL of methanol were added and dissolved. To the mixture, 0.6 mL of a 2 mol/L trimethylsilyldiazomethane-hexane solution (from Aldrich) was added followed by stirring at room temperature for 30 minutes. After the reaction was completed, the solvent was distilled off by an evaporator, and then the polymer was collected. Further, after washing with 50 mL of methanol, the polymer was collected. 61 mg of PHA was obtained by drying under a reduced pressure.

NMR analysis performed in the same manner as in the above showed that the resultant PHA contained 6.7 mol % of a 3-hydroxy-ω-(4-carboxyphenyl)valeric acid unit, 91.8 mol % of a 3-hydroxy-5-phenylvaleric acid unit, and 1.5 mol % of the others (straight-chained 3-hydroxyalkanoic acid and 3-hydroxyalkenoic acid having 4 to 12 carbon atoms).

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 30500, and the weight average molecular weight Mw was 65000.

Example A-7

<Preparative Process 7: Biosynthesis of Aromatic Vinyl PHA (7)>

Polyhydroxyalkanoate containing 6.5 mol % of a 3-hydroxy-ω-(4-vinylphenyl)valeric acid unit, 92.2 mol % of a 3-hydroxy-5-phenylvaleric acid unit, and 1.3 mol % of the others (straight-chained 3-hydroxyalkanoic acid and 3-hydroxyalkenoic acid having 4 to 12 carbon atoms) was obtained in the same manner as in Example A-1.

<Synthesis of Aromatic Carboxy PHA by Oxidation Reaction (7)>

3000 mg of polyhydroxyalkanoate containing 6.5 mol % of a 3-hydroxy-ω-(4-vinylphenyl)valeric acid unit, 92.2 mol % of a 3-hydroxy-5-phenylvaleric acid unit, and 1.3 mol % of the others (straight-chained 3-hydroxyalkanoic acid and 3-hydroxyalkenoic acid having 4 to 12 carbon atoms) synthesized in Preparative Process 7 was added to a 500 mL round bottomed flask, and then 180 mL of acetone was added and dissolved. The mixture was placed in an ice bath, and 30 mL of acetic acid and 31 mg of 18-crown-6-ether were added followed by stirring. Next, 740 mg of potassium permanganate was gradually added in an ice bath followed by stirring in the ice bath for 2 hours and then at room temperature for 18 hours. After the reaction was completed, 100 mL of chloroform, 100 mL of water, and 2067 mg of sodium bisulfite were added. Then, the solution was made to be pH 1 by adding 1.0 mol/L (1.0 N) hydrochloric acid. After stirring for 1 hour, the organic layer was extracted. The extract was subjected to distillation by an evaporator, and the polymer was collected. The polymer was washed with 200 mL of pure water, 200 mL of methanol, 200 mL of pure water 3 times, and 200 mL of methanol in this order followed by collecting the polymer. The resultant polymer was dissolved in 20 mL of chloroform and 3 mL of methanol, and dialyzed in a 2 L beaker containing a mixed solvent of 900 mL of chloroform and 100 mL of methanol for a whole day by using a dialysis membrane (from Spectrum, Spectra/Por Standard Regenerated Cellulose Dialysis Membrane 3). The solution in the dialysis membrane was collected and dried under a reduced pressure to obtain 2859 mg of the desired product of PHA.

The construction of the resultant PHA was determined by analyzing $^1$H-NMR (FT-NMR: Bruker DPX400; resonance frequency: 400 MHz; measurement nuclear species: $^1$H; solvent used: dDMSO; measurement temperature: room temperature) to find that the polymer was PHA containing a 3-hydroxy-ω-(4-carboxyphenyl)valeric acid unit and a 3-hydroxy-5-phenylvaleric acid unit as monomer units.

Further, in order to calculate the units of the resultant PHA, the calculation was performed by methyl-esterifying a carboxyl group on the end of the side chain of PHA by using trimethylsilyldiazomethane.

60 mg of the desired product of PHA was added to a 100 mL round bottomed flask, and 4.2 mL of chloroform and 1.4 mL of methanol were added and dissolved. To the mixture, 0.5 mL of a 2 moL/L trimethylsilyldiazomethane-hexane solution (from Aldrich) was added followed by stirring at room temperature for 30 minutes. After the reaction was completed, the solvent was distilled off by an evaporator, and then the polymer was collected. Further, after washing with 50 mL of methanol, the polymer was collected. 58 mg of PHA was obtained by drying under a reduced pressure.

NMR analysis performed in the same manner as in the above showed that the resultant PHA contained 5.5 mol % of a 3-hydroxy-ω-(4-carboxyphenyl)valeric acid unit, 94.1 mol % of a 3-hydroxy-5-phenylvaleric acid unit, and 0.4 mol % of the others (straight-chained 3-hydroxyalkanoic acid and 3-hydroxyalkenoic acid having 4 to 12 carbon atoms).

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 31000, and the weight average molecular weight Mw was 64000.

Example A-8

<Preparative Process 8: Biosynthesis of Aromatic Vinyl PHA (8)>

Polyhydroxyalkanoate containing 6.9 mol % of a 3-hydroxy-ω-(4-vinylphenyl)valeric acid unit, 93.0 mol % of a 3-hydroxy-5-phenylvaleric acid unit, and 0.1 mol % of the others (straight-chained 3hydroxyalkanoic acid and 3-hydroxyalkenoic acid having 4 to 12 carbon atoms) was obtained in the same manner as in Example A-1.

<Synthesis of Aromatic Carboxy PHA by Oxidation Reaction (8)>

132.20 g of polyhydroxyalkanoate containing 6.9 mol % of a 3-hydroxy-ω-(4-vinylphenyl)valeric acid unit, 93.0 mol % of a 3-hydroxy-5-phenylvaleric acid unit, and 0.1 mol % of the others (straight-chained 3-hydroxyalkanoic acid and 3-hydroxyalkenoic acid having 4 to 12 carbon atoms) synthesized in Preparative Process 8 was added to a 3 L four-necked flask, and then 1586 mL of acetone was added and dissolved. The mixture was placed in an ice bath, and 264 mL of acetic acid and 1.35 g of 18-crown-6-ether were added followed by stirring. Next, 32.34 g of potassium permanganate was gradually added to the flask in an ice bath followed by stirring in an ice bath for 2 hours and then at room temperature for 3 hours. After allowing to stand then at room temperature overnight, the mixture was stirred at room temperature for 3 hours again. After the reaction was completed, 3966 mL of ethyl acetate, 1983 mL of water, and 73.40 g of sodium bisulfite were added. Then, the solution was made to be pH 1 by adding 1.0 mol/L.(1.0 N) hydrochloric acid. After stirring for 1 hour, the organic layer was extracted. The extract was subjected to distillation by an evaporator, and then polymer was collected. The polymer was washed with 8.4 L of pure water, 8.4 L of methanol, 8.4 L of pure water 3 times, and 8.4 L of methanol in this order followed by collecting the polymer. The resultant polymer was dissolved in 986 mL of tetrahydrofuran, and dialyzed in a 50 L stainless vat containing 32 L of methanol for a whole day by using a dialysis membrane (from Spectrum, Spectra/Por Standard Regenerated Cellulose Dialysis Membrane 3). The polymer in the dialysis membrane was collected, dissolved in 986 mL of tetrahydrofuran again, and dialyzed in a 50 L stainless vat containing 32 L of methanol for a whole day by using a dialysis membrane (from Spectrum, Spectra/Por Standard Regenerated Cellulose Dialysis Membrane 3). The polymer in the dialysis membrane was collected and dried under a reduced pressure to obtain 120.6 g of the desired product of PHA.

The construction of the resultant PHA was determined by analyzing $^1$H-NMR (FT-NMR: Bruker DPX400; resonance frequency: 400 MHz; measurement nuclear species: $^1$H; solvent used: dDMSO; measurement temperature: room temperature) to find that the polymer was PHA containing a 3-hydroxy-ω-(4-carboxyphenyl)valeric acid unit and a 3-hydroxy-5-phenylvaleric acid unit as monomer units.

Further, in order to calculate the units of the resultant PHA, the calculation was performed by methyl-esterifying a carboxyl group on the end of the side chain of PHA by using trimethylsilyldiazomethane as follows.

61 mg of the desired product of PHA was added to a 100 mL round bottomed flask, and 4.2 mL of chloroform and 1.4 mL of methanol were added and dissolved. To the mixture, 0.5 mL of a 2 mol/L trimethylsilyldiazomethane-hexane solution (from Aldrich) was added followed by stirring at room temperature for 30 minutes. After the reaction was completed, the solvent was distilled off by an evaporator, and then the polymer was collected. After washing with 50 mL of methanol, the polymer was collected. 60 mg of PHA was obtained by drying under a reduced pressure.

NMR analysis performed in the same manner as in the above showed that the resultant PHA contained 5.7 mol % of a 3-hydroxy-ω-(4-carboxyphenyl)valeric acid unit, 92.0 mol % of a 3-hydroxy-5-phenylvaleric acid unit, and 2.3 mol % of the others (straight-chained 3-hydroxyalkanoic acid and 3-hydroxyalkenoic acid having 4 to 12 carbon atoms).

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 30000, and the weight average molecular weight Mw was 62000.

Example A-9

<Preparative Process 9: Biosynthesis of Aromatic Vinyl PHA (9)>

Polyhydroxyalkanoate containing 7.0 mol % of a 3-hydroxy-ω-(4-vinylphenyl)valeric acid unit and 93.0 mol % of a 3-hydroxy-5-phenylvaleric acid unit was obtained in the same manner as in Example A-1.

<Synthesis of Aromatic Carboxy PHA by Oxidation Reaction (9)>

500 mg of polyhydroxyalkanoate containing 7.0 mol % of a 3-hydroxy-ω-(4-vinylphenyl)valeric acid unit and 93.0 mol % of a 3-hydroxy-5-phenylvaleric acid unit synthesized in Preparative Process 9 was charged in a 500 mL three-necked flask, and 150 mL of distilled water with 50 ppm of hydrogen peroxide added thereto was added to suspend. Ozone was bubbled into the suspension at 50 mg/hour followed by stirring at room temperature for 3 hours.

After the reaction was completed, the reaction solution was filtered to collect the polymer. After the polymer was resuspended in distilled water, the residual hydrogen peroxide was washed by centrifugation. Further, the collected polymer was dissolved in tetrahydrofuran, and dialysis using methanol was repeated three times to purify the polymer. The polymer was dried under a reduced pressure to obtain 455 mg of the desired product of PHA.

The construction of the resultant polymer was determined by $^1$H-NMR (FT-NMR: Bruker DPX400; resonance frequency: 400 MHz; measurement nuclear species: $^1$H; solvent used: CDCl$_3$; measurement temperature: room temperature) and analyzed by Fourier transform infrared absorption (FT-IR) spectrum (Nicolet AV ATAR360 FT-IR). As the result, an additional absorption derived from carboxylic acid was found at 1693 cm$^{-1}$, and hence it was found that the resultant PHA had a 3-hydroxy-ω-(4-carboxyphenyl)valeric acid unit.

Further, the product obtained by reacting the resultant polymer and trimethylsilyldiazomethane was measured by $^1$H-NMR (FT-NMR: Bruker DPX400; resonance frequency: 400 MHz; measurement nuclear species: $^1$H; solvent used: deuterated chloroform; measurement temperature: room temperature), and the result showed that the resultant PHA contained 6 mol % of a 3-hydroxy-ω-(4-carboxyphenyl)valeric acid unit and 94.0 mol % of a 3-hydroxy-5-phenylvaleric acid unit.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 39000, and the weight average molecular weight Mw was 62000.

Example A-10

<Preparative Process 10: Biosynthesis of Aromatic PHA (10)>

5-(4-Methylphenyl)valeric acid was synthesized in accordance with the method described in Macromolecules, 29, 1762-1766 (1996).

5.0 g of polypeptone (Wako Pure Chemicals Industries, Ltd.), 1.0 g of 5-phenylvaleric acid, and 0.2 g of 5-(4-methylphenyl)valeric acid were added to 1000 mL of an M9 culture medium, charged in a 2000 mL shaking flask, and sterilized by an autoclave to prepare a culture medium

*Pseudomonas cichorii* YN2 was inoculated in an M9 culture medium containing 0.5% of polypeptone and shake-cultured at 30° C. for 8 hours to prepare a preculture solution. 10 mL of this culture solution was added to the above culture medium containing 0.9 g of 5-phenylvaleric acid and 5-(4-methylphenyl)valeric acid as substrates to culture the cells at 30° C. for 40 hours. After being cultured, the cells were collected by centrifugation, washed with methanol, and then lyophilized.

After dried cells were weighed, chloroform was added. The mixture was stirred at 25° C. for 72 hours, thereby extracting the polymer accumulated in the cell. The polymer was filtered, and the filtrate was concentrated by an evaporator, followed by redissolving the polymer in acetone and filtering off insoluble components. Then, the filtrate was concentrated by an evaporator, and precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature) to find that the polymer was a polyhydroxyalkanoate copolymer containing two units represented by the following formula (30)

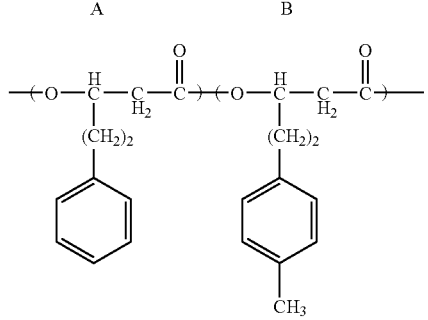

in a content ratio (mol %) of A:B=93:7.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

The dry weight of cells obtained in the above step (CDW), the dry weight of the collected polymer (PDW), the weight ratio of the collected polymer to dried cells (P/C), and the number average molecular weight (Mn), the weight average molecular weight (Mw), and molecular weight distribution (Mw/Mn) of the resultant polymer are shown together in Table 5.

TABLE 5

| CDW (mg/L) | PDW (mg/L) | P/C (%) | Mn (×10$^4$) | Mw (×10$^4$) | Mw/Mn |
|---|---|---|---|---|---|
| 880 | 410 | 46.6 | 6.9 | 15.6 | 2.3 |

<Synthesis of Aromatic Carboxy PHA by Oxidation Reaction (10)>

500 mg of polyhydroxyalkanoate containing 7.0 mol % of a 3-hydroxy-ω-(4-methylphenyl)valeric acid unit and 93.0 mol % of a 3-hydroxy-5-phenylvaleric acid unit synthesized in Preparative Process 10, 156.22 mg of 18-crown-6-ether, 32.5 mL of dichloromethane, and 5.5 mL of acetic acid were charged in a 500 mL flask followed by stirring. The flask was dipped in an ice bath, and the reaction system was made 0° C. After 60 minutes, 125 mg of potassium permanganate was added followed by stirring 20 hours. After the reaction was completed, 5% aqueous sodium bisulfite was added followed by stirring, and then the solution was made pH 1 by adding 1.0 N hydrochloric acid. After dichloromethane in the mixed solution was distilled off by an evaporator, the polymer in the solution was collected. Then, the resultant polymer was washed with 200 mL of pure water and then 200 mL of methanol. Further, after the polymer was washed with 100 mL of pure water and with 100 mL of methanol once, the polymer was collected.

The collected polymer was dissolved in tetrahydrofuran, and the polymer was purified by repeating dialysis three times using methanol and dried under a reduced pressure to obtain 480 mg of the desired product of PHA.

The structure of the resultant polymer was determined by $^1$H-NMR (FT-NMR: Bruker DPX400; resonance frequency: 400 MHz; measurement nuclear species: $^1$H; solvent used: CDCl$_3$; measurement temperature: room temperature) and analyzed by Fourier transform infrared absorption (FT-IR) spectrum (Nicolet AV ATAR360 FT-IR). As the result, an additional absorption derived from carboxylic acid was found at 1693 cm$^{-1}$, and hence it was found that the resultant PHA had a 3-hydroxy-ω-(4-carboxyphenyl)valeric acid unit.

Further, the product obtained by reacting the resultant polymer and trimethylsilyldiazomethane was measured by $^1$H-NMR (FT-NMR: Bruker DPX400; resonance frequency: 400 MHz; measurement nuclear species: $^1$H; solvent used: deuterated chloroform; measurement temperature: room temperature), and hence it was found that the resultant PHA had 6.0 mol % of a 3-hydroxy-ω-(4-carboxyphenyl)valeric acid unit and 94.0 mol % of a 3-hydroxy-5-phenylvaleric acid unit.

Moreover, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 33000, and the weight average molecular weight Mw was 69000.

Example A-11

<Preparative Process 11: Biosynthesis of Aromatic PHA (11)>

5.0 g of polypeptone (Wako Pure Chemicals Industries, Ltd.), 0.205 g of 5-(4-vinylphenyl)valericacid, and 1.160 g of 5-phenoxyvaleric acid were added to 1000 mL of an M9 culture medium, charged in a 2000 mL shaking flask, and sterilized by an autoclave. After the above heat sterilization treatment, the mixture was cooled to room temperature to prepare a culture medium. (Total six flasks of this culture medium were prepared.) *Pseudomonas cichorii* YN2 was inoculated in an M9 culture medium containing 0.5% of polypeptone and shake-cultured at 30° C. for 8 hours to prepare a preculture solution. 10 mL of this culture solution was added to the above culture medium containing 5-(4-vinylphenyl)valeric acid and 5-phenoxyvaleric acid as substrates to culture the cells at 30° C. for 40 hours. After being cultured, the cells were collected by centrifugation, washed with methanol, and then lyophilized.

After dried cells were weighed, chloroform was added. The mixture was stirred at 35° C. for 17 hours, thereby extracting the polymer accumulated in the cell. The chloroform solution with the extracted polymer dissolved therein was filtered. The chloroform filtrate was concentrated by an evaporator, followed by redissolving the polymer in acetone and filtering off insoluble components. Then, the filtrate was concentrated by an evaporator, and precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/$CDCl_3$; measurement temperature: room temperature) to find that the polymer was a polyhydroxyalkanoate copolymer containing three units represented by the following formula (31)

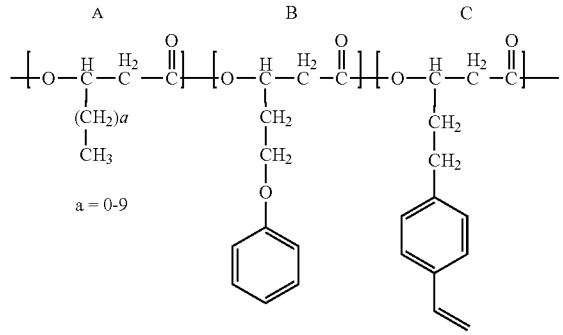

in a content ratio (mol %) of A:B:C=8:69:23.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

The dry weight of cells obtained in the above step (CDW), the dry weight of the collected polymer (PDW), the weight ratio of the collected polymer to dried cells (P/C), and the number average molecular weight (Mn), the weight average molecular weight (Mw), and the molecular weight distribution (Mw/Mn) of the resultant polymer are shown together in Table 6.

TABLE 6

| CDW (mg/L) | PDW (mg/L) | P/C (%) | Mn ($\times 10^4$) | Mw ($\times 10^4$) | Mw/Mn |
|---|---|---|---|---|---|
| 590 | 192 | 32.5 | 5.1 | 10.2 | 2.0 |

<Synthesis of Aromatic Carboxy PHA by Cleavage Reaction (11)>

Polyhydroxyalkanoate obtained in the above Preparative Process 11 was utilized in the next reaction.

1000 mg of polyhydroxyalkanoate was charged in a 500 mL round bottomed flask, and 65 mL of dichloromethane was added and dissolved. The flask was placed in an ice bath, and 11 mL of acetic acid and 967 mg of 18-crown-6-ether were added followed by stirring. After 40 minutes, 771 mg of potassium permanganate was gradually added followed by stirring in an ice bath for 1 hour and then at room temperature for 19 hours. After the reaction was completed, 100 mL of water and 5000 mg of sodium bisulfite were added. Then, the solution was made pH 1 by adding 1.0 N hydrochloric acid. After dichloromethane in the mixed solution was distilled off by an evaporator, the polymer in the solution was collected. The polymer was washed with 200 mL of methanol and 200 mL of pure water 3 times, and then the polymer was collected. Thus obtained polymer was purified by dialysis using chloroform. After purification, 950 mg of the polymer was obtained by drying under a reduced pressure.

The structure of the resultant polymer was determined by analysis by Fourier transform infrared absorption (FT-IR) spectrum (Nicolet AV ATAR360 FT-IR). As the result, an additional absorption derived from carboxylic acid was found at 1693 cm$^{-1}$, and hence it was found that the resultant polyhydroxyalkanoate had a 3-hydroxy-ω-(4-carboxyphenyl)valeric acid unit. Further, the product obtained by reacting the resultant polymer and trimethylsilyldiazomethane was measured by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/$CDCl_3$; measurement temperature: room temperature), and hence it was found that the polymer was a polyhydroxyalkanoate copolymer containing units represented by the following formula (32)

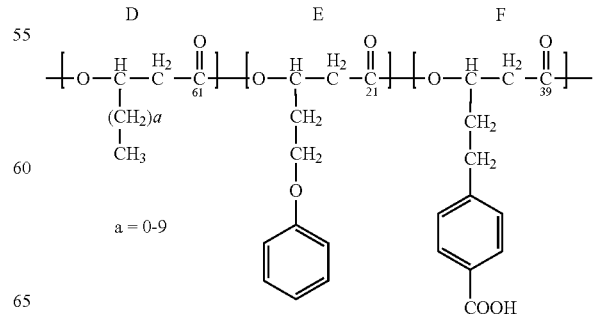

(a may take any one or more integer values within the range shown in the chemical formula. When there are a plurality of monomer units, each monomer unit independently represents the above meaning.) in a content ratio (mol %) of D:E:F=9:70:21.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 30100, and the weight average molecular weight Mw was 65400.

Example A-12

<Preparative Process 12: Biosynthesis of Aromatic PHA (12)>

5.0 g of polypeptone (Wako Pure Chemicals Industries, Ltd.), 0.205 g of 5-(4-vinylphenyl)valeric acid, and 1.020 g of 4-cyclohexybutyric acid were added to 1000 mL of the above M9 culture medium, charged in a 2000 mL shaking flask, and sterilized by an autoclave. After the above heat sterilization treatment, the mixture was cooled to room temperature to prepare a culture medium. (Total ten flasks of this culture medium were prepared.)

*Pseudomonas cichorii* YN2 was inoculated in the above culture medium containing 5-(4-vinylphenyl)valeric acid and 4-cyclohexylbutyric acid as substrates and cultured at 30° C. for 41 hours. After being cultured, cells were collected by centrifugation, washed with methanol, and then lyophilized.

After dried cells were weighed, chloroform was added. The mixture was stirred at 35° C. for 15 hours, thereby extracting the polymer accumulated in the cell. The chloroform solution with the extracted polymer dissolved therein was filtered. After the chloroform filtrate was concentrated by an evaporator, precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature) to find that the polymer was a polyhydroxyalkanoate copolymer containing three units represented by the following formula (33)

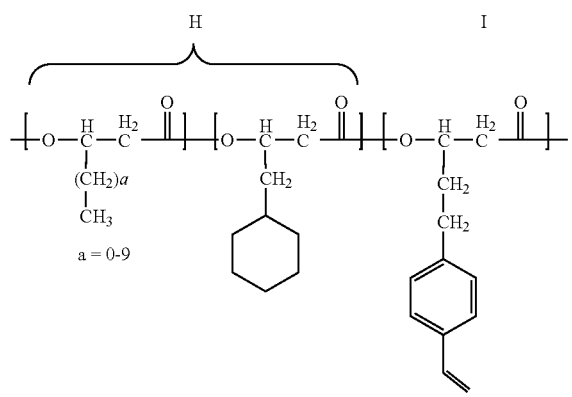

in a content ratio (mol %) of H:I=37:63.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

The dry-weight of cells obtained in the above step (CDW), the dry weight of the collected polymer (PDW), the weight ratio of the collected polymer to dried cells (P/C), and the number average molecular weight (Mn), the weight average molecular weight (Mw), and the molecular weight distribution (Mw/Mn) of the resultant polymer are shown together in Table 7.

TABLE 7

| CDW (mg/L) | PDW (mg/L) | P/C (%) | Mn (×10$^4$) | Mw (×10$^4$) | Mw/Mn |
|---|---|---|---|---|---|
| 724 | 159 | 22.0 | 5.4 | 12.3 | 2.3 |

<Synthesis of Aromatic Carboxy PHA by Cleavage Reaction (12)>

Polyhydroxyalkanoate obtained in the above Preparative Process 12 was utilized in the next reaction.

1000 mg of polyhydroxyalkanoate was charged in a 500 mL round bottomed flask, and 65 mL of dichloromethane was added and dissolved. The flask was placed in an ice bath, and 11 mL of acetic acid and 2883 mg of 18-crown-6-ether were added followed by stirring. After 40 minutes, 2299 mg of potassium permanganate was gradually added followed by stirring in an ice bath for 1 hour and then at room temperature for 19 hours. After the reaction was completed, 100 mL of water and 7000 mg of sodium bisulfite were added. Then, the solution was made pH 1 by adding 1.0 N hydrochloric acid. After dichloromethane in the mixed solution was distilled off by an evaporator, the polymer in the solution was collected. The polymer was washed with 200 mL of methanol and 200 mL of pure water 3 times, and then the polymer was collected. Thus obtained polymer was purified by dialysis using chloroform. After purification, 938 mg of the polymer was obtained by drying under a reduced pressure.

The structure of the resultant polymer was determined by analysis by Fourier transform infrared absorption (FT-IR) spectrum (Nicolet AV ATAR360 FT-IR). As the result, an additional absorption derived from carboxylic acid was found at 1693 cm$^{-1}$, and hence it was found that the resultant polyhydroxyalkanoate had a 3-hydroxy-ω-(4-carboxyphenyl)valeric acid unit. Further, the product obtained by reacting the resultant polymer and trimethylsilyldiazomethane was measured by $^1$H-NMR (FT-NMR: Bruker DPX400; $^1$H resonance frequency: 400 MHz; measurement nuclear species: $^1$H; solvent used: CDCl$_3$; reference: capillary-encapsulated TMS/CDCl$_3$; measurement temperature: room temperature), and hence it was found that the polymer was a polyhydroxyalkanoate copolymer containing units represented by the following formula (34)

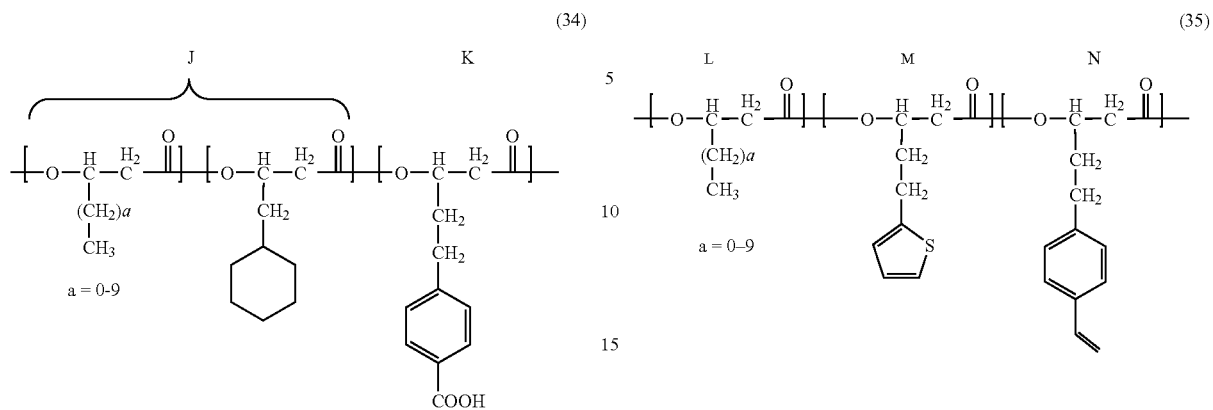

(a may take any one or more integer values within the range shown in the chemical formula. When there are a plurality of monomer units, each monomer unit independently represents the above meaning.) in a content ratio (mol %) of J:K=39:61.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 45300, and the weight average molecular weight Mw was 91200.

Example A-13

<Preparative Process 13: Biosynthesis (13) of Aromatic PHA>

5.0 g of polypeptone (Wako Pure Chemicals Industries, Ltd.), 0.205 g of 5-(4-vinylphenyl)valeric acid, and 1.105 g of 5-(2-thienyl)valeric acid were added to 1000 mL of the above M9 culture medium, charged in a 2000 mL shaking flask, and sterilized by an autoclave. After the above heat sterilization treatment, the mixture was cooled to room temperature to prepare a culture medium. (Total three flasks of this culture medium were prepared.)

The above culture medium containing 5-(4-vinylphenyl) valeric acid and 5-(2-thienyl)valeric acid as substrates was inoculated with *Pseudomonas cichorii* YN2 and cultured at 30° C. for 41 hours. After being cultured, cells were collected by centrifugation, washed with methanol, and then lyophilized.

After dried cells were weighed, chloroform was added. The mixture was stirred at 35° C. for 15 hours, to extract the polymer accumulated in the cell. The chloroform solution with the extracted polymer dissolved therein was filtered. After the chloroform filtrate was concentrated by an evaporator, precipitated solid components were collected with cold methanol. The components were dried under a reduced pressure to collect the desired polymer. The dry weight of the polymer collected in the above collection step was measured.

The structure of the collected polymer was determined by $^1$H-NMR (FT-NMR: Bruker DPX400; $^1$H resonance frequency: 400 MHz; measurement nuclear species: $^1$H; solvent used: $CDCl_3$; reference: capillary-encapsulated TMS/$CDCl_3$; measurement temperature: room temperature) to find that the polymer was a polyhydroxyalkanoate copolymer containing three units represented by the following formula (35)

in a content ratio (mol %) of L:M:N=4:79:17.

In addition, the average molecular weight of the polymer was measured by gel permeation chromatography (GPC) (Tosoh HLC-8220 GPC; column: Tosoh TSK-GEL SuperHM-H; solvent; chloroform; polystyrene equivalent).

The dry weight of cells obtained in the above step (CDW), the dry weight of the collected polymer (PDW), the weight ratio of the collected polymer to dried cells (P/C), and the number average molecular weight (Mn), the weight average molecular weight (Mw), and the molecular weight distribution (Mw/Mn) of the resultant polymer are shown together in Table 8.

TABLE 8

| CDW (mg/L) | PDW (mg/L) | P/C (%) | Mn (×10$^4$) | Mw (×10$^4$) | Mw/Mn |
|---|---|---|---|---|---|
| 898 | 485 | 54.0 | 7.4 | 19.2 | 2.6 |

<Synthesis (13) of Aromatic Carboxy PHA by Cleavage Reaction>

Polyhydroxyalkanoate obtained in the above Preparative Process 13 was utilized in the next reaction.

1000 mg of polyhydroxyalkanoate was charged in a 500 mL round bottomed flask, and 65 mL of dichloromethane was added to dissolve it. The flask was placed in an ice bath, and 11 mL of acetic acid and 744 mg of 18-crown-6-ether were added followed by stirring. After 40 minutes, 593 mg of potassium permanganate was gradually added followed by stirring in an ice bath for 1 hour and then at room temperature for 19 hours. After the reaction was completed, 100 mL of water and 5000 mg of sodium bisulfite were added. Then, the solution was made pH 1 by adding 1.0 N hydrochloric acid. After dichloromethane in the mixed solution was distilled off by an evaporator, the polymer in the solution was collected. The polymer was washed with 200 mL of methanol and 200 mL of pure water 3 times, and then the polymer was collected. Thus obtained polymer was purified by dialysis using chloroform. After purification, 945 mg of the polymer was obtained by drying under a reduced pressure.

The structure of the resultant polymer was determined by analysis by Fourier transform infrared absorption (FT-IR) spectrum (Nicolet AV ATAR360 FT-IR). As the result, an additional absorption derived from carboxylic acid was found at 1693 cm$^{-1}$, and hence it was found that the resultant polyhydroxyalkanoate had a 3-hydroxy-ω-(4-carboxyphenyl)valeric acid unit. Further, the product obtained by reacting the resultant polymer and trimethylsilyldiazomethane was measured by $^1$H-NMR (FT-NMR: Bruker DPX400; $^1$H resonance frequency: 400 MHz; measurement nuclear species: ¹H; solvent used: CDCl₃; reference: capillary-encapsulated TMS/CDCl₃; measurement temperature: room temperature), and hence it was found that the polymer was a polyhydroxyalkanoate copolymer containing units represented by the following formula (36)

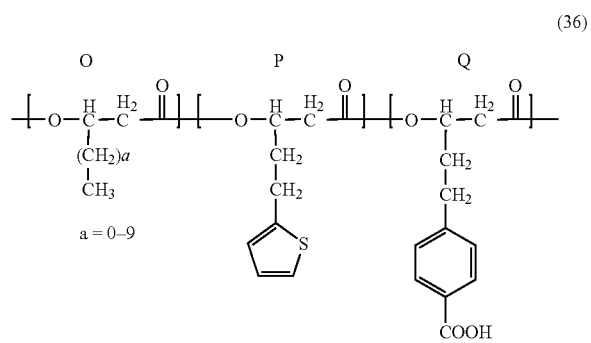

(a may take any one or more integer values within the range shown in the chemical formula. When there are a plurality of monomer units, each monomer unit independently represents the above meaning.) in a content ratio (mol %) of O:P:Q=5:80:15.

Further, with respect to the product obtained by reacting the resultant polymer and trimethylsilyldiazomethane, the average molecular weight was evaluated by gel permeation chromatography (GPC; Tosoh HLC-8220, column: Tosoh TSK-GEL SuperHM-H; solvent; chloroform; polystyrene equivalent), and hence it was found that the number average molecular weight Mn was 62400, and the weight average molecular weight Mw was 143500.

Comparative Preparation Example A

*Pseudomonas cichorii* H45 was inoculated in 200 mL of an M9 culture medium containing 0.5% of a yeast extract (from Oriental Yeast Co., Ltd.) and shake-cultured at 30° C. and 125 strokes/minute for 8 hours to prepare a seed culture. 25 L of an M9 culture medium containing 0.1% of 5-phenylvaleric acid and 0.5% of D-glucose was prepared in a 50 L jar fermenter, and the seed culture was charged thereto and cultured with aeration and stirring at 30° C., 70 rpm, and 9.4 L/minute of an aeration amount. After 48 hours, the cells were collected by centrifugation, resuspended in 25 L of an M9 culture medium containing 0.1% of 5-phenylvaleric acid and 0.5% of D-glucose and not containing a nitrogen source (NH₄Cl), and further cultured with aeration and stirring at 30° C., 70 rpm, and 9.4 L/minute of an aeration amount. After 48 hours, the cells were collected by centrifugation, washed once with cold methanol, and lyophilized.

The lyophilized pellets were suspended in 200 mL of chloroform, stirred at 60° C. for 20 hours, and extracted. After filtered by a membrane filter of the pore size of 0.45 μm, the extract was concentrated by a rotary evaporator. The concentrated solution was reprecipitated in cold methanol, and only the precipitate was collected and dried under vacuum to obtain 15.0 g of a resin composition.

A portion of the resin composition was taken, subjected to methanolysis in the usual manner and then analyzed by using a Gas Chromatography-Mass Spectrometer (GC-MS, Shimadzu QP-5050, EI method) to identify the methyl-esterified product of the monomer unit composing the resin composition. As the result, the resin composition was found to be comprised of PHA containing a 3-hydroxy-5-phenylvaleric acid unit only.

[Molded Product of Resin Composition]

PHA of the above Examples and Comparative Preparation Example A, or a resin composition containing thereof were molded to evaluate degradability and performance as a molded product as follows (Examples B-1 to B-4, Comparative Examples B-1 to B-4).

Example B-1

Foamed extruded sheets were molded by using resin compositions described in Examples A-1 and A-3 to A-5 (PHA (A-1) and (A-3) to (A-5)) and subjected to a second molding to produce instant noodle containers 1 to 4. Meanwhile, the resin compositions described in Examples A-1 and A-3 to A-5 and a polystyrene polymer (Styron 685, from Asahi Kasei Corporation) were blended in a mass ratio of 75:25 to produce instant noodle containers 5 to 8 in the same manner. They were also blended in a mass-ratio of 51:49 in the same manner to produce instant noodle containers 9 to 12 in the same manner. Each mass was 3.0 g per container.

Comparative Example B-1

Using the resin composition described in Comparative Preparation Example A, a foamed extruded sheet was molded and subjected to a second molding to produce an instant noodle container 13. Meanwhile, the resin composition described in Comparative Preparation Example A and a polystyrene polymer (Styron 685, from Asahi Kasei Corporation) were blended in mass ratios of 75:25 and 51:49 to produce instant noodle containers 14 and 15 in the same manner. Further, using only the above polystyrene polymer, an instant noodle container 16 was produced in the same manner. Each mass was 3.0 g per container.

Example B-2

Using resin compositions described in Examples A-1 and A-3 to A-5, drink containers 1 to 4 were produced by injection blow molding. Meanwhile, the resin compositions described in Examples A-1 and A-3 to A-5 and a lactone polymer (Polycaprolactone, from DAICEL CHEMICAL INDUSTRIES, LTD.) were blended in a mass ratio of 75:25 to produce drink containers 5 to 8 in the same manner. They were also blended in a mass ratio of 51:49 in the same manner to produce drink containers 9 to 12 in the same manner. Each mass was 3.0 g per container.

Comparative Example B-2

Using a resin composition described in Comparative Preparation Example A, a drink container 13 was produced by injection blow molding. Meanwhile, the resin composition described in Comparative Example A and a lactone polymer (Polycaprolactone, from DAICEL CHEMICAL INDUSTRIES, LTD.) were blended in mass ratios of 75:25 and 51:49 to produce drink containers 14 and 15 in the same manner. Further, using only the above lactone polymer, a drink container 16 was produced in the same manner. Each mass was 3.0 g per container.

Example B-3 and Comparative Example B-3

With respect to an instant noodle container described in Example B-1 or Comparative Example B-1, the following evaluation items were tested in order to compare and evaluate the quality as an instant noodle container. The results are shown in Table 9. A: good, B: usable, C: unusable, -: untested Biodegradability: It was checked visually whether or not to be almost invisible after buried for 6 months. It should be noted that B in the table indicates that resin residues were slightly recognized during the above period, and C indicates that there was not substantial biodegradation within this period. Quality as an instant noodle container: Hardness, brittleness, and fracture/leakage were evaluated at 25° C. (assuming the storage time) and 100° C. (assuming the time to pour hot water).

Tg and Tm: The measurements were performed by a differential scanning calorimeter (DSC; from PerkinElmer, Inc., Pyris 1, temperature elevation: 20° C./minute).

TABLE 9

Biodegradability and quality of instant noodle container

| Container | Biodegradability | 25° C. | | | 100° C. | | | Tg | Tm |
|---|---|---|---|---|---|---|---|---|---|
| | | Hardness | Brittleness | Fracture/leakage | Hardness | Brittleness | Fracture/leakage | | |
| 1 | A | A | A | A | A | A | A | 48 | 162 |
| 2 | A | A | A | A | A | A | A | 52 | 171 |
| 3 | A | A | A | A | A | A | A | 43 | 151 |
| 4 | A | A | A | A | A | A | A | 65 | 180 |
| 5 | A | A | A | A | A | A | A | — | — |
| 6 | A | A | A | A | A | A | A | — | — |
| 7 | A | A | A | A | A | A | A | — | — |
| 8 | A | A | A | A | A | A | A | — | — |
| 9 | B | A | A | A | A | A | A | — | — |
| 10 | B | A | A | A | A | A | A | — | — |
| 11 | B | A | A | A | A | A | A | — | — |
| 12 | B | A | A | A | A | A | A | — | — |
| 13 | A | C | — | — | C | — | — | 19 | 158 |
| 14 | A | B | A | B | C | — | — | — | — |
| 15 | B | B | A | B | C | — | — | — | — |
| 16 | C | A | A | A | A | A | A | 93 | 210 |

Example B-4 and Comparative Example B-4

With respect to the drink container described in Example B-2 or Comparative Example B-2, the following evaluation items were tested in order to compare and evaluate the quality as a drink container. The results are shown in Table 10.

A: good, B: usable, C: unusable, -: untested Biodegradability: It was checked visually whether or not to be almost invisible after buried for 6 months. It should be noted that B in the table indicates that resin residues were slightly recognized during the above periods and C indicates that there was not substantial biodegradation within the test period. Quality as a drink container: Hardness, brittleness, and fracture/leakage were evaluated at 25° C. (assuming the storage time) and 100° C. (assuming the time of heat sterilization).

Tg and Tm: The measurement was performed by a differential scanning calorimeter (DSC; from PerkinElmer, Inc., Pyris 1, temperature elevation: 20° C./minute).

TABLE 10

Biodegradability and quality of drink container

| Container | Biodegradability | 25° C. | | | 100° C. | | | Tg | Tm |
|---|---|---|---|---|---|---|---|---|---|
| | | Hardness | Brittleness | Fracture/leakage | Hardness | Brittleness | Fracture/leakage | | |
| 1 | A | A | A | A | A | A | A | 48 | 162 |
| 2 | A | A | A | A | A | A | A | 52 | 171 |
| 3 | A | A | A | A | A | A | A | 43 | 151 |
| 4 | A | A | A | A | A | A | A | 65 | 180 |
| 5 | A | A | A | A | A | A | A | — | — |
| 6 | A | A | A | A | A | A | A | — | — |

TABLE 10-continued

Biodegradability and quality of drink container

| | | 25° C. | | | 100° C. | | | | |
|---|---|---|---|---|---|---|---|---|---|
| Container | Biodegradability | Hardness | Brittleness | Fracture/leakage | Hardness | Brittleness | Fracture/leakage | Tg | Tm |
| 7 | A | A | A | A | A | A | A | — | — |
| 8 | A | A | A | A | A | A | A | — | — |
| 9 | A | A | A | A | A | A | A | — | — |
| 10 | A | A | A | A | A | A | A | — | — |
| 11 | A | A | A | A | B | A | C | — | — |
| 12 | A | A | A | A | A | A | A | — | — |
| 13 | A | C | — | — | C | — | — | 19 | 158 |
| 14 | A | C | — | — | C | — | — | — | — |
| 15 | A | C | — | — | C | — | — | — | — |
| 16 | A | C | — | — | C | — | — | — | 60 |

Besides the above Examples, the molded product of the present invention was experimented under conditions of 40° C. and 140° C., and it was found that the molded product does not have any problem in hardness, brittleness, and fracture/leakage, being excellent in biodegradability.

[Binder Resin]

Next, the polymer blend which is used as a binder resin of the present invention is shown as follows (Examples C-1 to C4).

Example C-1

80 g of polylactic acid (Lacty (trade name), from Shimadzu Corporation, melt viscosity at 195° C. 20,000 Pa·s (=200,000 poise), weight average molecular weight 200,000) and 120 g of PHA of Example A-1 (PHA(A-1)) were blended, charged in an injection molding machine, and melt-kneaded at 195 to 230° C. for molding. Thus obtained polymer blend was referred to as PHA(C-1) and used as a binder resin.

Example C-2

80 g of polylactic acid (Lacty (trade name), from Shimadzu Corporation, melt viscosity at 195° C. 20,000 Pa·s (=200,000 poise), weight average molecular weight 200,000) and 120 g of PHA of Example A-3 (PHA(A-3)) were blended, charged in an injection molding machine, and melt-kneaded at 195-230° C. for molding. Thus obtained polymer blend was referred to as PHA(C-2) and used as a binder resin.

Example C-3

80 g of polylactic acid (Lacty (trade name), from Shimadzu Corporation, melt viscosity at 195° C. 20,000 Pa·s (=200,000 poise), weight average molecular weight 200,000) and 120 g of PHA of Example A-4 (PHA(A-4)) were blended, charged in an injection molding machine, and melt-kneaded at 195 to 230° C. for molding. Thus obtained polymer blend was referred to as PHA(C-3) and used as a binder resin.

Example C-4

80 g of polylactic acid (Lacty (trade name), from Shimadzu Corporation, melt viscosity at 195° C. 20,000 Pa·s (=200,000 poise), weight average molecular weight 200,000) and 120 g of PHA of Example A-5 (PHA(A-5)) were blended, charged in an injection molding machine, and melt-kneaded at 195-230° C. for molding. Thus obtained polymer blend was referred to as PHA(C-4) and used as a binder resin.

Various toners were produced using the polymer blends of the above Examples C-1 to C-4 and a single PHA polymer (above Examples A-1 and A-3 to A-5) and conventional resiss for evaluation (Examples D-1 to D-8, Comparative Examples D-1 to D-2).

Example D-1

| | |
|---|---|
| PHA(A-1) | 100 parts by mass |
| Magenta pigment (C.I. Pigment Red 114) | 5 parts by mass |
| Charge controlling agent (from Hoechst AG: NXVP 434) | 2 parts by mass |

The above composition was mixed and melt-kneaded by a twin screw extruder (L/D=30). The resultant kneaded product was cooled, roughly ground by a hammer mill, finely ground by a jet mill, and then classified to obtain magenta colored particles (1) by a grinding method. For the particle size of the magenta colored particles (1), the weight average particle size was 8.3 μm and the ratio of fines (the abundance ratio of particles with the size of 3.17 μm or smaller in the number distribution) was 2.4% by number.

As a fluidity improver, 1.5 parts by mass of hydrophobic silica fine powder (BET: 250 m$^2$/g) treated with hexamethyldisilazane were dry-mixed with 100 parts by mass of the magenta colored particles (1) by a Henshel mixer, whereby a magenta toner (1) of this Example was obtained. Further, 7 parts by mass of the resultant magenta toner (1) were mixed with 93 parts by mass of a resin-coated magnetic ferrite carrier (average particle size: 45 μm) to prepare a two-component type magenta developer (1) for magnetic brush development.

Examples D-2 to D-8

Magenta toners (2) to (8) of Examples D-2 to D-8 were obtained in the same manner as in Example D-1 except that 10 parts by mass of each of PHA(A-3) to (A-5) and PHA(C-1) to (C-4) were used in place of PHA (A-1). The properties of the toners were measured in the same manner as in Example D-1, and the results are shown in Table 11. In addition, two-component type magenta developers (2) to (8) were obtained in the same manner as in Example D-1 using the toners, respectively.

Comparative Example D-1

A magenta toner D-1 of Comparative Example D-1 was obtained in the same manner as in Example D-1 except that 100 parts by mass of styrene-butylacrylate copolymer resin (glass transition temperature 70° C.) was used in place of PHA(A-1) The properties of the toner were measured in the same manner as in Example D-1, and the results were shown in Table 11. In addition, a two-component type magenta developer 9 was obtained in the same manner as in Example D-1 using the toner.

<Evaluation>

For the two-component type magenta developers (1) to (8) obtained in the above Examples D-1 to D-8 and the two-component type magenta developer 9 obtained in Comparative Example D-1, the charge levels of the toners after stirring for 10 and 300 seconds were measured under conditions of normal temperature and normal humidity (25° C., 60% RH) and high temperature and high humidity (30° C., 80% RH) using the previously described method for measuring charge levels. Then, numbers from measurement values of two-component blow-off charge levels were rounded off to the first decimal place to make evaluations according to the following criteria. The results are shown together in Table 11.

(A-5), and PHA(C-1) to (C-4) were used, and a carbon black (DBP oil absorption 110 mL/100 g) was used in place of the magenta pigment. The properties of the toners were measured in the same manner as in Example D-1, and the results are shown in Table 12. In addition, two-component type black developers (1) to (8) were obtained in the same manner as in Example D-1 using the toners.

Comparative Example D-2

A black toner 9 of Comparative Example D-2 was obtained in the same manner as in Example D-1 except that 100 parts by mass of styrene-butylacrylate copolymer resin (glass transition temperature 70° C.) was used in place of PHA(A-1) and a carbon black (DBP oil absorption 110 mL/100 g) was used in place of the magenta pigment. The properties of the toner were measured in the same manner as in Example D-1, and the results are shown in Table 12. In addition, a two-component type black developer 9 of Comparative Example D-2 was obtained in the same manner as in Example D-1 using the toner.

<Evaluation>

For the two-component type black developers (1) to (8) obtained in the above Examples D-9 to D-16 and the two-component type black developer 9 obtained in Comparative Example 2, the charge levels of the toners after stirring for 10 and 300 seconds were measured under conditions of normal temperature and normal humidity (25° C., 60% RH) and high temperature and high humidity (30° C., 80% RH) using the previously described method for measuring charge levels. Then, numbers from measurement values of two-component blow-off charge levels were rounded off to the first decimal place to make evaluations according to the following criteria. The results are shown together in Table 12.

TABLE 11

Electrification property of magenta toners (1) to (9)
(Magenta is called Red for the convenience)

| | | | | | Electrifiability | | | |
|---|---|---|---|---|---|---|---|---|
| | | | Particle size distribution Weight | Ratio of | Normal temperature and normal humidity (Q/M) | | High temperature and high humidity (Q/M) | |
| Examples | Number of PHA | Toner Number: Red | average particle size (μm) | fines (% by number) | Stirring for 10 seconds | Stirring for 300 seconds | Stirring for 10 seconds | Stirring for 300 seconds |
| D-1 | A-1 | 1 | 8.3 | 2.4 | AA | AA | AA | AA |
| D-2 | A-3 | 2 | 7.7 | 2.9 | A | AA | A | A |
| D-3 | A-4 | 3 | 8.0 | 3.2 | AA | AA | AA | AA |
| D-4 | A-5 | 4 | 8.2 | 3.5 | AA | AA | AA | AA |
| D-5 | C-1 | 5 | 8.8 | 4.5 | AA | AA | AA | AA |
| D-6 | C-2 | 6 | 9.0 | 3.9 | A | AA | A | A |
| D-7 | C-3 | 7 | 8.8 | 4.1 | AA | AA | AA | AA |
| D-8 | C-4 | 8 | 9.1 | 4.2 | AA | AA | AA | AA |
| Comparative Example D-1 | — | 9 | 7.0 | 4.9 | AA | AA | AA | AA |

<Electrifiability>
AA: Excellent (−20 μC/g or lower)
A: Good (−19.9 to −10.0 μC/g)
B: Usable (−9.9 to −5.0 μC/g)
C: Unusable (−4.9 μC/g or higher)

Examples D-9 to D-16

Black toners (1) to (8) of Examples D-9 to D-16 were obtained respectively in the same manner as in Example D-1 except that 100 parts by mass of PHA(A-1), PHA(A-3) to

TABLE 12

Electrification characteristic of black toners (1) to (9)

| Examples | Number of PHA | Toner Number: Black | Particle size distribution Weight average particle size (μm) | Ratio of fines (% by number) | Electrifiability Normal temperature and normal humidity (Q/M) Stirring for 10 seconds | Stirring for 300 seconds | High temperature and high humidity (Q/M) Stirring for 10 seconds | Stirring for 300 seconds |
|---|---|---|---|---|---|---|---|---|
| D-9 | A-1 | 1 | 8.1 | 2.2 | AA | AA | AA | AA |
| D-10 | A-3 | 2 | 7.9 | 2.7 | A | AA | A | A |
| D-11 | A-4 | 3 | 8.3 | 3.0 | AA | AA | AA | AA |
| D-12 | A-5 | 4 | 8.1 | 3.0 | AA | AA | AA | AA |
| D-13 | C-1 | 5 | 8.9 | 4.3 | AA | AA | AA | AA |
| D-14 | C-2 | 6 | 9.1 | 3.7 | A | AA | A | A |
| D-15 | C-3 | 7 | 8.5 | 4.0 | AA | AA | AA | AA |
| D-16 | C-4 | 8 | 9.0 | 4.1 | AA | AA | AA | AA |
| Comparative Example D-2 | — | 9 | 7.2 | 4.0 | AA | AA | AA | AA |

<Electrifiability>
AA: Excellent (−20 μC/g or lower)
A: Good (−19.9 to −10.0 μC/g)
B: Usable (−9.9 to −5.0 μC/g)
C: Unusable (−4.9 μC/g or higher)

Example D-17 and Comparative Example D-3

<Deinking Property Test>
Test paper was produced by forming test images with a black and white ratio of 6% on the surface of paper (75 g/m$^2$) by using the black toners 1 to 9 obtained in Examples D-9 to D-16 and Comparative Example D-2. Hand-made paper sheets for evaluation were produced with following conditions by using the above test paper.
Disaggregation: An aqueous dispersion of the following composition was stirred in a beaker at 50° C. for 20 minutes for disaggregation.
Test paper 5.0%
NaOH 0.7%
Sodium silicate 3.0%
H$_2$O$_2$ 1.0%
Deinking agent (from Lion Corporation, "Liptol S 2800") 0.2%
Dilution/dehydration/kneader treatment: Water was added to the above aqueous dispersion to dilute to 5%. The mixture was dehydrated centrifugally, and thus obtained pulp, sodium silicate, and the like were added to make the proportion of 20% of pulp, 3.0% of sodium silicate, and 0.5% of NaOH and disaggregated by a kneader.
Aging: The kneader-disaggregated product was aged at 50° C. for 2 hours.
Flotation: Water was added to the aged product to prepare a dispersion with pulp concentration of 1%, and fine bubbles were blown into the dispersion for 7 minutes. The toner in the solution was adsorbed to the bubbles and floated on the water surface to separate the toner and water.
Washing: 2.4 g of pulp subjected to deinking was washed with 1 L of water twice.
Preparation of hand-made sheet for test: A hand-made sheet (basis weight 100 g/m$^2$) was produced by a tappet sheet machine.

Evaluation of deinking property: The number of the toners existing in 9 cm$^2$ of the hand-made sheet was evaluated visually and microscopically by classifying the toners into two sizes of 100 μm or larger (visible) and 60 to 100 μm. The results of the above test are shown in Table 13. The values in the table indicate the number of the remaining toners.

TABLE 13

Results of deinking property test

| | 60 to 100 μm Number | 100 μm or larger Number | Total Number |
|---|---|---|---|
| Example D-9 | 8 | 9 | 17 |
| Example D-10 | 7 | 8 | 15 |
| Example D-11 | 10 | 11 | 21 |
| Example D-12 | 9 | 11 | 21 |
| Example D-13 | 13 | 15 | 28 |
| Example D-14 | 11 | 14 | 25 |
| Example D-15 | 15 | 16 | 31 |
| Example D-16 | 11 | 13 | 24 |
| Comparative Example D-2 | 43 | 38 | 81 |

Example D-18

<Biodegradability Test>
Red toners 1 to 8, black toners 1 to 8, comparative red toner 9, and comparative black toner 9 were melt-molded to films with thickness of about 50 μm and buried in the soil for 6 months. As the result, films of red toners 1 to 8 and black toners 1 to 8 lost the shape completely. On the other hand, the shape of comparative red toner 9 and comparative black toner 9 remain intact.

Example D-19 to Example D-34 and Comparative Example D-3 to Comparative Example D-4

Figure 5:
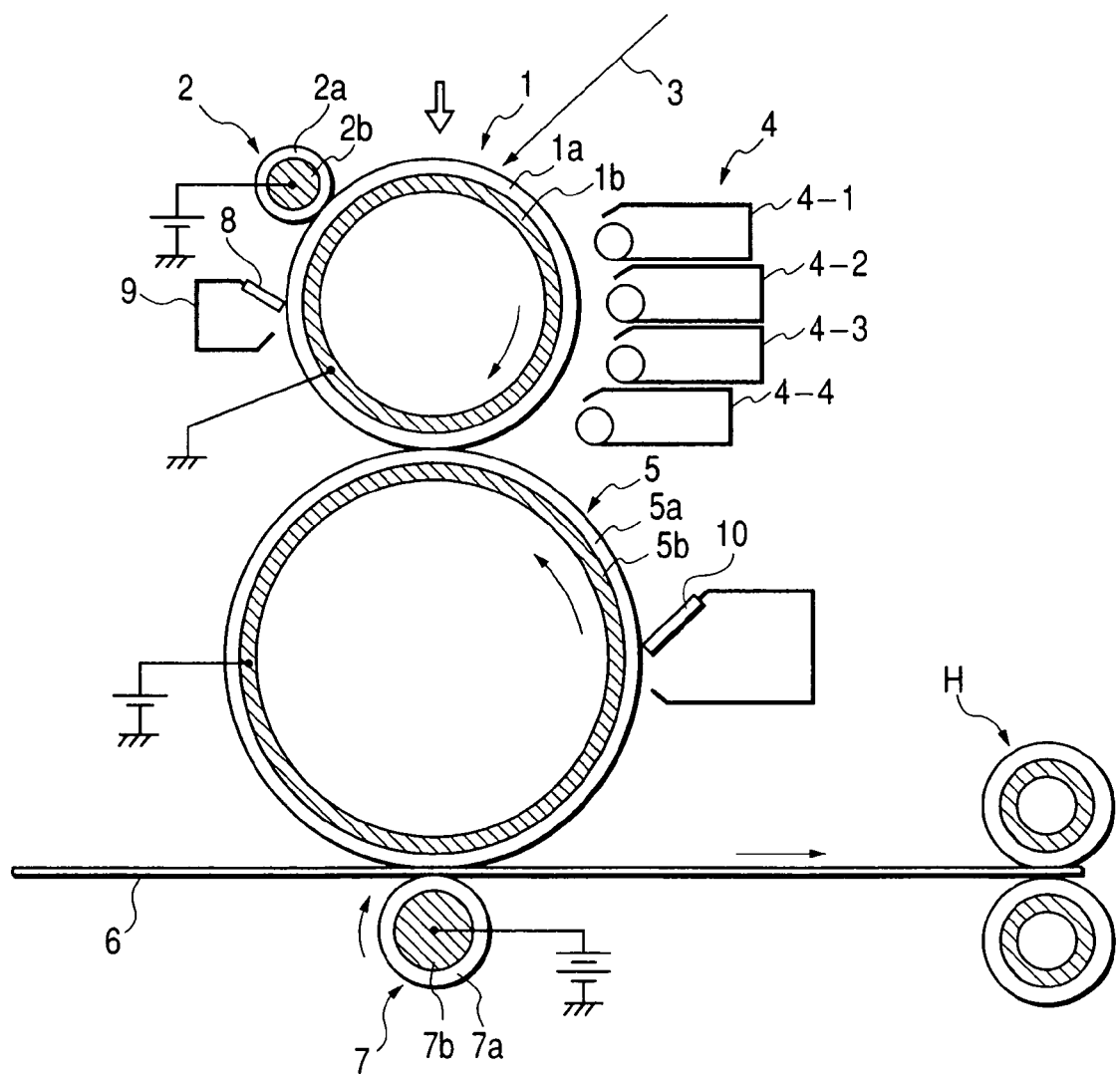
FIG. 5 is a schematic illustration of the image forming apparatus that is used in Examples D-19 to D-34, Examples E-7 to E-12, Examples F-7 to F-12, Comparative Examples D-3 to D-4 and Comparative Examples E-7 to E-12.

First, an image forming apparatus used in the image formation methods of Example D-19 to Example D-34 and Comparative Example D-3 to Comparative Example D-4 will be described. FIG. 5 is a schematic explanatory view of the cross section of an image forming apparatus for carrying out the image formation methods of Examples and Comparative Examples of the present invention. A photosensitive drum 1 shown in FIG. 5 has a photosensitive layer 1a having an organic photosemiconductor on a substrate 1b, and configured to rotate in the direction indicated by the arrow, and its surface is electrically charged at a potential of about −600 V by a charge roller 2 being a charging member situated opposite to the photosensitive drum 1 and contacting and rotating with the drum. As shown in FIG. 5, the charge roller 2 has a metal core 2b covered with a conductive elastic layer 2a.

Figure 6:
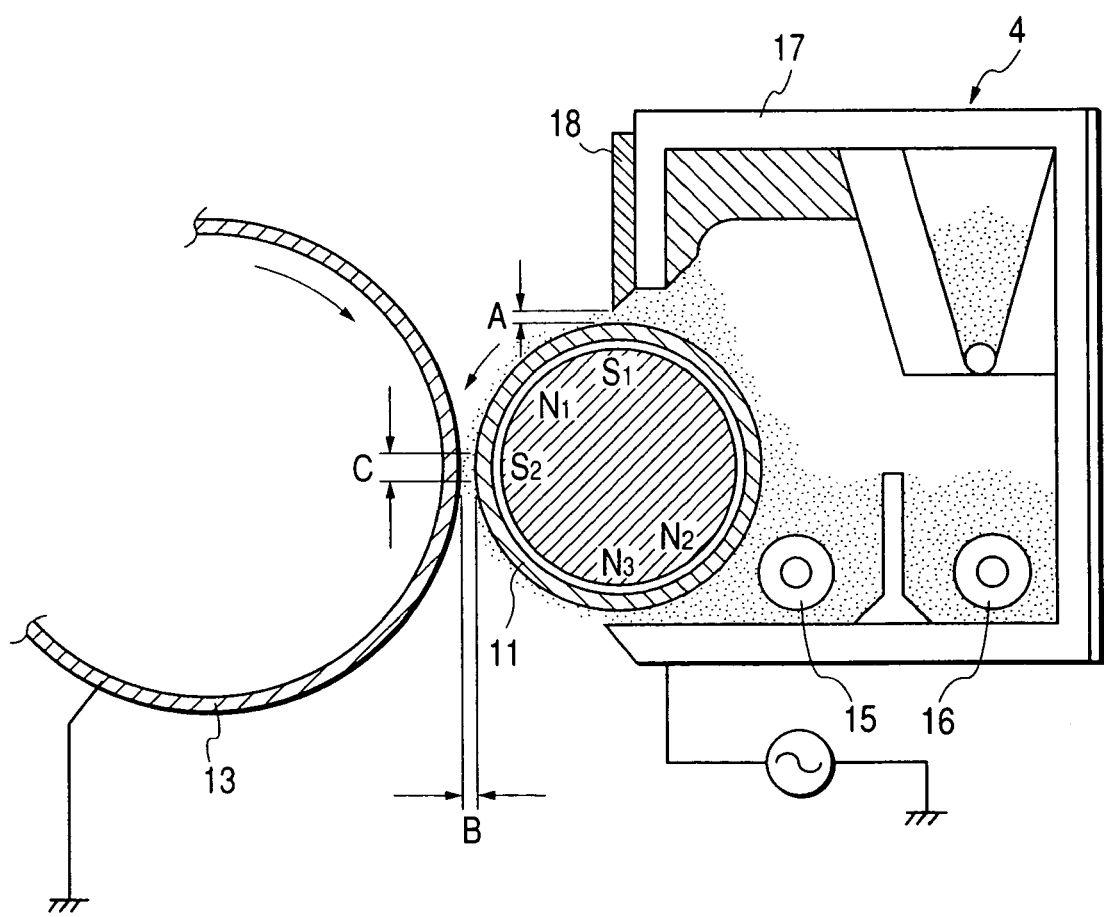
FIG. 6 is a cross-sectional view showing the main part of the developing equipment for two component developing agent that is used in Examples D-19 to D-34, Examples E-7 to E-12, Examples F-7 to F-12, Comparative Examples D-3 to D-4 and Comparative Examples E-7 to E-12.

Next, the photosensitive drum 1 with its surface electrically charged is exposed to light 3 and at that time, on/off operations are performed on the photoconductor by a polygon mirror according to digital image information, whereby an electrostatic latent image with the potential of the exposed area being −100 V and the potential of the dark area being −600 V is formed. Subsequently, this electrostatic latent image on the photosensitive drum 1 is reverse-developed and thereby actualized using a plurality of development apparatuses 4-1, 4-2, 4-3, and 4-4, and thus a toner image is formed on the photosensitive drum 1. At that time, the two-component type developers obtained in Examples D-1 to D-16 and Comparative Examples D-1 to D-2 were respectively used as developers to form a toner image with a magenta toner or a black toner. FIG. 6 is an enlarged sectional view of principal parts of development apparatuses 4 for two-component type developers used at that time. Then, the toner image on the photosensitive drum 1 is transferred to an intermediate transfer member 5 contacting and rotating with the photosensitive drum 1. As the result, a four-color color combination developed image is formed on the intermediate transfer member 5. A non-transferred toner remaining on the photosensitive drum 1 without being transferred is collected in a residual toner container 9 by a cleaning member 8.

The intermediate transfer member 5 comprises a metal core 5b as a support and an elastic layer 5a provided thereon as shown in FIG. 5. In this Example, the intermediate transfer member 5 having the pipe-shaped metal core 5b coated with the elastic layer 5b with a carbon black as a conductivity producer sufficiently dispersed in nitrile-butadiene rubber (NBR) was used. The hardness of the elastic layer 5b measured in accordance with "JIS K-6301" was 30 degrees, and the volume resistivity was $10^9$ Ω·cm. The level of transfer current required for transferring the image from the photosensitive drum 1 to the intermediate transfer member 5 is about 5 μA, and this level of current was obtained by adding a voltage of +500 V from the power supply to the metal core 5b.

The four-color toner color combination developed image formed on the intermediate transfer member 5 is transferred to a transferring material such as paper by a transfer roller 7, and then fixed by a heat-fixation apparatus H. The transfer roller 7 is provided the metal core 7b with the outside diameter of 10 mm on which an elastic layer 7a is formed by coating of a foam of ethylene-propylene-diene based tridimensional copolymer (EPDM) dispersing the carbon sufficiently therein as a conductivity producing material. The layer had a volume specific resistance of $10^6$ Ω·cm and a hardness of 35 degrees as measured in accordance with "JIS K-6301". In addition, a voltage was applied to this transfer roller 7 to pass a transfer current of 15 μA therethrough.

Figure 9:
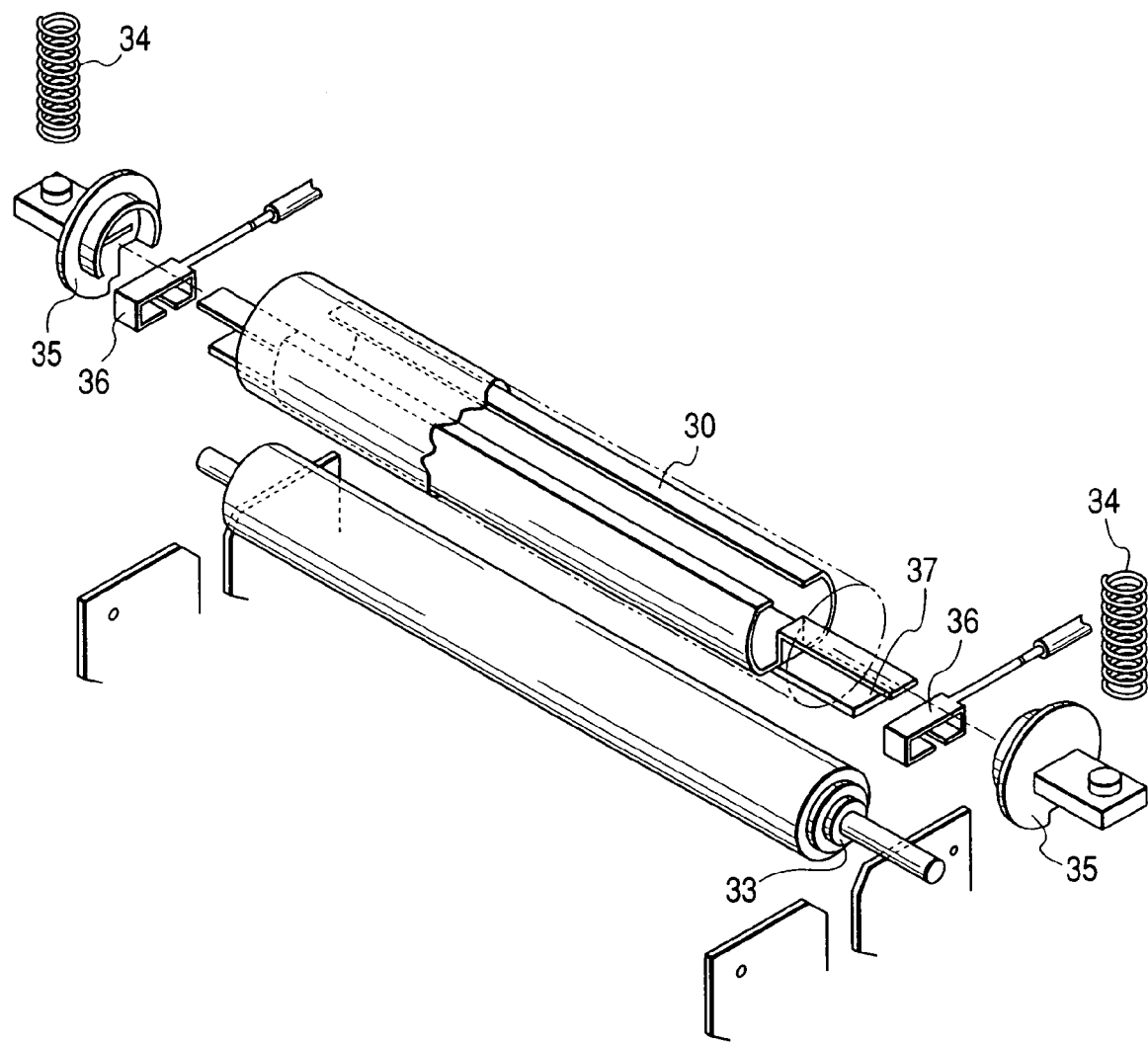
FIG. 9 is an exploded perspective view of the main part of the fixing equipment used in the Examples of this invention.
Figure 10:
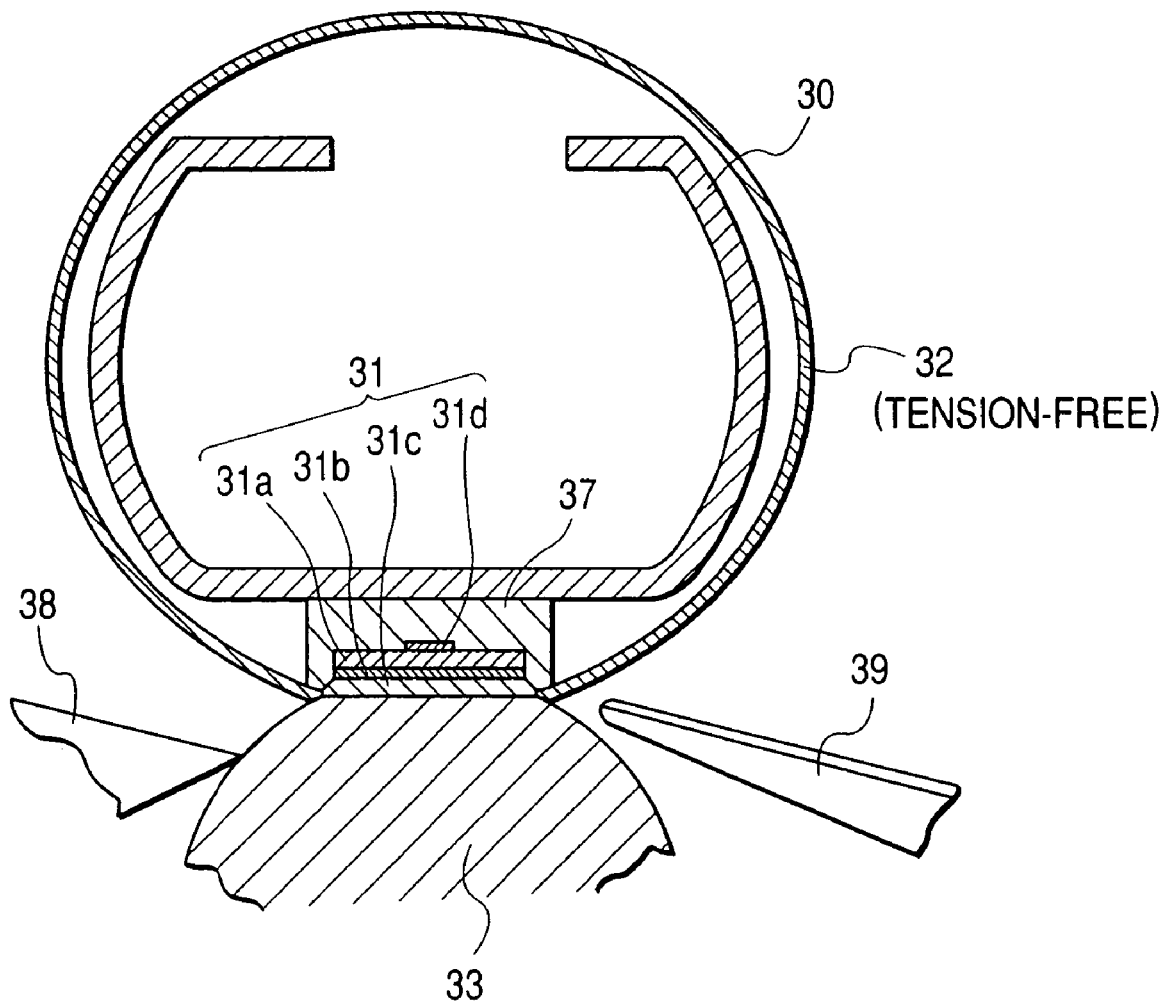
FIG. 10 is an enlarged sectional view of the main part of the fixing equipment that is used in the Examples of this invention.

In the apparatus shown in FIG. 5, a fixation apparatus of heated roll type having no oil coating mechanism shown in FIGS. 9 and 10 was used in the heat-fixation apparatus H. The both upper and lower rollers of the fixation apparatus used here had surface layers made of fluorine based resin. In addition, the diameter of the roller was 60 mm. The fixation temperature for fixation was 160° C., and the nipping width was set at 7 mm. Furthermore, the residual toner on the photosensitive drum 1 was collected by cleaning and transported to a developing device by a reuse mechanism for reuse.

<Evaluation>

Two-component type developers produced using the toners of Examples D-1 to D-16 and two-component type developers produced using toners of Comparative Examples D-1 to D-2 were used, respectively, to perform printout testing at a printout rate of 8 sheets (A4 size) per minute, supplying the developer, in a monochromatic intermittent mode (namely a mode in which the developing device is stopped for 10 seconds for each printout to accelerate the deterioration of the toner in a preliminary operation during restart of the device) at a normal temperature and normal humidity (25° C., 60% RH) and a high temperature and high humidity (30° C., 80% RH) under the conditions described above, and resulting printout images were evaluated for the following items. The evaluation results are shown together in Table 14.

<Evaluation of Printout Images>

1. Image Density

Images were printed out on a predetermined number of normal copying papers (75 g/m$^2$), and the image density was evaluated according to the level at which the density of the image from the final printout was retained with respect to the density of the initial image. Here, for the measurement of image density, a Macbeth reflective densitometer (from Macbeth Co., Ltd.) was used to measure a density relative to that of the printout image of a white ground of which original density was 0.00.

AA: Excellent (image density from the final printout is 1.40 or greater)

A: Good (image density from the final printout is 1.35 or greater and lower than 1.40)

B: Usable (image density from the final printout is 1.00 or greater and lower than 1.35)

C: Unusable (image density from the final printout is lower than 1.00)

2. Image Fog

Images were printed out on a predetermined number of normal copying papers (75 g/m$^2$), and the image fog was evaluated with a solid white image from the final printout. Specifically, the evaluation was made as follows: the worst value of the reflective density of the white ground after printing and the average reflective density of the paper before printing, as measured using a reflective densitometer (Reflectometer ODEL TC-6DS from Tokyo Denshoku Co., Ltd.), were defined as Ds and Dr, respectively, and (Ds-Dr) was calculated from these values as a fog level to make an evaluation according to the following criteria.

AA: Excellent (fog level is 0% or higher and lower than 1.5%)

A: Good (fog level is 1.5% or higher and lower than 3.0%)

B: Usable (fog level is 3.0% or higher and lower than 5.0%)

C: Unusable (fog level is higher than 5.0%)

3. Transferability

Solid black images were printed out on a predetermined number of normal copying papers (75 g/m$^2$), and the image dislocation level of the image from the final printout was visually observed to make an evaluation according to the following criteria.

AA: Excellent (almost not observed)

A: Good (slightly observed)

B: Usable

C: Unusable.

In addition, in Example D-19 to Example D-34 and Comparative Example D-3 to Comparative Example D-4, occurrences of scars and sticking residual toners on the surfaces of the photosensitive drum and the intermediate transfer member, and their influence on printout images (matching with the image forming apparatus) were visually evaluated after 5000 images were outputted, and as a result, scars and sticking residual toners on the surfaces of the photosensitive drum and the intermediate transfer member were not observed at all, and thus matching with the image forming apparatus was excellent.

TABLE 14

Evaluation result of printout image

| Examples/ Comparative Examples | Two-component type developer | Normal temperature and normal humidity | | | High temperature and high humidity | | |
|---|---|---|---|---|---|---|---|
| | | Image density | Image fog | Transferability | Image density | Image fog | Transferability |
| D-19 | Red 1 | AA | AA | AA | AA | AA | AA |
| D-20 | Red 2 | AA | A | AA | AA | A | A |
| D-21 | Red 3 | AA | AA | AA | AA | AA | AA |
| D-22 | Red 4 | AA | AA | AA | AA | AA | AA |
| D-23 | Red 5 | AA | AA | AA | AA | AA | AA |
| D-24 | Red 6 | AA | A | AA | AA | A | A |
| D-25 | Red 7 | AA | AA | AA | AA | AA | AA |
| D-26 | Red 8 | AA | AA | AA | AA | AA | AA |
| D-27 | Black 1 | AA | AA | AA | AA | AA | AA |
| D-28 | Black 2 | AA | A | AA | AA | A | A |
| D-29 | Black 3 | AA | AA | AA | AA | AA | AA |
| D-30 | Black 4 | AA | AA | AA | AA | AA | AA |
| D-31 | Black 5 | AA | AA | AA | AA | AA | AA |
| D-32 | Black 6 | AA | A | AA | AA | A | A |
| D-33 | Black 7 | AA | AA | AA | AA | AA | AA |
| D-34 | Black 8 | AA | AA | AA | AA | AA | AA |
| Comparative Example D-3 | Red 9 | AA | AA | AA | AA | AA | AA |
| Comparative Example D-4 | Black 9 | AA | AA | AA | AA | AA | AA |

Example D-35 to Example D-42, Comparative Example D-5 to Comparative Example D-6

Figure 7:
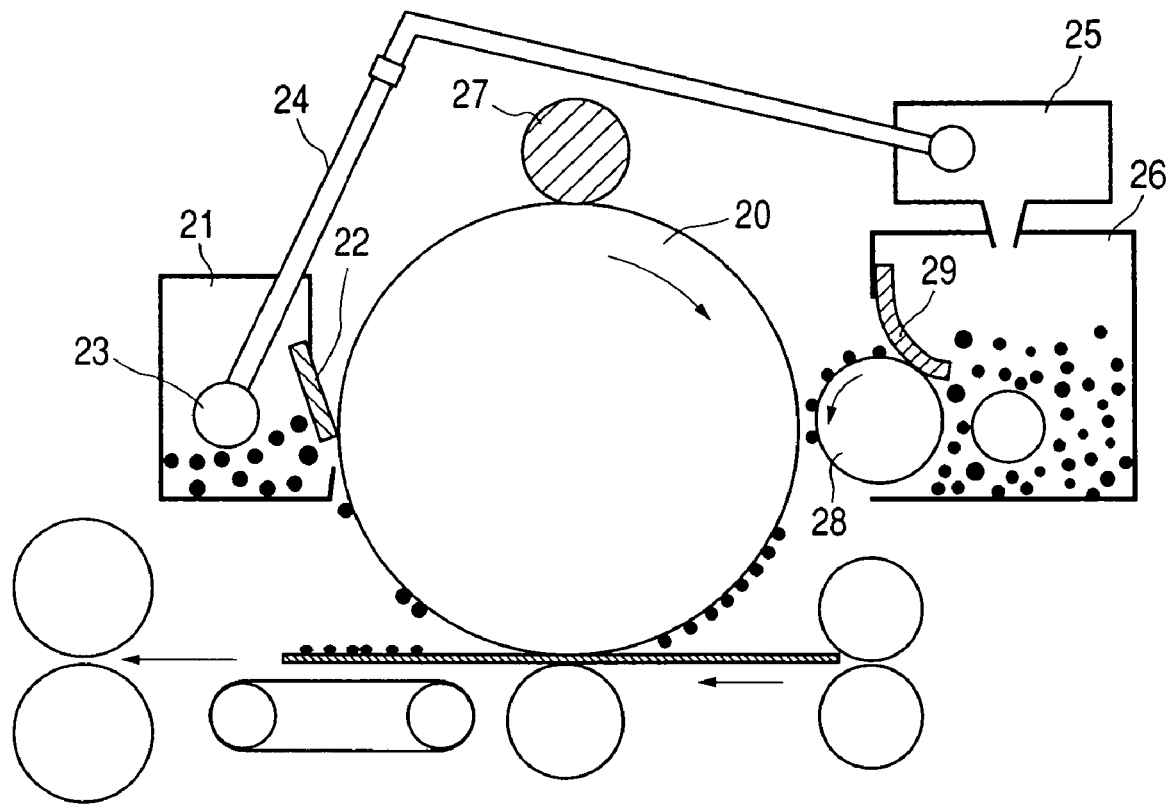
FIG. 7 is a schematic illustration of the image forming apparatus including a reuse mechanism for toner that is used in Examples D-35 to D-42, Examples E-13 to E-16, Examples F-13 to F-16, Comparative Examples D-5 to D-6 and Comparative Examples F-13 to F-15.

For carrying out the image formation methods of Example D-35 to Example D-42 and Comparative Example D-5 to Comparative Example D-6, the toners obtained in Examples D-9 to D-16 and Comparative Examples D-1 to D-2 were used respectively as developers. In addition, for means for forming an image, an image forming apparatus with a commercially available laser beam printer LBP-EX (from Canon Inc.) modified so that it was provided with a reuse mechanism and reset as shown in FIG. 7 was used. That is, the image forming apparatus shown in FIG. 7 is provided with a system in which a non-transferred toner remaining on the photosensitive drum 20 after the transfer process is scraped off by an elastic blade 22 of a cleaner 21 abutting against the photosensitive drum 20, then sent into the cleaner 21 by a cleaning roller, passed through a cleaner reuse 23, and returned to the development device 26 via a hopper 25 by a supply pipe 24 with a carrier screw mounted therein, and the toner collected in this way is reused.

In the image forming apparatus shown in FIG. 7, the surface of the photosensitive drum 20 is electrically charged by a primary charge roller 27. A rubber roller (diameter 12 mm, abutment pressure 50 gf/cm) coated with a nylon resin and having conductive carbon dispersed therein was used for the primary charge roller 27, and an electrostatic latent image with a dark area potential VD of −700 V and a light area potential VL of −200 V was formed on the electrostatic latent image-holding member (photosensitive drum 20) by laser exposure (600 dpi, not shown). As a toner carrier, a development sleeve 28 having a surface roughness degree Ra of 1.1 with the surface coated with a resin having a carbon black dispersed therein was used.

Figure 8:
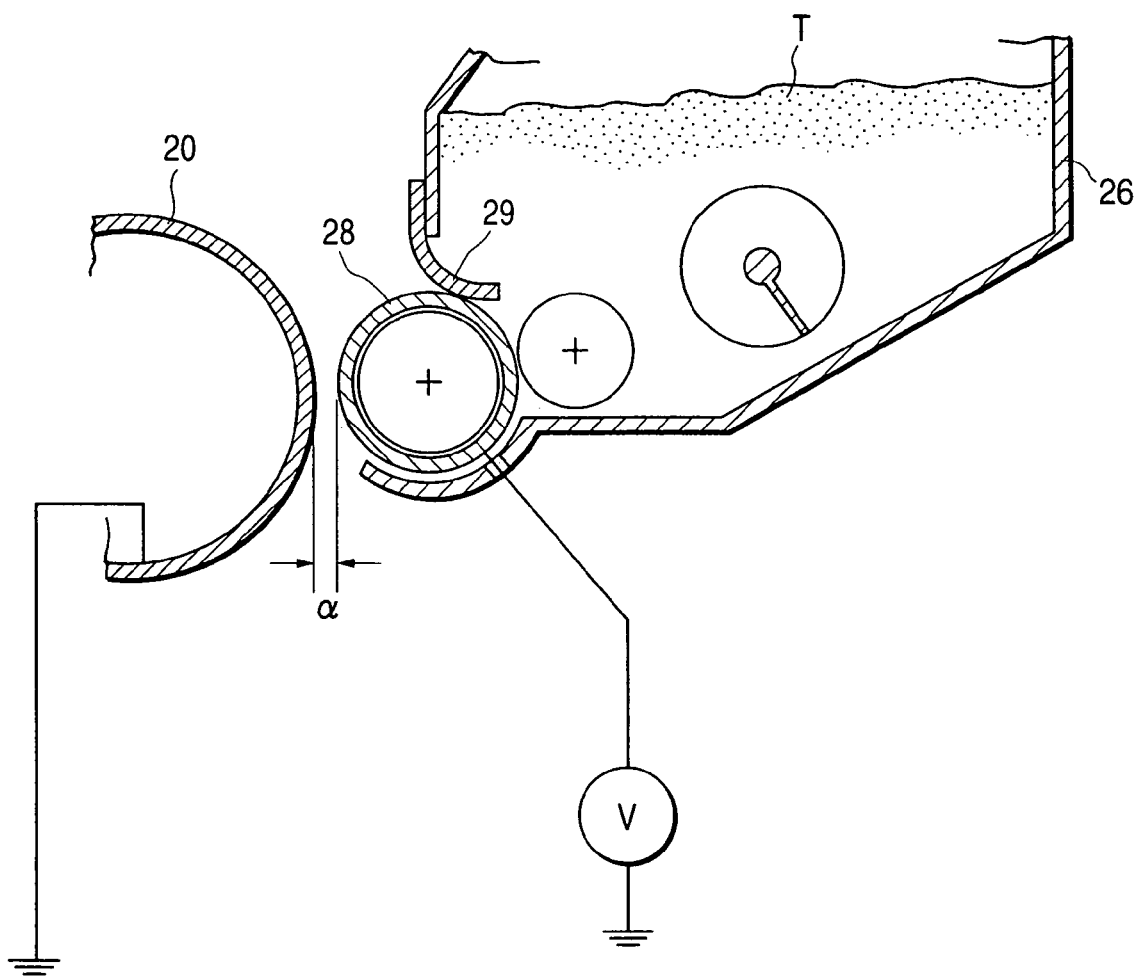
FIG. 8 is a cross-sectional view showing the main part of the developing equipment for one component developing agent that is used in Examples D-35 to D-42, Examples E-13 to E-16, Examples F-13 to F-16, Comparative Examples D-5 to D-6 and Comparative Examples F-13 to F-15.

An enlarged sectional view of the principal part of the development apparatus for one-component type developers used in Example D-35 to Example D-42 and Comparative Example D-5 to Comparative Example D-6 is shown in FIG. 8. For conditions for developing electrostatic latent images, the speed of the development sleeve 28 was set at a speed 1.1 times as high as the movement speed of the surface of the photosensitive drum 20 opposite thereto, and the space a between the photosensitive drum 20 and the development sleeve 28 (between S and D) was 270 μm. For the member for controlling the thickness of the toner layer, an abutting urethane rubber blade 29 was used. In addition, the set temperature of the heat-fixation apparatus for fixing a toner image was 160° C. Furthermore, for the fixation apparatus, a fixation apparatus shown in FIG. 9 and FIG. 10 was used.

As described above, under the condition of normal temperature and normal humidity (25° C., 60% RH), images were printed out on up to 30,000 sheets at a printout rate of 8 sheets (A4 size) per minute, supplying the toner, in a continuous mode (namely, a mode in which the development device is not stopped, thereby accelerating consumption of the toner), and the densities of resulting printout images were measured to evaluate the durability according to the following criteria. In addition, the image from the 10,000th printout was observed to make an evaluation about image fog according to the following criteria. At the same time, conditions of the components of the image forming apparatus after the durability testing were observed to evaluate matching between the members and the above toners. The results thereof are shown together in Table 15.

<Change in Image Density During Endurance>

The image density was evaluated according to the level at which the density of the image from the final printout was retained with respect to the density of the initial image. The density of the image was evaluated in the same manner as in Example D19 to 34.

<Image Fog>

The image fog was evaluated in the same manner as in Example D19 to 34.

<Evaluation of Matching with Image Forming Apparatus>

1. Matching With Development Sleeve

After the printout testing was completed, the situation of residual toners sticking to the surface of the development sleeve and their influence on the printout image were visually evaluated.

AA: Excellent (not observed)
A: Good (almost not observed)
B: Usable (sticking residual toners are observed but the influence on the image is not significant)
C: Unusable (sticking of residual toners is significant, causing unevenness in the image)

2. Matching With Photosensitive Drum

Occurrences of scars and sticking residual toners on the surface of the photosensitive drum and their influence on the printout image were visually evaluated.

AA: Excellent (not observed)
A: Good (scars are slightly observed but no influence on the image)
B: Usable (sticking residual toners and scars are observed but the influence on the image is not significant)
C: Unusable (sticking of residual toners is significant, causing longitudinal striped defects in the image)

3. Matching With Fixation Apparatus

The surface conditions of the fixation film was observed, and the results of surface characteristics and occurrences of sticking residual toners were collectively averaged to evaluate the durability of the film.

(1) Surface Characteristics

Occurrences of scars and flaking on the surface of the fixation film were visually observed and evaluated after the printout testing was completed.
AA: Excellent (not observed)
A: Good (almost not observed)
B: Usable
C: Unusable (2) Situation of Sticking Residual Toners The situation of residual toners sticking to the surface of the fixation film was visually observed and evaluated after the printout testing was completed.
AA: Excellent (not observed)
A: Good (almost not observed)
B: Usable
C: Unusable

TABLE 15

Evaluation results of printout image and matching with image forming apparatus

| | | Evaluation of printout image | | | | Evaluation of matching with each apparatus | | | |
| | | Change in image density during endurance | | | 10 thousands | | | Fixation apparatus | |
| Examples | Toner | Initial | Thousand | 10 thousands | 30 thousands | fogged images | Development sleeve | Photo sensitive drum | Surface characteristic | Toner fixation |
| --- | --- | --- | --- | --- | --- | --- | --- | --- | --- | --- |
| D-35 | Black 1 | AA | AA | AA | AA | AA | AA | AA | AA | AA |
| D-36 | Black 2 | AA | AA | A | A | AA | AA | AA | AA | A |
| D-37 | Black 3 | AA | AA | AA | AA | AA | AA | AA | AA | AA |
| D-38 | Black 4 | AA | AA | AA | AA | AA | AA | AA | AA | AA |
| D-39 | Black 5 | AA | AA | AA | AA | AA | AA | AA | AA | AA |
| D-40 | Black 6 | AA | AA | A | A | A | AA | A | AA | A |
| D-41 | Black 7 | AA | AA | AA | AA | AA | AA | AA | AA | AA |
| D-42 | Black 8 | AA | AA | AA | AA | AA | AA | AA | AA | AA |
| Comparative Example D-5 | Red 9 | AA | AA | AA | AA | AA | AA | AA | AA | AA |
| Comparative Example D-6 | Black 9 | AA | AA | AA | AA | AA | AA | AA | AA | AA |

Example D-43

Printout testing was performed, supplying the black toner 1 of Example D-9, in a continuous mode (namely, a mode in which the development device is not stopped, thereby accelerating consumption of the toner) in the same manner as in Example D-42 except that the toner reuse mechanism of the image forming apparatus of FIG. 7 was removed, and the printout rate was set at the level of 16 sheets (A4 size) per minute. The resultant printout images and the matching with the image evaluating apparatus used were evaluated for the same items as in Example D-35 to Example D-42 and Comparative Example D-5 to Comparative Example D-6. As the result, satisfactory results were obtained for all the items.

[Use as Charge Controlling Agent in Toner]

PHA of the present invention may be used as a binder resin and is also applicable as a charge controlling agent. Therefore, PHA (PHA(A-1) to (A-2)) produced as in Examples A-1 and A-2 in the manner selected from the methods of the present invention were used as charge controlling agents to produce various toners and evaluated (Examples E-1 to E-16, F-1 to F-16, Comparative Examples E-1 to E-16).

Example E-1

First, an aqueous Na$_3$PO$_4$ solution was added in a 2 liter four-necked flask equipped with a high-speed stirring apparatus TK-Homomixer, and heated to 60° C. with stirring at 10,000 rpm. An aqueous CaCl$_2$ solution was slowly added therein to prepare a water based dispersing medium containing a very small low-water solubility dispersant Ca$_3$(PO$_4$)$_2$.

On the other hand, the following composition was dispersed for 3 hours using a ball mill, followed by adding therein 10 parts by mass of a release agent (ester wax) and 10 parts by mass of 2,2'-azobis(2,4-dimethylvaleronitrile) as a polymerization initiator to prepare a polymerizable monomer composition.

| | |
|---|---|
| Styrene monomer | 82 parts by mass |
| Ethylhexyl acrylate monomer | 18 parts by mass |
| Divinylbenzene monomer | 0.1 parts by mass |
| Cyan coloring agent (C.I. Pigment Blue 15) | 6 parts by mass |
| Oxidized polyethylene resin (molecular weight 3200, acid number 8) | 5 parts by mass |
| PHA(A-1) | 2 parts by mass |

Then, the polymerizable monomer composition obtained as described above was charged in the water based dispersant prepared previously to form particles with the number of rotations being kept at 10,000 rpm. Thereafter, the composition was made to undergo a reaction at 65° C. for 3 hours while being stirred with a paddle stirring blade, and thereafter polymerized at 80° C. for 6 hours to complete the polymerization reaction. After the reaction was completed, the suspension was cooled, and an acid was added therein to dissolve the low-water solubility dispersant Ca$_3$(PO$_4$)$_2$, followed by filteration, rinsing and drying to obtain blue polymerized particles (1). The particle size of the obtained blue polymerized particles (1) measured using Coulter Counter Multisizer (from Coulter Co.) was 6.8 µm (weight average particle size), and the ratio of fines was 4.9% by number.

As a fluidity improver, 1.3 parts by mass of hydrophobic silica fine powder (BET: 270 m$^2$/g) treated with hexamethyl disilazane were externally added to 100 parts by mass of blue polymerized particles(1) prepared as described above through dry-mixing by a Henshel mixer, whereby a blue toner (1) of this Example was obtained. In addition, 7 parts by mass of blue toner (1) were mixed with 93 parts by mass resin-coated magnetic ferrite carrier (average particle size: 45 µm) to prepare a two-component type blue developer (1) for magnetic brush development.

Example F-1

Blue toner S1 of Example F-1 was obtained in the same manner as in Example E-1 except that 2 parts by mass of PHA(A-2) are used in place of an exemplary compound (1). In addition, two-component type blue developer S1 was obtained in the same manner as in Example B-1 using the blue toner.

Comparative Example E-1

A blue toner (2) of Comparative Example E-1 was obtained in the same manner as in Example E-1 except that no exemplary compound was used. The properties of this toner were measured in the same manner as in Example E-1, and the results thereof are shown in Table 16. In addition, a two-component type blue developer (2) of Comparative Example E-1 was obtained in the same manner as in Example E-1 using this toner.

<Evaluation>

For the two-component type blue developers (1), (S1) obtained in the above Examples E-1, F-1 and the two-component type blue developer (2) obtained in Comparative Example 1, the charge levels of the toners after stirring for 10 and 300 seconds were measured under conditions of normal temperature and normal humidity (25° C., 60% RH) and high temperature and high humidity (30° C., 80% RH) using the previously described method for measuring charge levels. Then, numbers from measurement values of two-component blow-off charge levels were rounded off to the first decimal place to make evaluations according to the following criteria. The results are shown together in Table 16.

Electrifiability
AA: Excellent (−20 µC/g or lower)
A: Good (−19.9 to −10.0 µC/g)
B: Usable (−9.9 to −5.0 µC/g)
C: Unusable (−4.9 µC/g or higher)

Examples E-2, F-2

Yellow toners (1) and (S1) of Examples E-2 and F-2 were obtained in the same manner as in Example E-1 except that 2.0 parts by mass of PHA(A-1) and (A-2) were used respectively, and a yellow coloring agent (Hansa yellow G) was used in place of the cyan coloring agent. The properties of these toners were measured in the same manner as in Example E-1, and the results thereof are shown in Table 16. In addition, two-component type yellow developers (1), (S1) were obtained in the same manner as in Example E-1 using these toners.

Comparative Example E-2

A yellow toner (2) of Comparative Example E-2 was obtained in the same manner as in Example E-1 except that PHA(A-1) or (A-2) was not used, and that the yellow coloring agent (Hansa yellow G) was used in place of the cyan coloring agent. The properties of this toner were measured in the same manner as in Example E-1, and the results thereof are shown in Table 16. In addition, a two-component type yellow developer (2) of Comparative Example E-2 was obtained in the same manner as in Example E-1 using this toner.

<Evaluation>

For the two-component type yellow developers (1), (S1) obtained in the Examples E-2, F-2 and the two-component type yellow developer (2) obtained in the Comparative Example E-2, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, numbers from measurement values of two-component blow-off charge levels were rounded off to the first decimal place to make evaluations according to the same criteria as in Example E-1. The results are shown together in Table 16.

Examples E-3, F-3

Black toners (1) and (S1) of Examples E-3 and F-3 were obtained in the same manner as in Example E-1 except that 2.0 parts by mass of PHA (A-1) and (A-2) were used respectively, and a carbon black (DBP oil absorption 110 mL/100 g) was used in place of the cyan coloring agent. The properties of these toners were measured in the same manner as in Example E-1, and the results thereof are shown in Table 16. In addition, two-component type black developers (1) and (S1) were obtained in the same manner as in Example E-1 using these toners.

Comparative Example E-3

A black toner (2) of Comparative Example B-3 was obtained in the same manner as in Example E-1 except that PHA(A-1) or (A-2) was not used, and that the carbon black (DBP oil absorption 110 mL/100 g) was used in place of the cyan coloring agent. The properties of this toner were measured in the same manner as in Example E-1, and the results thereof are shown in Table 16. In addition, a two-component type black developer (2) of Comparative Example B-3 was obtained in the same manner as in Example E-1 using this toner.

<Evaluation>

For the two-component type black developers (1) and (S1) obtained in the above Examples E-3 and F-3 and the two-component type black developer (2) obtained in the Comparative Example E-3, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, numbers from measurement values of two-component blow-off charge levels, were rounded off to the first decimal place to make evaluations according to the same criteria as in Example E-1. The results are shown together in Table 16.

Example E-4

| | |
|---|---|
| Styrene-butylacrylate copolymer resin (glass transition temperature 70° C.) | 100 parts by mass |
| Magenta pigment (C.I. Pigment Red 114) | 5 parts by mass |
| PHA(A-1) | 2 parts by mass. |

The above described compositions were mixed, and were melt-kneaded by a twin screw extruder (L/D=30). The resulting mixture was cooled, was thereafter roughly ground by a hammer mill and finely ground by a jet mill, and was thereafter classified to obtain magenta colored particles (1) by a grinding method. For the particle size of the magenta colored particles (1), the weight average particle size was 7.3 µm and the ratio of fines was 5.5% by number.

As a fluidity improver, 1.5 parts by mass of hydrophobic silica fine powder (BET: 250 m²/g) treated with hexamethyl disilazane were dry-mixed with 100 parts by mass of the magenta colored particles (1) by a Henshel mixer, whereby a magenta toner (1) of this Example was obtained. In addition, 7 parts by mass of the resulting magenta toner (1) were mixed with 93 parts by mass resin-coated magnetic ferrite carrier (average particle size: 45 µm) to prepare a two-component type magenta developer (1) for magnetic brush development.

Example F-4

Magenta toner (S1) of Example F-4 was obtained in the same manner as in Example E-4 except that 2 parts by mass of PHA (A-2) was used in place of PHA (A-1). The properties of this toner was measured in the same manner as in Example E-3, and the results thereof are shown in Table 16. In addition, two-component type magenta developer (S1) was obtained in the same manner as in Example E-4 using this toner.

Comparative Example E-4

A magenta toner (2) of Comparative Example E-4 was obtained in the same manner as in Example E-4 except that PHA(A-1) or (A-2) was not used. The properties of this toner were measured in the same manner as in Example E-3, and the results thereof are shown in Table 16. In addition, a two-component type magenta developer (2) of Comparative Example E-4 was obtained in the same manner as in Example E-4 using this toner.

<Evaluation>

For the two-component type magenta developers (1) and (S1) obtained in the Examples E-4 and F-4 and the two-component type magenta developer (2) obtained in the Comparative Example E-4, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, numbers from measurement values of two-component blow-off charge levels were rounded off to the first decimal place to make evaluations according to the same criteria as in Example E-1. The results are shown together in Table 16.

Examples E-5, F-5

Black toners (3) and (S3) of Examples E-5 and F-5 were obtained in the same manner as in Example E-4 except that 2.0 parts by mass of PHA(A-1) and (A-2) were used respectively, and a carbon black (DBP oil absorption 110 mL/100 g) was used in place of the magenta pigment. The properties of these toners were measured in the same manner as in Example B-1, and the results thereof are shown in Table 16. In addition, two-component type black developers (3) and (S3) were obtained in the same manner as in Example E-4 using these toners.

Comparative Example E-5

A black toner (4) of Comparative Example E-5 was obtained in the same manner as in Example E-4 except that PHA(A-1) or (A-2) was not used, and that the carbon black (DBP oil absorption 110 mL/100 g) was used in place of the magenta pigment. The properties of this toner were measured in the same manner as in Example E-1, and the results thereof are shown in Table 16. In addition, a two-component type black developer (4) of Comparative Example E-5 was obtained in the same manner as in Example E-4 using this toner.

<Evaluation>

Por the two-component type black developers (3) and (S3) obtained in the Examples E-5 and F-5 and the two-component type black developer (4) obtained in the Comparative Example E-5, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, numbers from measurement values of two-component blow-off charge levels were rounded off to the first decimal place to make evaluations according to the same criteria as in Example E-1. The results are shown together in Table 16.

Example E-6

| Polyester resin | 100 parts by mass |
|---|---|
| Carbon black (DBP absorption 110 mL/100 g) | 5 parts by mass |
| PHA(A-1) | 2 parts by mass. |

The polyester resin was synthesized as follows: 751 parts of bisphenol A propylene oxide 2 mol adduct, 104 parts of terephtalic acid and 167 parts of trimellitic anhydride were poly-condensed with two parts of dibutyltin oxide as a catalyst to obtain a polyester resin having a softening point of 125° C.

The above described compositions were mixed, and were melt-kneaded by a twen screw extruder (L/D=30). The resulting mixture was cooled, was thereafter roughly ground by a hammer mill and finely ground by a jet mill, and was thereafter classified to obtain black colored particles (5) by a grinding method. For the particle size of the black colored particles (5), the weight average particle size was 7.5 μm and the ratio of fines was 4.7% by number.

As a fluidity improver, 1.5 parts by mass of hydrophobic silica fine powder (BET: 250 m$^2$/g) treated with hexamethyl disilazane were dry-mixed with 100 parts by mass of the black colored particles (5) by a Henshel mixer to obtain a black toner (5) of this Example. Further, seven parts of the resultant black toner (5) were mixed with 93 parts by mass resin-coated magnetic ferrite carrier (average particle size: 45 μm) to prepare a two-component type black developer (5) for magnetic brush development.

Example F-6

A black toner (S5) of Example F-6 was obtained in the same manner as in Example E-6 except that 2 parts by mass of PHA(A-2) was used in place of PHA (A-1). The properties of the toner was measured in the same manner as in Example E-1, and the results thereof are shown in Table 16. In addition, a two-component type black developer (S5) was obtained in the same manner as in Example E-6 using this toner.

Comparative Example E-6

A black toner (6) of Comparative Example E-6 was obtained in the same manner as in Example E-6 except that no exemplary compound was used. The properties of this toner were measured in the same manner as in Example E-1, and the results thereof are shown in Table 16. In addition, a two-component type black developer (6) of Comparative Example E-6 was obtained in the same manner as in Example E-6 using this toner.

<Evaluation>

For the two-component type black developers (5), (S5) obtained in the above Examples E-6, F-6 and the two-component type black developer (6) obtained in the Comparative Example E-6, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, numbers from measurement values of two-component blow-off charge levels were rounded off to the first decimal place to make evaluations according to the same criteria as in Example E-1. The results are shown together in Table 16.

TABLE 16

| | | | Particle size distribution | | Electrifiability | | | |
|---|---|---|---|---|---|---|---|---|
| | | | | | Normal temperature and normal humidity (Q/M) | | High temperature and high humidity (Q/M) | |
| Examples | Compound number | Toners number | Average particle size (μm) | Ratio of fines (%) | 10 seconds | 300 seconds | 10 seconds | 300 seconds |
| E-1 | A-1 | Blue 1 | 6.8 | 4.9 | AA | AA | AA | AA |
| F-1 | A-2 | Blue S1 | 6.9 | 5.0 | AA | AA | AA | AA |
| E-2 | A-1 | Yellow 1 | 7.1 | 5.2 | AA | AA | AA | AA |
| F-2 | A-2 | Yellow S1 | 7.0 | 5.1 | AA | AA | AA | AA |
| E-3 | A-1 | Black 1 | 7.3 | 4.9 | AA | AA | AA | AA |
| F-3 | A-2 | Black S1 | 7.2 | 5.0 | AA | AA | AA | AA |
| E-4 | A-1 | Red 1 | 7.3 | 5.5 | AA | AA | AA | AA |
| F-4 | A-2 | Red S1 | 7.2 | 5.4 | AA | AA | AA | AA |
| E-5 | A-1 | Black 3 | 6.9 | 4.8 | AA | AA | AA | AA |
| F-5 | A-2 | Black S3 | 6.8 | 4.7 | AA | AA | AA | AA |
| E-6 | A-1 | Black 5 | 7.5 | 4.7 | AA | AA | AA | AA |
| F-6 | A-2 | Black S5 | 7.4 | 4.6 | AA | AA | AA | AA |
| Comparative Example E-1 | — | Blue 2 | 7.0 | 5.2 | C | C | C | C |
| E-2 | — | Yellow 2 | 7.2 | 4.9 | C | C | C | C |
| E-3 | — | Black 2 | 6.9 | 5.3 | C | B | C | B |
| E-4 | — | Red 2 | 7.1 | 5.1 | C | B | C | B |
| E-5 | — | Black 4 | 7.0 | 5.7 | C | B | C | C |
| E-6 | — | Black 6 | 7.5 | 4.9 | C | B | C | B |

Example E-7 to Examples E-12, F-7 to F-12 and Comparative Example E-7 to Comparative Example E-12

First, an image forming apparatus used in the image formation methods of Example E-7 to Examples E-12, F-7 to F-12 and Comparative Example E-7 to Comparative Example E-12 will be described. FIG. 5 is a schematic explanatory view of the cross section of an image forming apparatus for carrying out the image formation methods of Examples and Comparative Examples of the present invention. A photosensitive drum 1 shown in FIG. 5 has a photosensitive layer 1a having an organic photo semiconductor on a substrate 1b, and is configured to rotate in the direction indicated by the arrow, and its surface is electrically charged at a potential of about −600 V by a charge roller 2 being a charging member situated opposite to the photosensitive drum 1 and contacting and rotating with the drum. As shown in FIG. 5, the charge roller 2 has a metal core 2b covered with a conductive elastic layer 2a.

Next, the photosensitive drum 1 with its surface electrically charged is exposed to light 3 and at this time, on/off operations are performed on the photoconductor by a polygon mirror according to digital image information, whereby an electrostatic latent image with the potential of the exposed area being −100 V and the potential of the dark area being −600 V is formed. Subsequently, this electrostatic latent image on the photosensitive drum 1 is reverse-developed and thereby actualized using a plurality of development apparatuses 4-1, 4-2, 4-3 and 4-4, and thus a toner image is formed on the photosensitive drum 1. At that time, the two-component type developers obtained in Examples E-1 to E-6, F-1 to F-6 and Comparative Examples E-11 to E-6 were respectively used as developers to form a toner image with a yellow toner, a magenta toner, a cyan toner or a black toner. FIG. 6 is an enlarged sectional view of principal parts of development apparatuses 4 for two-component type developers used at that time.

Then, the toner images on the photosensitive drum 1 are transferred to an intermediate transfer member 5 contacting and rotating with the photosensitive drum 1. As a result, a four-color toner developed image is formed on the intermediate transfer member 5. A non-transferred toner remaining on the photosensitive drum 1 without being transferred is collected in a residual toner container 9 by a cleaning member 8.

The intermediate transfer member 5 comprises a metal core 5b as a support and an elastic layer 5a provided thereon as shown in FIG. 5. In this Example, the intermediate member 5 having the metal core 5b coated with the elastic layer 5b with a carbon black as a conductivity producer sufficiently dispersed in nitrile-butadiene rubber (NBR) was used. The degree of hardness of the elastic layer 5b measured in accordance with "JIS K-6301" was 30 degrees, and the volume resistivity was $10^9$ Ω·cm. The level of transfer current required for transferring the images from the photosensitive drum 1 to the intermediate transfer member 5 is about 5 μA, and this level of current was obtained by adding a voltage of +500 V to the metal core 5b.

The four-color toner developed image formed on the intermediate transfer member 5 is transferred to a transferring material such as a paper by a transfer roller 7, and is thereafter fixed by a heat-fixation apparatus H. The transfer roller 7 is provided thereon the core metal 7b with the outside diameter of 10 mm on which an elastic layer 7a is formed by coating of a foam of ethylene-propylene-diene based tridimensional copolymer (EPDM) dispersing carbon sufficiently therein as a conductivity producing material. The layer had a volume specific resistance of $10^6$ Ω·cm and a hardness degree of 35° as measured in accordance with "JIS K-6301". In addition, a voltage was applied to this transfer roller 7 to pass a transfer current of 15 μA therethrough.

In the apparatus shown in FIG. 5, a fixation apparatus of heated roll type having no oil coating mechanism shown in FIGS. 9 and 10 was used in the heat-fixation apparatus H. The both upper and lower rollers of the fixation apparatus used here had surface layers made of fluorine based resin. In addition, the diameter of the roller was 60 mm. The fixation temperature for fixation was 160° C., and the nipping width was set at 7 mm. Furthermore, a transfer residual toner on the photosensitive drum 1, which was collected by cleaning, was transported to a developing device by a reuse mechanism for reuse.

<Evaluation>

Two-component type developers produced using the toners of Examples E-1 to E-6, F-1 to F-6 and two-component type developers produced using toners of Comparative Examples E-1 to E-6 were used, respectively, to perform printout testing at a printout rate of 8 sheets (A4 size) per minute, supplying the developer, in a monochromatic intermittent mode (namely a mode in which the developing device is stopped for 10 seconds for each printout to accelerate the deterioration of a toner in a preliminary operation during restart of the device) at a normal temperature and normal humidity (25° C., 60% RH) and a high temperature and high humidity (30° C., 80% RH) under the conditions described above, and resulting printout images were evaluated for the following items. The evaluation results are shown together in Table 17.

[Evaluation of Printout Images]

With respect to image density, image fog, and transferability, evaluations were performed in the same manner as in Example D19.

In addition, in Example E-7 to Example E-12, Example F-7 to Example F-12 and Comparative Example E-7 to Comparative Example E-12, occurrences of scars and sticking residual toners on the surfaces of the photosensitive drum and intermediate transfer member, and their influence on printout images (matching with the image forming apparatus) were visually evaluated after 5000 images were outputted, and as a result, scars and sticking residual toners on the surfaces of the photosensitive drum and intermediate transfer member were not observed, and thus matching with the image forming apparatus was excellent for the system using two-component type developers of Example E-7 to Example E-12, Example F-7 to Example F-12. For the system using two-component type developers of Comparative Examples E-7 to E-12, on the other hand, sticking toners were observed on the surface of the photosensitive drum in all cases. In addition, for the system using two-component type developers of Comparative Examples E-7 to E-12, sticking toners and surface scars could be observed on the surface of the intermediate transfer member, and there was a problem in matching with image formation apparatus such that longitudinally striped defects occurred on the image.

TABLE 17

| Examples | Two-component type developer | Normal temperature and normal humidity | | | High temperature and high humidity | | |
|---|---|---|---|---|---|---|---|
| | | Image density | Image fog | Transferability | Image density | Image fog | Transferability |
| E-7 | blue 1 | AA | AA | AA | AA | AA | AA |
| F-7 | blue S1 | AA | AA | AA | AA | AA | AA |
| E-8 | yellow 1 | AA | AA | AA | AA | AA | AA |
| F-8 | yellow S1 | AA | AA | AA | AA | AA | AA |
| E-9 | black 1 | AA | AA | AA | AA | AA | AA |
| F-9 | black S1 | AA | AA | AA | AA | AA | AA |
| E-10 | red 1 | AA | AA | AA | AA | AA | AA |
| F-10 | red S1 | AA | AA | AA | AA | AA | AA |
| E-11 | black 3 | AA | AA | AA | AA | AA | AA |
| F-11 | black S3 | AA | AA | AA | AA | AA | AA |
| E-12 | black 5 | AA | AA | AA | AA | AA | AA |
| F-12 | black S5 | AA | AA | AA | AA | AA | AA |
| Comparative Example E-7 | blue 2 | C | C | C | C | C | C |
| E-8 | yellow 2 | C | C | C | C | C | C |
| E-9 | black 2 | B | B | C | B | C | C |
| E-10 | red 2 | B | B | C | B | C | C |
| E-11 | black 4 | B | B | C | C | C | C |
| E-12 | black 6 | B | B | C | B | C | C |

Example E-13 to Example E-15, Example F-13 to Example F-15, and Comparative Example E-13 to Comparative Example E-15

For carrying out the image formation methods of Example E-13 to Example E-15, Example F-13 to Example F-15, and Comparative Example E-13 to Comparative Example E-15, the toners obtained in Examples E-1 to E-3, Examples F-1 to F-3 and Comparative Examples E-1 to E-3 were used, respectively, as developers. In addition, for means for forming an image, an image forming apparatus with a commercially available laser beam printer LBP-EX (from Canon Inc.) modified so that it was provided with a reuse mechanism and reset as shown in FIG. 7 was used. That is, the image forming apparatus shown in FIG. 7 is provided with a system in which a non-transferred toner remaining on the photosensitive drum 20 after the transfer process is scraped off by an elastic blade 22 of a cleaner 21 abutting against the photosensitive drum 20, then sent into the cleaner 21 by a cleaner roller, passed through a cleaner reuse 23, and returned to the development device 26 via a hopper 25 by a supply pipe 24 with a carrier screw mounted thereon, and the toner collected in this way is reused.

In the image forming apparatus shown in FIG. 7, the surface of the photosensitive drum 20 is electrically charged by a primary charge roller 27. A rubber roller (diameter 12 mm, abutment pressure 50 gf/cm) coated with a nylon resin and having conductive carbon dispersed therein was used for the primary charge roller 27, and an electrostatic latent image with a dark area potential VD of −700 V and a light area potential VL of −200 V was formed on the electrostatic latent image-holding member (photosensitive drum 20) by laser exposure (600 dpi, not shown). As a toner carrier, a development sleeve 28 having a roughness degree Ra of 1.1 with the surface coated with a resin having a carbon black dispersed therein was used.

An enlarged sectional view of the principal part of the development apparatus for one-component type developers used in Example E-13 to Example E-15, Example F-13 to Example F-15 and Comparative Example E-13 to Comparative Example E-15 is shown in FIG. 8. For conditions for developing electrostatic latent images, the speed of the development sleeve 28 was set at a speed 1.1 times as high as the movement speed of the surface of the photosensitive drum 20 opposite thereto, and the space a between the photosensitive drum 20 and the development sleeve 28 (between S and D) was 270 µm. For the member for controlling the thickness of the toner, an abutting urethane rubber blade 29 was used. In addition, the set temperature of the heat-fixation apparatus for fixing a toner image was 160° C. Furthermore, for the fixation apparatus, a fixation apparatus shown in FIGS. 9 and 10 was used.

As described above, under the condition of normal temperature and normal humidity (25° C., 60% RH), images were printed out on up to 30,000 sheets at a printout rate of 8 sheets (A4 size) per minute, supplying the toner, in a continuous mode (namely, a mode in which the development device is not stopped, and thereby consumption of the toner is accelerated), and the densities of resulting printout images were measured to evaluate the durability according to the following criterion. In addition, the image from the 10,000 th printout was observed to make an evaluation about image fog according to the following criterion. At the same time, situations of the components comprising the image forming apparatus after the durability testing were observed to evaluate matching between each component and the above described toner in the same manner as in Example D35. The results thereof are shown together in Table 18.

TABLE 18

| | | Evaluation of printout image | | | | | Evaluation of matching with other apparatus | | | |
| --- | --- | --- | --- | --- | --- | --- | --- | --- | --- | --- |
| | | Change in image density during endurance | | | | 10 thousands | | | Fixation apparatus | |
| Examples | Toner | Initial | Thousand | 10 thousands | 30 thousands | fogged images | Development sleeve | Photosensitive drum | Surface characteristic | Toner fixation |
| E-13 | blue 1 | AA | AA | AA | AA | AA | AA | AA | AA | AA |
| F-13 | blue S1 | AA | AA | AA | AA | AA | AA | AA | AA | AA |
| E-14 | yellow 1 | AA | AA | AA | AA | AA | AA | AA | AA | AA |
| F-14 | yellow S1 | AA | AA | AA | AA | AA | AA | AA | AA | AA |
| E-15 | black 1 | AA | AA | AA | AA | AA | AA | AA | AA | AA |
| F-15 | black S1 | AA | AA | AA | AA | AA | AA | AA | AA | AA |
| Comparative Example E-3 | blue 2 | B | C | C | C | C | C | C | C | C |
| E-14 | yellow 2 | B | C | C | C | C | C | C | C | C |
| E-15 | black 2 | A | B | C | C | C | C | C | C | C |

Example E-16, F-16

Printout testing was performed, supplying the blue toners (1) and (S1) of Examples E-1 and F-1 respectively, in a continuous mode (namely, a mode in which the development device is not stopped, thereby accelerating consumption of the toner) in the same manner as in Examples E-13 and F-13 except that the toner reuse mechanism of the image forming apparatus of FIG. 7 was removed, and the printout rate was set at the level of 16 sheets (A4 size) per minute. The resulting printout images and the matching with the image evaluating apparatus used were evaluated for the same items as in Example E-13 to Example E-15, Example F-13 to Example F-15 and Comparative Examples E-13 to Comparative Example E-15. As the result, satisfactory results were obtained for all the items.

REFERENCE LIST

1. Japanese Patent Application Laid-Open No. H5-7492
2. Japanese Patent Publication No. H6-15604
3. Japanese Patent Publication No. H7-14352
4. Japanese Patent Publication No. H8-19227
5. Japanese Patent Application Laid-Open No. H5-93049
6. Japanese Patent Application Laid-Open No. H7-265065
7. Japanese Patent Application Laid-Open No. H9-191893
8. Japanese Patent No. 2642937
9. Japanese Patent No. 2989175
10. Japanese Patent Application Laid-Open No. H6-289644
11. Japanese Patent Application Laid-Open No. H8-262796
12. U.S. Pat. No. 5,004,664
13. Japanese Patent Application Laid-Open No. H7-120975
14. Japanese Patent Application Laid-Open No. H9-274335
15. Japanese Patent Application Laid-Open No. H9-281746
16. U.S. Pat. No. 4,480,021
17. U.S. Pat. No. 4,442,189
18. U.S. Pat. No. 4,925,765
19. Japanese Patent Application Laid-Open No. S60-108861
20. Japanese Patent Application Laid-Open No. S61-3149
21. Japanese Patent Application Laid-Open No. S63-38958
22. Japanese Patent Application Laid-Open No. S63-88564
23. Japanese Patent Application Laid-Open No. H7-72658
24. Japanese Patent Application Laid-Open No. H8-179564
25. Japanese Patent No. 2114410
26. Japanese Patent No. 2623684
27. Japanese Patent No. 2807795
28. Japanese Patent Application Laid-Open No. 2001-288256
29. Japanese Patent Application Laid-Open No. 2002-80571
30. Japanese Patent Application Laid-Open No. S59-190945
31. "Biodegradable Plastic Handbook" edited by Biodegradable Plastics Society, published by N.T.S. Co., Ltd., p. 178-197, 1995
32. Appl. Environ. Microbiol, 58 (2), 746 (1992)
33. Int. J. Biol. Macromol., 16 (3), 119 (1994)
34. Macromol. Chem. 191, 1957-1965 (1990)
35. Macromolecules, 24, 5256-5260 (1991)
36. Chirality, 3, 492-494 (1991)
37. Macromolecules, 29, 1762-1766 (1996)
38. Macromolecules, 32, 2889-2895 (1999)
39. Macromol. Chem. Phys., 195, 1665-1672 (1994)
40. Macromolecules, 29, 3432-3435 (1996)
41. Can. J. Microbiol., 41, 32-43 (1995)
42. Polymer International, 39, 205-213 (1996)
43. Macromolecules, 30, 1611-1615 (1997)
44. Polymer, 41, 1703-1709 (2000)
45. Macromolecular chemistry, 4, 289-293 (2001)
46. J. Biol. Chem., 218, 97-106 (1956)
47. J. Chem. Soc., Perkin. Trans. 1, 806 (1973)
48. Org. Synth., 4, 698 (1963)
49. J. Org. Chem., 46, 19 (1981)
50. J. Am. Chem. Soc., 81, 4273 (1959)
51. Macromolecules, 29, 1762-1766 (1996)

The invention claimed is:

1. A polyhydroxyalkanoate containing in a molecule thereof one or more 3-hydroxy-ω-(4-carboxyphenyl)alkanoic acid units represented by a chemical formula (1):

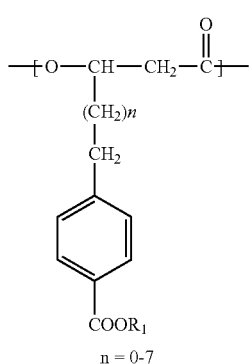
(1)

wherein n is an integer selected from 0 to 7; $R_1$ is an H, Na or K atom; and when more than one unit exists, n and $R_1$ may differ from unit to unit, respectively, with a proviso that the polyhydroxyalkanoate does not contain in the molecule thereof a unit represented by formula (16):

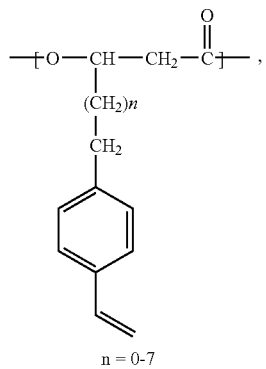
(16)

wherein n is an integer selected from 0 to 7.

2. The polyhydroxyalkanoate according to claim 1, wherein the 3-hydroxy-ω-(4-carboxyphenyl)alkanoic acid unit represented by the chemical formula (1) is a 3-hydroxy-ω-(4-carboxyphenyl)valeric acid unit represented by a chemical formula (2):

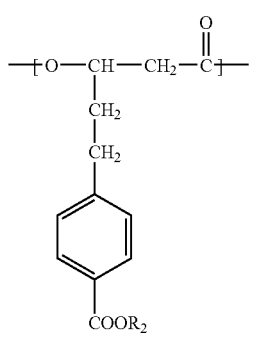
(2)

wherein $R_2$, an H, Na or K atom and, when more than one unit exists, it may differ from unit to unit.

3. The polyhydroxyalkanoate according to claim 1, wherein the polyhydroxyalkanoate contains, besides the 3-hydroxy-ω-(4-carboxyphenyl)alkanoic acid unit represented by the chemical formula (1), at least either a 3-hydroxy-ω-substituted alkanoic acid unit represented by a chemical formula (3):

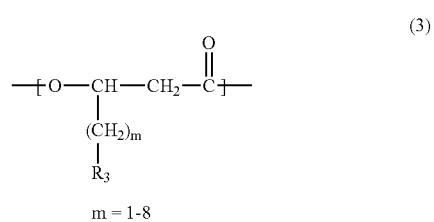
(3)

m = 1-8 wherein m is an integer selected from 1 to 8; $R_3$ comprises a residue having a ring structure of either a phenyl or a thienyl structure; and when more than one unit exists, m and $R_3$ may differ from unit to unit, respectively; or a 3-hydroxy-ω-cyclohexylalkanoic acid unit represented by a chemical formula (4):

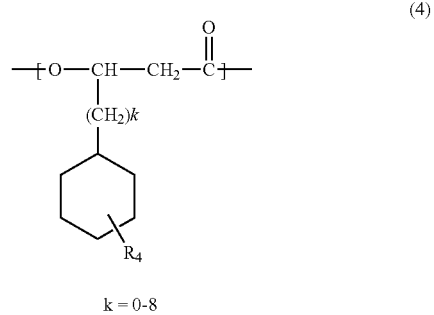
(4)

k = 0-8 wherein $R_4$ represents a substituent on a cyclohexyl group and is an H atom, a CN group, an $NO_2$ group, a halogen atom, a $CH_3$ group, a $C_2H_5$ group, a $C_3H_7$ group, a $CF_3$ group, a $C_2F_5$ group or a $C_3F_7$ group; k is an integer selected from 0 to 8; and when more than one unit exists, k and $R_4$ may differ from unit to unit.

4. The polyhydroxyalkanoate according to claim 3, wherein $R_3$ in the chemical formula (3) having a phenyl or thienyl structure is at least any one selected from the group consisting of residues represented by chemical formulae (5), (6), (7), (8), (9), (10), (11), (12) and (15), wherein the chemical formula (5) represents a group consisting of unsubstituted and substituted phenyl groups:

(5)

wherein $R_5$ represents a substituent on the aromatic ring and is an H atom, a halogen atom, a CN group, an $NO_2$ group, a $CH_3$ group, a $C_2H_5$ group, a $C_3H_7$ group, $COOR_6$ ($R_6$ represents any one of H, Na and K atoms), a $CF_3$ group, a $C_2F_5$ group or a $C_3F_7$ group; and when more than one unit exists, $R_5$ may differ from unit to unit;

the chemical formula (6) represents a group consisting of unsubstituted and substituted phenoxy groups:

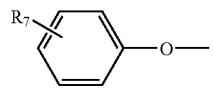

(6)

wherein $R_7$ represents a substituent on the aromatic ring and is an H atom, a halogen atom, a CN group, an $NO_2$ group, a $CH_3$ group, a $C_2H_5$ group, a $C_3H_7$ group, an $SCH_3$ group, a $CF_3$ group, a $C_2F_5$ group or a $C_3F_7$ group; and when more than one unit exists, $R_7$ may differ from unit to unit;

the chemical formula (7) represents a group consisting of unsubstituted and substituted benzoyl groups:

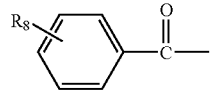

(7)

wherein $R_8$ represents a substituent on the aromatic ring and is an H atom, a halogen atom, a CN group, an $NO_2$ group, a $CH_3$ group, a $C_2H_5$ group, a $C_3H_7$ group, a $CF_3$ group, a $C_2F_5$ group or a $C_3F_7$ group; and when more than one unit exists, $R_8$ may differ from unit to unit;

the chemical formula (8) represents a group consisting of unsubstituted and substituted phenylsulfanil groups:

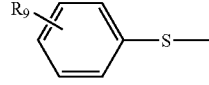

(8)

wherein $R_9$ represents a substituent on the aromatic ring and is an H atom, a halogen atom, a CN group, an $NO_2$ group, a $COOR_{10}$, an $SO_2R_{11}$ ($R_{10}$ represents any one of an H atom, an Na atom, a K atom, a $CH_3$ group and a $C_2H_5$ group and $R_{11}$ represents any one of an OH group, an ONa group, an OK group, a halogen atom, an $OCH_3$ group and $OC_2H_5$ group), a $CH_3$ group, a $C_2H_5$ group, a $C_3H_7$ group, a $(CH_3)_2$—CH group or a $(CH_3)_3$—C group; and when more than one unit exists, $R_9$ may differ from unit to unit;

the chemical formula (9) represents a group consisting of unsubstituted and substituted (phenylmethyl)sulfanil groups:

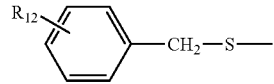

(9)

wherein $R_{12}$ represents a substituent on the aromatic ring and is an H atom, a halogen atom, a CN group, an $NO_2$ group, a $COOR_{13}$, an $SO_2R_{14}$ ($R_{13}$ represents any one of an H atom, an Na atom, a K atom, a $CH_3$ group and a $C_2H_5$ group and $R_{14}$ represents any one of an OH group, an ONa group, an OK group, a halogen atom, an $OCH_3$ group and $OC_2H_5$ group), a $CH_3$ group, a $C_2H_5$ group, a $C_3H_7$ group, a $(CH_3)_2$—CH group or a $(CH_3)_3$—C group; and when more than one unit exists, $R_{12}$ may differ from unit to unit;

the chemical formula (10) represents 2-thienyl group:

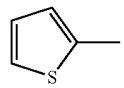

(10)

the chemical formula (11) represents a 2-thienylsulfanil group:

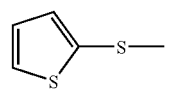

(11)

the chemical formula (12) represents a 2-thienylcarbonyl group:

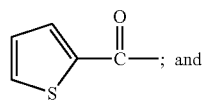

(12)

; and the chemical formula (15) represents a group of a (phenylmethyl)oxy group:

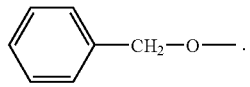

(15)

5. The polyhydroxyalkanoate according to claim 1, wherein a number average molecular weight of the polyhydroxyalkanoate is selected to fall in a range of 1000 to 1000000.

6. A resin composition comprising a resin (A) and a thermoplastic resin (B), the resin (A) being a polyhydroxyalkanoate that contains, in a polymer molecule thereof, at least one kind of unit of the 3-hydroxy-ω-(4-carboxyphenyl)alkanoic acid units represented by the chemical formula (1):

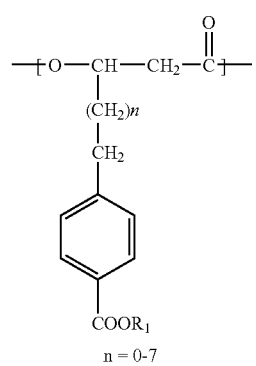

(1)

n = 0-7 wherein n is an integer selected from the range shown in the formula; $R_1$ is an H, Na or K atom; and when more than one unit exists, n and $R_1$ may differ from unit to unit, respectively, with a proviso that the polyhydroxyalkanoate does not contain in the polymer molecule thereof a unit represented by formula (16):

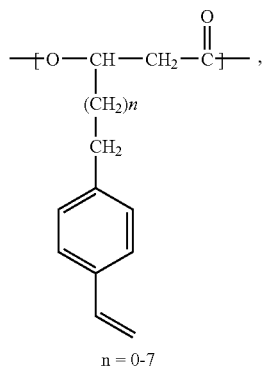

(16)

n = 0-7 wherein n is an integer selected from 0 to 7.

7. A resin composition comprising a resin (A) and a thermoplastic resin (B), wherein the resin (A) is a polyhydroxyalkanoate according to claim 2.

8. The resin composition according to claim 6, wherein the thermoplastic resin (B) comprises one or more resins selected from the group consisting of polyester-based resin, polystyrene-based resin, polypropylene-based resin, polyethylene terephthalate-based resin, polyurethane-based resin, polyvinyl-based resin and polyamide-based resin.

9. The resin composition according to claim 8, wherein the polystyrene-based resin is polystyrene.

10. The resin composition according to claim 6, wherein the polyester-based resin is poly-ε-caprolactone or polylactic acid.

11. The resin composition according to claim 6, further comprising additives for resin.

12. A molding molded from a resin composition according to claim 6.

13. The molding according to claim 12, wherein the molding is a container.

14. The molding according to claim 12, wherein the molding is biodegradable.

15. The molding according to claim 14, wherein the molding is at least any one selected from the group consisting of containers for foods, drinks, toiletries, drugs and cosmetics.

16. The molding according to claim 12, wherein the molding is used in a temperature environment of 140° C. or less.

17. A method of producing a molding comprising heating a resin composition according to claim 6 for molding.

18. A charge controlling agent for controlling a charged state of powder and granular materials, the agent comprising a polyhydroxyalkanoate that has at least one kind of unit selected from the group consisting of the 3-hydroxy-o-(4-carboxyphenyl)alkanoic acid units represented by the chemical formula (1):

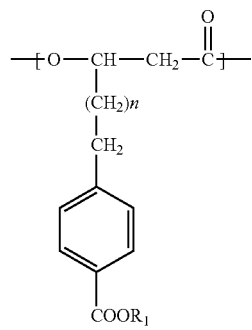

(1)

n = 0-7 wherein n is an integer selected from the range shown in the formula; $R_1$ is an H, Na or K atom; and when more than one unit exists, n and $R_1$ may differ from unit to unit, respectively, with a proviso that the polyhydroxyalkanoate does not contain a unit represented by formula (16):

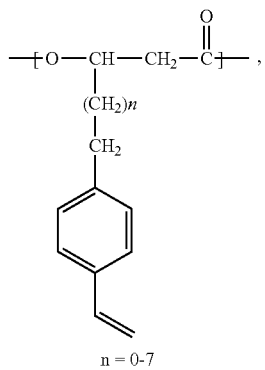

(16)

n = 0-7 wherein n is an integer selected from 0 to 7.

19. A charge controlling agent for controlling a charged state of powder and granular materials, the agent comprising a polyhydroxyalkanoate according to claim 2.

20. The charge controlling agent according to claim 18, wherein the powder and granular material is a toner for developing electrostatic latent images.

21. A toner for developing an electrostatic latent image comprising at least a binder resin, a colorant and a charge controlling agent according to claim 18.

22. A binder resin for forming a resin-based powder and granular material comprising a polyhydroxyalkanoate whose polymer molecule comprises at least one kind of unit selected from the group consisting of the 3-hydroxy-o-(4-carboxyphenyl)alkanoic acid units represented by the chemical formula (1):

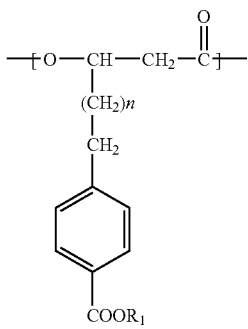

(1)

n = 0-7 wherein n is an integer selected from the range shown in the formula; $R_1$ is an H, Na or K atom; and when more than one unit exists, n and $R_1$ may differ from unit to unit, respectively, with a proviso that the polyhydroxyalkanoate does not contain in the polymer molecule thereof a unit represented by formula (16):

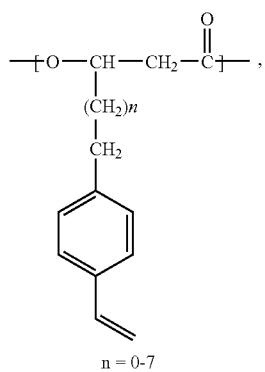

(16)

n = 0-7 wherein n is an integer selected from 0 to 7.

23. A binder resin for forming a resin-based powder and granular material comprising a polyhydroxyalkanoate according to claim 2.

24. The binder resin according to claim 22, wherein the resin further comprises a thermoplastic resin, besides the polyhydroxyalkanoate, and a content of the polyhydroxyalkanoate is larger than that of the thermoplastic resin.

25. A binder resin for forming a resin-based powder and granular material comprising a polyhydroxyalkanoate whose polymer molecule comprises at least one kind of unit selected from the group consisting of the 3-hydroxy-o-(4-carboxyphenyl)alkanoic acid units represented by the chemical formula (1):

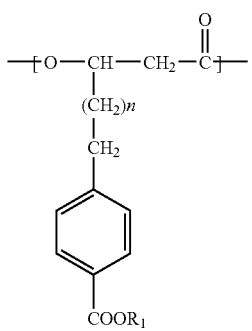

(1)

n = 0-7 wherein n is an integer selected from the range shown in the formula; $R_1$ is an H, Na or K atom; and when more than one unit exists, n and $R_1$ may differ from unit to unit, respectively; and a resin composition according to claim 8.

26. The binder resin according to claim 24, wherein the thermoplastic resin is one or more selected from the group consisting of polycaprolactone and polylactic acid.

27. The binder resin according to claim 22, wherein the resin has a number average molecular weight of 2,000 or more and 300,000 or less.

28. The binder resin according to claim 22, wherein the binder resin has a glass transition point of 30 to 80° C. and a softening point of 60 to 170° C.

29. The binder resin according to claim 22, wherein the resin-based powder and granular material is a toner for developing electrostatic latent images.

30. A toner for developing electrostatic latent images containing a binder resin according to claim 22.

31. An image forming method comprising at least the steps of:

charging an electrostatic latent image-holding member by applying voltage to a charging member from outside;

forming an electrostatic latent image on the charged electrostatic latent image-holding member;

developing the electrostatic latent image with a toner for developing electrostatic latent images to form a toner image on the electrostatic latent image-holding member;

transferring the toner image on the electrostatic latent image-holding member to a recording medium; and fixing the toner image on the recording medium by heat, wherein the toner is a toner according to claim 21.

32. The image forming method according to claim 31, wherein the transferring step comprises a first transferring step of transferring the toner image on the electrostatic latent image-holding member to an intermediate transfer medium; and a second transferring step of transferring the toner image on the intermediate transfer medium to the recording medium.

33. An image forming apparatus comprising at least charging means for charging an electrostatic latent image-holding member by applying voltage to a charging member from outside; electrostatic latent image forming means for forming an electrostatic latent image on the charged electrostatic latent image-holding member; developing means for developing the electrostatic charge image with a toner for developing electrostatic charge images to form a toner image on the electrostatic latent image-holding member; transferring means for transferring the toner image on the electrostatic latent image-holding member to a recording medium; and fixing means for fixing the toner image on the recording medium by heat, wherein the toner for developing electrostatic charge images is a toner according to claim 21.

34. The image forming apparatus according to claim 33, wherein the transferring means comprises a first transferring means for transferring the toner image on the electrostatic latent image-holding member to an intermediate transfer medium; and a second transferring means for transferring the toner image on the intermediate transfer medium to the recording medium.

* * * * *